US009422347B2

(12) United States Patent
Mayfield et al.

(10) Patent No.: US 9,422,347 B2
(45) Date of Patent: Aug. 23, 2016

(54) ALGAL PRODUCED MALARIAL TRANSMISSION BLOCKING VACCINES

(75) Inventors: Stephen P. Mayfield, Cardiff, CA (US); James A. Gregory, San Diego, CA (US); Carla S. Jones, Austin, TX (US); Michael J. Hannon, Seattle, WA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/123,519

(22) PCT Filed: May 1, 2012

(86) PCT No.: PCT/US2012/036010
§ 371 (c)(1),
(2), (4) Date: Apr. 3, 2014

(87) PCT Pub. No.: WO2012/170125
PCT Pub. Date: Dec. 13, 2012

(65) Prior Publication Data
US 2014/0219971 A1    Aug. 7, 2014

Related U.S. Application Data

(60) Provisional application No. 61/493,911, filed on Jun. 11, 2011.

(51) Int. Cl.
| *A01N 63/00* | (2006.01) |
| *C07K 14/445* | (2006.01) |
| *A61K 39/015* | (2006.01) |
| *C12N 1/12* | (2006.01) |
| *C12N 15/82* | (2006.01) |
| *A61K 39/00* | (2006.01) |

(52) U.S. Cl.
CPC ............. *C07K 14/445* (2013.01); *A61K 39/015* (2013.01); *C12N 1/12* (2013.01); *C12N 15/8214* (2013.01); *C12N 15/8258* (2013.01); *A61K 2039/517* (2013.01); *A61K 2039/6037* (2013.01)

(58) Field of Classification Search
None
See application file for complete search history.

(56) References Cited

U.S. PATENT DOCUMENTS

2013/0022637 A1 *   1/2013   Yoshida et al. ............ 424/199.1

FOREIGN PATENT DOCUMENTS

| WO | 01/98335 | 12/2001 |
| WO | 2010/040000 | 4/2010 |
| WO | 2012/170125 | 12/2012 |

OTHER PUBLICATIONS van Dijk et al. Cell, vol. 104, pp. 153-164, Jan. 12, 2001.*
Maufield et al. (Current Opinion in Biology vol. 18, pp. 126-133, 2007).*
Engineering the Chloroplast Targeted Malarial Vaccine Antigens in Chlamydomonas Starch Granules David Dauvilléeet al. PLOS ONE, vol. 5,No. 12, 2010.*
International Search Report dated Nov. 22, 2012 issued in International Application No. PCT/US2012/036010.
Written Opinion dated Nov. 22, 2012 issued in International Application No. PCT/US2012/036010.
International Preliminary Report on Patentability dated Dec. 10, 2013 issued in International Application No. PCT/US2012/036010.
Blagborough, et al. 2009 "Plasmodium berghei HAP2 induces strong malaria transmission-blocking immunity in vivo and in vitro." *Vaccine* 27(38):5187-5194.
Chou, et al. 2003 "Tic40, a membrane-anchored co-chaperone homolog in the chloroplast protein translocon." *EMBO J* 22(12):2970-2980.
Coragliotti, et al. 2011 "Molecular factors affecting the accumulation of recombinant proteins in the Chlamydomonas reinhardtii chloroplast." *Mol Biotechnol*. 48(1): 60-75.
Dauvillee, et al. 2010 "Engineering the Chloroplast Targeted Malarial Vaccine Antigens in Chlamydomonas Starch Granules," *PLoS ONE* 5(12):1-8.
Fletcher, et al. 2007 "Optimization of recombinant protein expression in the chloroplasts of green algae." *Adv Exp Med Biol*. 616:9098, Abstract Only.
Gregory, et al. 2012 "Algae-Produced Pfs25 Elicits Antibodies That Inhibit Malaria Transmission," *PLoS ONE* 7(5):1-10.
Gregory, et al. 2013 "Alga-Produced Cholera Toxin-Pfs25 Fusion Proteins as Oral Vaccines," *Applied and Environmental Microbiology* 79(13):3917-3925.
Gregory, et al. 2014 "Developing inexpensive malaria vaccines from plants and algae," *Appl Microbiol Biotechnol* pp. 1-8.
Heitzer, et al. 2007 "Influence of codon bias on the expression of foreign genes in microalgae." *Adv Exp Med Biol*. 616:46-53, Abstract Only.
Jones, et al. 2012 "Steps toward a globally available malaria vaccine: Harnessing the potential of algae for future low cost vaccines." *Bioengineered* 4(3):164-167.
Jones, et al. 2013 "Heterologous expression of the C-terminal antigenic domain of the malaria vaccine candidate Pfs48/45 in the green algae *Chlamydomonas reinhardtii*," *Appl Microbiol Biotechnol* 97:1987-1995.
Patra, et al. 2015 "Algae-produced malaria transmission-blocking vaccine candidate Pfs25 formulated with a human use-compatible potent adjuvant induces high affinity antibodies that block *Plasmodium falciparum* infection of mosquitoes," *Infect Immun*. Feb. 17, accepted manuscript.
Rasala, et al. 2011 "The microalga Chlamydomonas reinhardtii as a platform for the production of human protein therapeutics." *Bioeng Bugs* 2(1):5-54, Abstract Only.
Rasala, et al. 2010 "Production of therapeutic proteins in algae, analysis of expression of seven human proteins in the chloroplast of Chlamydomonas reinhardtii." *Plant Biotechnol J*. 8(6):719-733, Abstract Only.
Wu, et al. 2011 "Improved biohydrogen production with an expression of codon-optimized hemH and Iba genes in the chloroplast of Chlamydomonas reinhardtii." *Bioresour Technol*. 102(3):2610-2616, Abstract Only.

* cited by examiner

*Primary Examiner* — Jana Hines
*Assistant Examiner* — Khatol Shahnan Shah
(74) *Attorney, Agent, or Firm* — Weaver Austin Villeneuve & Sampson LLP

(57) ABSTRACT

The present invention relates to the production of malaria transmission blocking vaccines in single-celled green algae, particularly algae of the genus *Chlamydomonas*, e.g., *Chlamydomonas reinhardtii*; the immunogenic *Plasmodium* polypeptides produced and compositions comprising them; and methods for preventing, ameliorating, reducing, delaying, treating and blocking the transmission of malaria by administration of immunogenic *Plasmodium* polypeptides produced in an algal host cell.

25 Claims, 24 Drawing Sheets

| C. reinhardtii Strain Designation | Plasmid Design |
|---|---|
| 389 | D2:Flag-c.r.-Pfs 48/45 AA 178-448:D1 |
| 391 | D1:Flag-c.r.-Pfs 48/45 AA 178-448:D1 |
| 399 | D2:SAA-c.r.-Pfs 48/45 AA 178-427:D1 |
| 401 | D2:SAA-c.r.-Pfs 48/45 AA 178-448:D1 |
| 472 | D1:SAA-c.r.-Pfs 48/45 AA 27-448:D1 |
| 484 | D2:SAA-c.r.-Pfs 48/45 AA 27-448:D1 |
| 547 | D1:SAA-c.r.-Pfs 48/45 AA 27-426:D1 |
| 549 | D2:Flag-c.r.-Pfs 48/45 AA 27-426:D1 |
| 551 | D1:Flag-c.r.-Pfs 48/45 AA 27-426:D1 |

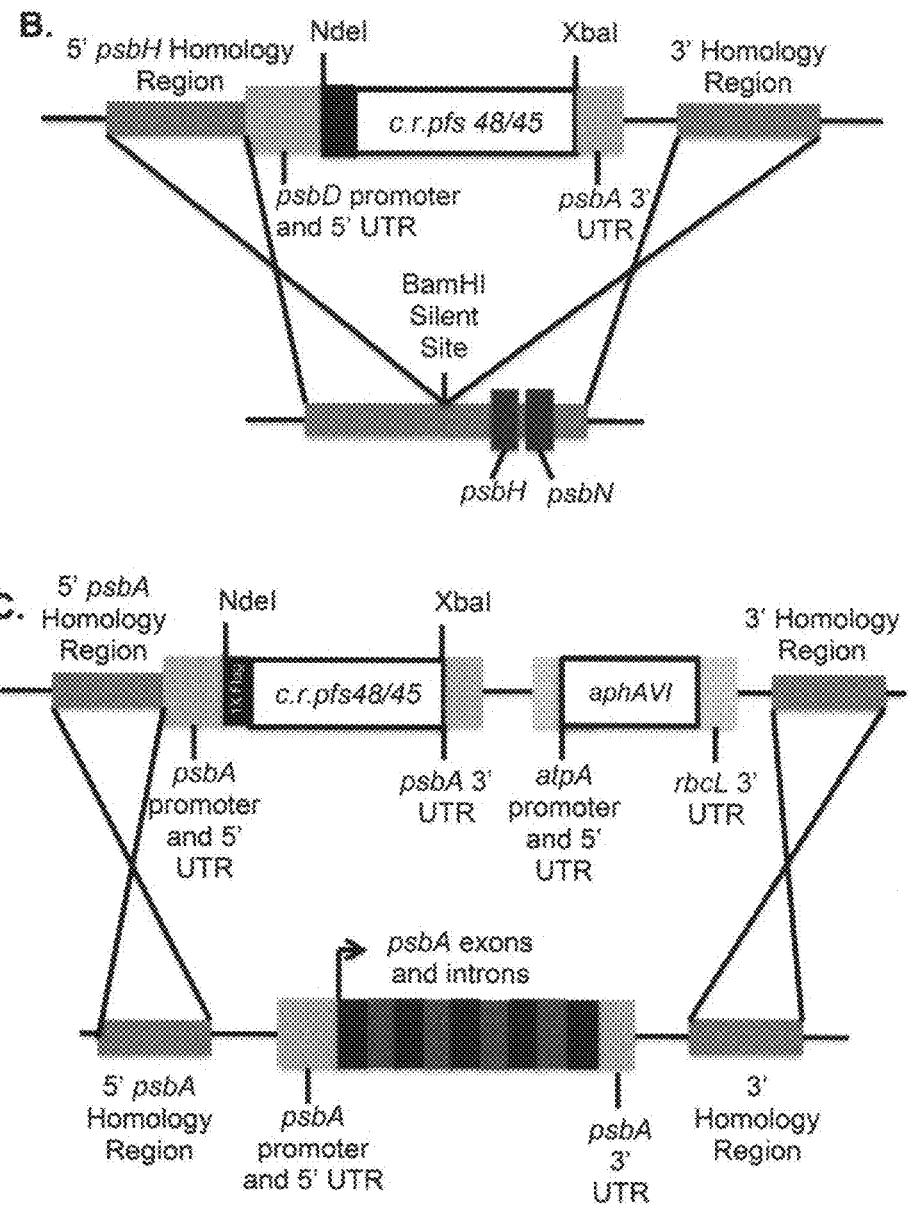
Fig. 9B-C

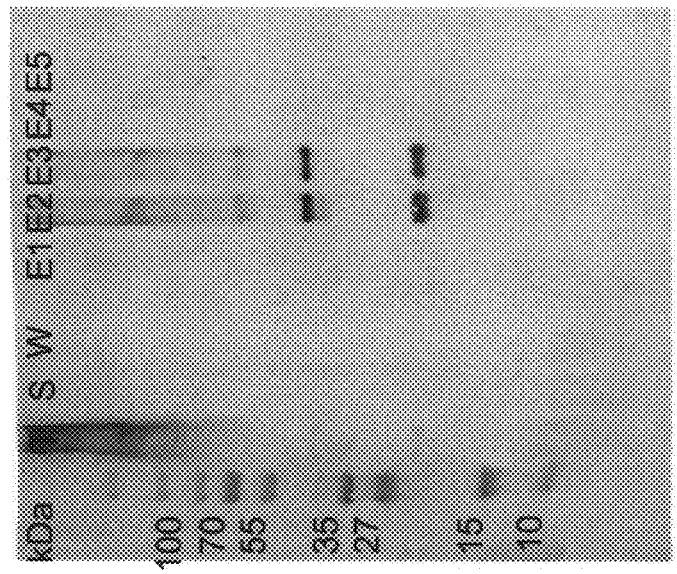
Fig. 11A-B

SEQUENCE LISTING

<160> NUMBER OF SEQ ID NOS: 51

<210> SEQ ID NO 1
<211> LENGTH: 1266
<212> TYPE: DNA
<213> ORGANISM: Plasmodium sp.

```
<400> SEQUENCE: 1
ggtaataatg actttttgtaa accatctagt ttaaatagtg aaatttcagg tttcattggt      60
tataaatgta acttttctaa tgaaggtgtt cacaacttaa aacctgatat gcgtgaacgt     120
cgtagtattt tctgtactat tcattcatat ttcatttatg ataaaattcg tttaattatt     180
cctaaaaaat catcttctcc tgaattcaaa attttaccag aaaaatgttt tcaaaaagtt     240
tatacagact atgaaaatcg tgttgaaact gatatttctg aattaggttt aattgaatat     300
gaaattgaag aaaatgatac aaatccaaat tacaatgaac gtactttaac aatttcacca     360
ttctcaccta aagatattga attcttttgt ttttgtgaca atactgaaaa agttatttca     420
tctattgaag gtcgttcagc aatggttcat gtacgtgtat aaaatacccc acataatatt     480
ttatttacta atttaactaa cgatttattt acatatttac ctaaaacata caacgaatct     540
aattttgttt caaatgtatt agaagtagaa ttaaacgatg gtgaattatt cgttttagct     600
tgtgaattaa ttaataaaaa atgtttccaa gaaggtaaag aaaaagcatt atacaaaagt     660
aacaaaatta tttaccacaa aaacttaaca attttcaaag caccttttta tgttacatct     720
aaagatgtaa atacagaatg tacatgtaaa tttaaaaata acaattacaa aattgtttta     780
aaaccaaaat atgaaaaaaa agttattcat ggttgtaatt tctcatctaa tgttagtagt     840
aaacatacat tcacagattc attagatatt agtttagttg acgattcagc acatattagt     900
tgtaacgttc atttaagtga acctaaatac aatcatttag ttggtttaaa ttgtcctggt     960
gatattattc cagattgttt ttttcaagta tatcaaccag aatctgaaga attagaacca    1020
agtaatattg tttatttaga ttctcaaatt aacattggtg acattgaata ttatgaagac    1080
gctgaaggtg acgataaaat taaattattc ggtattgttg gtagtattcc aaaaacaaca    1140
tcatttacat gtatttgtaa aaaagacaaa aaagtgctt acatgacagt tactattgat    1200
agtgcatact acggtttctt agcaaaaaca ttcattttct taattgtagc tattttatta    1260
tacatt                                                               1266

<210> SEQ ID NO 2
<211> LENGTH: 529
<212> TYPE: DNA
<213> ORGANISM: Plasmodium sp.

<400> SEQUENCE: 2
catatggcaa aagttacagt tgatactgta tgtaaacgtg gtttcttaat tcaaatgtca      60
ggtcacttag aatgtaaatg tgaaaatgat ttagtattag taaatgaaga acatgtgaa     120 gaaaaagttt taaatgtga tgaaaaaact gttaataaac catgtggtga tttctcaaaa     180
tgtattaaaa ttgatggtaa cccagtatct tatgcttgta atgtaattt aggttacgac     240 atggttaata atgtatgtat tccaaatgaa tgtaaaaacg taacttgtgg taatggtaaa     300
tgtattttag atacatctaa tcctgtaaaa actggtgttt gttcttgtaa tattggtaaa     360
gttccaaacg tacaagatca aaacaaatgt tcaaagatg gtgaaacaaa atgttcttta     420
aaatgtttaa agaaacga aacatgtaaa gctgttgatg gtatttacaa atgtgattgt     480
aaagatggtt tcattattga taacgaatca tctattttgta caaccggtg               529

<210> SEQ ID NO 3
<211> LENGTH: 603
<212> TYPE: DNA
<213> ORGANISM: Plasmodium sp.

<400> SEQUENCE: 3
```

```
catatggcaa aagttacagt tgatactgta tgtaaacgtg gtttcttaat tcaaatgtca      60
ggtcacttag aatgtaaatg tgaaaatgat ttagtattag taaatgaaga acatgtgaa     120
gaaaaagttt taaatgtga tgaaaaaact gttaataaac catgtggtga tttctcaaaa     180
tgtattaaaa ttgatggtaa cccagtatct tatgcttgta atgtaatttt aggttacgac     240
atggttaata atgtatgtat tccaaatgaa tgtaaaaacg taacttgtgg taatggtaaa     300
tgtatttttag atacatctaa tcctgtaaaa actggtgttt gttcttgtaa tattggtaaa    360
gttccaaacg tacaagatca aaacaaatgt tcaaagatg gtgaaacaaa atgttctta      420
aaatgtttaa aagaaaacga acatgtaaa gctgttgatg gtatttacaa atgtgattgt     480
aaagatggtt tcattattga taacgaatca tctatttgta caaccggtga aaacttatac    540
tttcaaggtt caggtggtgg tggttcagat tataaagatg acgatgataa aggttaatct    600
aga                                                                  603
```

<210> SEQ ID NO 4
<211> LENGTH: 1271
<212> TYPE: DNA
<213> ORGANISM: Plasmodium sp.

<400> SEQUENCE: 4

```
catatggcaa aagttacagt tgatactgta tgtaaacgtg gtttcttaat tcaaatgtca      60
ggtcacttag aatgtaaatg tgaaaatgat ttagtattag taaatgaaga acatgtgaa     120
gaaaaagttt taaatgtga tgaaaaaact gttaataaac catgtggtga tttctcaaaa     180
tgtattaaaa ttgatggtaa cccagtatct tatgcttgta atgtaatttt aggttacgac     240
atggttaata atgtatgtat tccaaatgaa tgtaaaaacg taacttgtgg taatggtaaa     300
tgtatttttag atacatctaa tcctgtaaaa actggtgttt gttcttgtaa tattggtaaa    360
gttccaaacg tacaagatca aaacaaatgt tcaaagatg gtgaaacaaa atgttctta      420
aaatgtttaa aagaaaacga acatgtaaa gctgttgatg gtatttacaa atgtgattgt     480
aaagatggtt tcattattga taacgaatca tctatttgta caaccggtgg ttcaggtggt    540
ggtggatctg ctaaaggtga agaattattc acaggtgttg tacctatttt agtagaatta    600
gacggtgatg taaacggtca caattttca gtttctggtg aaggtgaagg tgacgcaact    660
tatggtaaat taacacttaa attcatttgt actacaggta aattaccagt accttggcca    720
actttagtta caacttttac ataccggtgta caatgtttca gtcgttaccc tgatcacatg    780
aaacaacatg actttttcaa atctgctatg ccagaaggtt atgttcaaga acgtactatt    840
ttttcaaag atgacggtaa ttataaaaca cgtgctgaag taaaatttga aggtgatact    900
ttagttaacc gtattgaatt aaaaggtatt gacttcaaag aagatggtaa tattttaggt     960
cacaaacttg aatataacta caattcacat aacgtatata ttatggcaga caaacaaaaa    1020
aatggtatta agtaaacttt taaaattcgt cataatatcg aggatggttc tgtacaatta    1080
gctgaccact atcaacaaaa cacaccaatt ggtgatggtc ctgttttact tccagacaat    1140
cattatttaa gtactcaatc tgctttatca aaagatccta acgaaaaacg tgaccacatg    1200
gtattacttg aatttgttac agcagctggt attactcacg gtatggatg aattatacaa     1260
ataaatctag a                                                         1271
```

<210> SEQ ID NO 5
<211> LENGTH: 828
<212> TYPE: DNA

<213> ORGANISM: Plasmodium sp.

<400> SEQUENCE: 5

```
catatgggtt cattacaaga ttcagaagta aaccaagaag ctaaaccaga agtaaaacca      60
gaagtaaaac ctgaaactca cattaattta aaagtatcag acggttcatc agaaattttc     120
tttaaaatta aaaaacaac accttta cgt cgtttaatgg aagcttttgc aaaacgtcaa     180
ggtaaagaaa tggactcatt acgtttctta tatgatggta ttcgtattca agcagaccaa     240
gcacctgaag atttagatat ggaagataat gatattattg aagcacatcg tgaacaaatt     300
ggtggtaccg gtgcaaaagt tacagttgat actgtatgta acgtggtttt cttaattcaa     360
atgtcaggtc acttagaatg taaatgtgaa atgatttag tattagtaaa tgaagaaaca     420
tgtgaagaaa aagttttaaa atgtgatgaa aaaactgtta ataaaccatg tggtgatttc     480
tcaaaatgta ttaaaattga tggtaacccca gtatcttatg cttgtaaatg taatttaggt     540
tacgacatgg ttaataatgt atgtattcca aatgaatgaa aaacgtaac ttgtggtaat      600
ggtaaatgta ttttagatac atctaatcct gtaaaaactg gtgtttgttc ttgtaatatt     660
ggtaaagttc caaacgtaca agatcaaaac aaatgttcaa agatggtga aacaaaatgt      720
tctttaaaat gtttaaaaga aaacgaaaca tgtaaagctg ttgatggtat ttacaaatgt     780
gattgtaaag atggtttcat tattgataac gaatcatcta tttgtaca                  828
```

<210> SEQ ID NO 6
<211> LENGTH: 484
<212> TYPE: DNA
<213> ORGANISM: Plasmodium sp.

<400> SEQUENCE: 6

```
catatgcgtg taacagaaaa tacaatttgt aaatatggtt atttaattca aatgtcaaat      60
cactatgaat gtaaatgtat tgaaggttat gtattaatta atgaagatac atgtggtaaa     120
aaagtagtat gtgataaagt tgaaaattca tttaaagcat gtgatgaata tgcatattgt     180
tttgacttag gtaataaaaa caatgaaaaa caaattaaat gtatgtgtcg tacagaatat     240
acattaacag caggtgtttg tgttccaaat gtatgtcgtg acaaagtttg tggtaaaggt     300
aaatgtattg tagatccagc taattcttta acacacacat gttcttgtaa tattggtaca     360
atttaaaacc aaaacaaatt atgtgatatt caaggtgata caccttgttc tttaaaatgt     420
gcagaaaatg aagtttgtac attagaaggt aactattata catgtaaaga agatcctacc     480
ggtg                                                                   484
```

<210> SEQ ID NO 7
<211> LENGTH: 558
<212> TYPE: DNA
<213> ORGANISM: Plasmodium sp.

<400> SEQUENCE: 7

```
catatgcgtg taacagaaaa tacaatttgt aaatatggtt atttaattca aatgtcaaat      60
cactatgaat gtaaatgtat tgaaggttat gtattaatta atgaagatac atgtggtaaa     120
aaagtagtat gtgataaagt tgaaaattca tttaaagcat gtgatgaata tgcatattgt     180
tttgacttag gtaataaaaa caatgaaaaa caaattaaat gtatgtgtcg tacagaatat     240
acattaacag caggtgtttg tgttccaaat gtatgtcgtg acaaagtttg tggtaaaggt     300
aaatgtattg tagatccagc taattcttta acacacacat gttcttgtaa tattggtaca     360
atttaaaacc aaaacaaatt atgtgatatt caaggtgata caccttgttc tttaaaatgt     420
```

```
gcagaaaatg aagtttgtac attagaaggt aactattata catgtaaaga agatcctacc    480
ggtgaaaact tatactttca aggttcaggt ggtggtggtt cagattataa agatgacgat    540
gataaaggtt aatctaga                                                  558
```

<210> SEQ ID NO 8
<211> LENGTH: 1226
<212> TYPE: DNA
<213> ORGANISM: Plasmodium sp.

<400> SEQUENCE: 8

```
catatgcgtg taacagaaaa tacaatttgt aaatatggtt atttaattca aatgtcaaat     60
cactatgaat gtaaatgtat tgaaggttat gtattaatta atgaagatac atgtggtaaa    120
aaagtagtat gtgataaagt tgaaaattca tttaaagcat gtgatgaata tgcatattgt    180
tttgacttag gtaataaaaa caatgaaaaa caaattaaat gtatgtgtcg tacagaatat    240
acattaacag caggtgtttg tgttccaaat gtatgtcgtg acaaagtttg tggtaaaggt    300
aaatgtattg tagatccagc taattcttta acacacacat gttcttgtaa tattggtaca    360
attttaaacc aaaacaaatt atgtgatatt caaggtgata caccttgttc tttaaaatgt    420
gcagaaaatg aagtttgtac attagaaggt aactattata catgtaaaga agatcctacc    480
ggtggttcag gtggtggtgg atctgctaaa ggtgaagaat tattcacagg tgttgtacct    540
attttagtag aattagacgg tgatgtaaac ggtcacaaat tttcagtttc tggtgaaggt    600
gaaggtgacg caacttatgg taaattaaca cttaaattca tttgtactac aggtaaatta    660
ccagtacctt ggccaacttt agttacaact tttacatacg gtgtacaatg tttcagtcgt    720
taccctgatc acatgaaaca acatgacttt ttcaaatctg ctatgccaga aggttatgtt    780
caagaacgta ctattttttt caagatgac ggtaattata aaacacgtgc tgaagtaaaa    840
tttgaaggtg atacttttagt taaccgtatt gaattaaaag gtattgactt caaagaagat    900
ggtaatattt taggtcacaa acttgaatat aactacaatt cacataacgt atatattatg    960
gcagacaaac aaaaaaatgg tattaaagta aactttaaaa ttcgtcataa tatcgaggat   1020
ggttctgtac aattagctga ccactatcaa caaaacacac caattggtga tggtcctgtt   1080
ttacttccag acaatcatta tttaagtact caatctgctt tatcaaaaga tcctaacgaa   1140
aaacgtgacc acatggtatt acttgaattt gttacagcag ctggtattac tcacgggtat   1200
ggatgaatta tacaaataaa tctaga                                        1226
```

<210> SEQ ID NO 9
<211> LENGTH: 717
<212> TYPE: DNA
<213> ORGANISM: Plasmodium sp.

<400> SEQUENCE: 9

```
catatgtcaa ttttctcttc aagtcgtgat caacaaacta cttcagttgc atctccatca     60
gtaccagtac cacctccaag tagttcaaca attggttctc cattattttg gattggtgta    120
ggtgttggtt tatcagcttt attctcttat gttacatcac catggcgtgt aacagaaaat    180
acaatttgta aatatggtta tttaattcaa atgtcaaatc actatgaatg taaatgtatt    240
gaaggttatg tattaattaa tgaagataca tgtggtaaaa agtagtatg tgataaagtt    300 gaaaattcat ttaaagcatg tgatgaatat gcatattgtt ttgacttagg taataaaaac    360
aatgaaaaac aaattaaatg tatgtgtcgt acagaatata cattaacagc aggtgtttgt    420
```

-continued

```
gttccaaatg tatgtcgtga caaagtttgt ggtaaaggta atgtattgt agatccagct      480 aattctttaa cacacacatg ttcttgtaat attggtacaa ttttaaacca aaacaaatta    540
tgtgatattc aaggtgatac accttgttct ttaaaatgtg cagaaaatga agtttgtaca    600
ttagaaggta actattatac atgtaaagaa gatcctaccg gtgaaaactt atactttcaa    660
ggttcaggtg gtggtggttc agattataaa gatgacgatg ataaaggtta atctaga       717
```

<210> SEQ ID NO 10
<211> LENGTH: 271
<212> TYPE: PRT
<213> ORGANISM: Plasmodium falciparum

<400> SEQUENCE: 10

```
Arg Val Leu Lys Tyr Pro His Asn Ile Leu Phe Thr Asn Leu Thr Asn
1               5                   10                  15

Asp Leu Phe Thr Tyr Leu Pro Lys Thr Tyr Asn Glu Ser Asn Phe Val
            20                  25                  30

Ser Asn Val Leu Glu Val Glu Leu Asn Asp Gly Glu Leu Phe Val Leu
        35                  40                  45

Ala Cys Glu Leu Ile Asn Lys Lys Cys Phe Gln Glu Gly Lys Glu Lys
    50                  55                  60

Ala Leu Tyr Lys Ser Asn Lys Ile Ile Tyr His Lys Asn Leu Thr Ile
65                  70                  75                  80

Phe Lys Ala Pro Phe Tyr Val Thr Ser Lys Asp Val Asn Thr Glu Cys
                85                  90                  95

Thr Cys Lys Phe Lys Asn Asn Asn Tyr Lys Ile Val Leu Lys Pro Lys
            100                 105                 110

Tyr Glu Lys Lys Val Ile His Gly Cys Asn Phe Ser Ser Asn Val Ser
        115                 120                 125

Ser Lys His Thr Phe Thr Asp Ser Leu Asp Ile Ser Leu Val Asp Asp
    130                 135                 140

Ser Ala His Ile Ser Cys Asn Val His Leu Ser Glu Pro Lys Tyr Asn
145                 150                 155                 160

His Leu Val Gly Leu Asn Cys Pro Gly Asp Ile Ile Pro Asp Cys Phe
                165                 170                 175

Phe Gln Val Tyr Gln Pro Glu Ser Glu Glu Leu Glu Pro Ser Asn Ile
            180                 185                 190

Val Tyr Leu Asp Ser Gln Ile Asn Ile Gly Asp Ile Glu Tyr Tyr Glu
        195                 200                 205

Asp Ala Glu Gly Asp Asp Lys Ile Lys Leu Phe Gly Ile Val Gly Ser
    210                 215                 220

Ile Pro Lys Thr Thr Ser Phe Thr Cys Ile Cys Lys Lys Asp Lys Lys
225                 230                 235                 240

Ser Ala Tyr Met Thr Val Thr Ile Asp Ser Ala Tyr Tyr Gly Phe Leu
                245                 250                 255

Ala Lys Thr Phe Ile Phe Leu Ile Val Ala Ile Leu Leu Tyr Ile
            260                 265                 270
```

<210> SEQ ID NO 11
<211> LENGTH: 813
<212> TYPE: DNA
<213> ORGANISM: Plasmodium sp.

<400> SEQUENCE: 11

```
cgtgtattaa aatacccaca taatatttta tttactaatt taactaacga tttatttaca    60
```

-continued

```
tatttaccta aaacatacaa cgaatctaat tttgtttcaa atgtattaga agtagaatta      120
aacgatggtg aattattcgt tttagcttgt gaattaatta ataaaaaatg tttccaagaa      180
ggtaaagaaa aagcattata caaaagtaac aaaattattt accacaaaaa cttaacaatt      240
ttcaaagcac cttttatgt tacatctaaa gatgtaaata cagaatgtac atgtaaattt       300
aaaaataaca attacaaaat tgttttaaaa ccaaatatg aaaaaaagt tattcatggt        360 tgtaatttct catctaatgt tagtagtaaa catacattca cagattcatt agatattagt     420
ttagttgacg attcagcaca tattagttgt aacgttcatt aagtgaacc taaatacaat     480 catttagttg gttaaattg tcctggtgat attattccag attgttttt tcaagtatat       540 caaccagaat ctgaagaatt agaaccaagt aatattgttt atttagattc tcaaattaac     600
attggtgaca ttgaatatta tgaagacgct gaaggtgacg ataaaattaa attattcggt    660
attgttggta gtattccaaa aacaacatca tttacatgta tttgtaaaaa agacaaaaaa    720
agtgcttaca tgacagttac tattgatagt gcatactacg gtttcttagc aaaaacattc     780
attttcttaa ttgtagctat tttattatac att                                  813
```

<210> SEQ ID NO 12
<211> LENGTH: 179
<212> TYPE: PRT
<213> ORGANISM: Plasmodium falciparum

<400> SEQUENCE: 12

```
Ala Lys Val Thr Val Asp Thr Val Cys Lys Arg Gly Phe Leu Ile Gln
1               5                   10                  15

Met Ser Gly His Leu Glu Cys Lys Cys Glu Asn Asp Leu Val Leu Val
            20                  25                  30

Asn Glu Glu Thr Cys Glu Glu Lys Val Leu Lys Cys Asp Glu Lys Thr
        35                  40                  45

Val Asn Lys Pro Cys Gly Asp Phe Ser Lys Cys Ile Lys Ile Asp Gly
    50                  55                  60

Asn Pro Val Ser Tyr Ala Cys Lys Cys Asn Leu Gly Tyr Asp Met Val
65                  70                  75                  80

Asn Asn Val Cys Ile Pro Asn Glu Cys Lys Asn Val Thr Cys Gly Asn
                85                  90                  95

Gly Lys Cys Ile Leu Asp Thr Ser Asn Pro Val Lys Thr Ala Val Cys
            100                 105                 110

Ser Cys Asn Ile Gly Lys Val Pro Asn Val Gln Asp Gln Asn Lys Cys
        115                 120                 125

Ser Lys Asp Gly Glu Thr Lys Cys Ser Leu Lys Cys Leu Lys Glu Asn
    130                 135                 140

Glu Thr Cys Lys Ala Val Asp Gly Ile Tyr Lys Cys Asp Cys Lys Asp
145                 150                 155                 160

Gly Phe Ile Ile Asp Asn Glu Ser Ser Ile Cys Thr Ala Phe Ser Ala
                165                 170                 175

Tyr Asn Ile
```

<210> SEQ ID NO 13
<211> LENGTH: 519
<212> TYPE: DNA
<213> ORGANISM: Plasmodium sp.

<400> SEQUENCE: 13

```
atggcaaaag ttacagttga tactgtatgt aaacgtggtt tcttaattca atgtcaggt       60
```

```
cacttagaat gtaaatgtga aaatgattta gtattagtaa atgaagaaac atgtgaagaa    120
aaagttttaa atgtgatga aaaaactgtt aataaaccat gtggtgattt ctcaaaatgt    180
attaaaattg atggtaaccc agtatcttat gcttgtaaat gtaatttagg ttacgacatg    240
gttaataatg tatgtattcc aaatgaatgt aaaaacgtaa cttgtggtaa tggtaaatgt    300
attttagata catctaatcc tgtaaaaact ggtgtttgtt cttgtaatat tggtaaagtt    360
ccaaacgtac aagatcaaaa caatgttcaa aagatggtg aaacaaaatg ttctttaaaa    420
tgtttaaaag aaaacgaaac atgtaaagct gttgatggta tttacaaatg tgattgtaaa    480
gatggtttca ttattgataa cgaatcatct atttgtaca                          519
```

<210> SEQ ID NO 14
<211> LENGTH: 594
<212> TYPE: DNA
<213> ORGANISM: Plasmodium sp.

<400> SEQUENCE: 14

```
atggcaaaag ttacagttga tactgtatgt aaacgtggtt tcttaattca atgtcaggt     60 cacttagaat gtaaatgtga aaatgattta gtattagtaa atgaagaaac atgtgaagaa    120
aaagttttaa atgtgatga aaaaactgtt aataaaccat gtggtgattt ctcaaaatgt    180
attaaaattg atggtaaccc agtatcttat gcttgtaaat gtaatttagg ttacgacatg    240
gttaataatg tatgtattcc aaatgaatgt aaaaacgtaa cttgtggtaa tggtaaatgt    300
attttagata catctaatcc tgtaaaaact ggtgtttgtt cttgtaatat tggtaaagtt    360
ccaaacgtac aagatcaaaa caatgttcaa aagatggtg aaacaaaatg ttctttaaaa    420
tgtttaaaag aaaacgaaac atgtaaagct gttgatggta tttacaaatg tgattgtaaa    480
gatggtttca ttattgataa cgaatcatct atttgtacaa ccggtgaaaa cttatacttt    540
caaggttcag gtggtggtgg ttcagattat aaagatgacg atgataaagg ttaa          594
```

<210> SEQ ID NO 15
<211> LENGTH: 156
<212> TYPE: PRT
<213> ORGANISM: Plasmodium yoelii nigeriensis
<400> SEQUENCE: 15

```
Val Thr Val Asp Thr Ile Cys Thr Asn Gly Lys Leu Ile Gln Met Thr
1               5                   10                  15

Ser His Leu Glu Cys Lys Cys Ile Asp Gly Tyr Gly Leu Lys Asn Glu
                20                  25                  30

Asn Thr Cys Glu Lys Ile Val Lys Cys Asp Lys Leu Asp Asp Ile Asn
            35                  40                  45

Lys Val Cys Gly Glu Tyr Ala Ile Cys Gly Asn Lys Gly Val Lys Gly
        50                  55                  60

Leu Glu Arg Ala Leu Val Cys Ser Cys Ile Asn Gly Tyr Gly Ser Ser
65                  70                  75                  80

Gln Asn Val Cys Lys Pro Leu Lys Cys Val Asn Tyr Asp Cys Pro Ser
                85                  90                  95

Gly Lys Cys Ile Ile Asp Pro Phe Asn Pro Asn Asn Val Thr Cys Ser
            100                 105                 110

Cys Asp Ile Gly Lys Ile Met Gln Asn Gly Lys Cys Thr Gly Val Gly
        115                 120                 125

Gln Ala Lys Cys Ala Leu Lys Cys Lys Ala Thr Glu Glu Cys Lys Leu
    130                 135                 140
```

```
Val Gly Lys Tyr Tyr Glu Cys Ile Ser Lys Ser Pro
145                 150                 155
```

<210> SEQ ID NO 16
<211> LENGTH: 474
<212> TYPE: DNA
<213> ORGANISM: Plasmodium sp.

<400> SEQUENCE: 16

```
atgcgtgtaa cagaaaatac aatttgtaaa tatggttatt taattcaaat gtcaaatcac    60
tatgaatgta atgtattga aggttatgta ttaattaatg aagatacatg tggtaaaaaa   120
gtagtatgtg ataaagttga aaattcattt aaagcatgtg atgaatatgc atattgtttt   180
gacttaggta ataaaaacaa tgaaaaacaa attaaatgta tgtgtcgtac agaatataca   240
ttaacagcag gtgtttgtgt tccaaatgta tgtcgtgaca agtttgtgg taaaggtaaa   300
tgtattgtag atccagctaa ttctttaaca cacacatgtt cttgtaatat tggtacaatt   360
ttaaaccaaa acaaattatg tgatattcaa ggtgatacac cttgttcttt aaaatgtgca   420
gaaaatgaag tttgtacatt agaaggtaac tattatacat gtaaagaaga tcct          474
```

<210> SEQ ID NO 17
<211> LENGTH: 549
<212> TYPE: DNA
<213> ORGANISM: Plasmodium sp.

<400> SEQUENCE: 17

```
atgcgtgtaa cagaaaatac aatttgtaaa tatggttatt taattcaaat gtcaaatcac    60
tatgaatgta atgtattga aggttatgta ttaattaatg aagatacatg tggtaaaaaa   120
gtagtatgtg ataaagttga aaattcattt aaagcatgtg atgaatatgc atattgtttt   180
gacttaggta ataaaaacaa tgaaaaacaa attaaatgta tgtgtcgtac agaatataca   240
ttaacagcag gtgtttgtgt tccaaatgta tgtcgtgaca agtttgtgg taaaggtaaa   300
tgtattgtag atccagctaa ttctttaaca cacacatgtt cttgtaatat tggtacaatt   360
ttaaaccaaa acaaattatg tgatattcaa ggtgatacac cttgttcttt aaaatgtgca   420
gaaaatgaag tttgtacatt agaaggtaac tattatacat gtaaagaaga tcctaccggt   480
gaaaacttat actttcaagg ttcaggtggt ggtggttcag attataaaga tgacgatgat   540
aaaggttaa                                                           549
```

<210> SEQ ID NO 18
<211> LENGTH: 157
<212> TYPE: PRT
<213> ORGANISM: Plasmodium falciparum

<400> SEQUENCE: 18

```
Arg Val Thr Glu Asn Thr Ile Cys Lys Tyr Gly Tyr Leu Ile Gln Met
1               5                   10                  15

Ser Asn His Tyr Glu Cys Lys Cys Ile Glu Gly Tyr Val Leu Ile Asn
                20                  25                  30

Glu Asp Thr Cys Gly Lys Lys Val Val Cys Asp Lys Val Glu Asn Ser
            35                  40                  45

Phe Lys Ala Cys Asp Glu Tyr Ala Tyr Cys Phe Asp Leu Gly Asn Lys
        50                  55                  60

Asn Asn Glu Lys Gln Ile Lys Cys Met Cys Arg Thr Glu Tyr Thr Leu
65                  70                  75                  80

Thr Ala Gly Val Cys Val Pro Asn Val Cys Arg Asp Lys Val Cys Gly
```

```
            85                  90                  95
Lys Gly Lys Cys Ile Val Asp Pro Ala Asn Ser Leu Thr His Thr Cys
            100                 105                 110

Ser Cys Asn Ile Gly Thr Ile Leu Asn Gln Asn Lys Leu Cys Asp Ile
            115                 120                 125

Gln Gly Asp Thr Pro Cys Ser Leu Lys Cys Ala Glu Asn Glu Val Cys
            130                 135                 140

Thr Leu Glu Gly Asn Tyr Tyr Thr Cys Lys Glu Asp Pro
145                 150                 155
```

<210> SEQ ID NO 19
<211> LENGTH: 302
<212> TYPE: PRT
<213> ORGANISM: Plasmodium sp.

<400> SEQUENCE: 19

```
Met Asp Tyr Lys Asp Asp Asp Lys Ser Gly Gly Gly Gly Ser Arg
1               5                   10                  15

Ser Gly Glu Asn Leu Tyr Phe Gln Gly Ser Gly Gly Gly Gly Ser Arg
                20                  25                  30

Val Leu Lys Tyr Pro His Asn Ile Leu Phe Thr Asn Leu Thr Asn Asp
                35                  40                  45

Leu Phe Thr Tyr Leu Pro Lys Thr Tyr Asn Glu Ser Asn Phe Val Ser
50                  55                  60

Asn Val Leu Glu Val Glu Leu Asn Asp Gly Glu Leu Phe Val Leu Ala
65                  70                  75                  80

Cys Glu Leu Ile Asn Lys Lys Cys Phe Gln Gly Lys Glu Lys Ala
                85                  90                  95

Leu Tyr Lys Ser Asn Lys Ile Ile Tyr His Lys Asn Leu Thr Ile Phe
                100                 105                 110

Lys Ala Pro Phe Tyr Val Thr Ser Lys Asp Val Asn Thr Glu Cys Thr
                115                 120                 125

Cys Lys Phe Lys Asn Asn Tyr Lys Ile Val Leu Lys Pro Lys Tyr
                130                 135                 140

Glu Lys Lys Val Ile His Gly Cys Asn Phe Ser Ser Asn Val Ser Ser
145                 150                 155                 160

Lys His Thr Phe Thr Asp Ser Leu Asp Ile Ser Leu Val Asp Asp Ser
                165                 170                 175

Ala His Ile Ser Cys Asn Val His Leu Ser Glu Pro Lys Tyr Asn His
                180                 185                 190

Leu Val Gly Leu Asn Cys Pro Gly Asp Ile Ile Pro Asp Cys Phe Phe
                195                 200                 205

Gln Val Tyr Gln Pro Glu Ser Glu Leu Glu Pro Ser Asn Ile Val
                210                 215                 220

Tyr Leu Asp Ser Gln Ile Asn Ile Gly Asp Ile Glu Tyr Tyr Glu Asp
225                 230                 235                 240

Ala Glu Gly Asp Asp Lys Ile Lys Leu Phe Gly Ile Val Gly Ser Ile
                245                 250                 255

Pro Lys Thr Thr Ser Phe Thr Cys Ile Cys Lys Lys Asp Lys Lys Ser
                260                 265                 270

Ala Tyr Met Thr Val Thr Ile Asp Ser Ala Tyr Tyr Gly Phe Leu Ala
                275                 280                 285

Lys Thr Phe Ile Phe Leu Ile Val Ala Ile Leu Leu Tyr Ile
                290                 295                 300
```

<210> SEQ ID NO 20
<211> LENGTH: 422
<212> TYPE: PRT
<213> ORGANISM: Plasmodium sp.

<400> SEQUENCE: 20

| Gly | Asn | Asn | Asp | Phe | Cys | Lys | Pro | Ser | Ser | Leu | Asn | Ser | Glu | Ile | Ser |
|---|---|---|---|---|---|---|---|---|---|---|---|---|---|---|---|
| 1 | | | | 5 | | | | | 10 | | | | | 15 | |

| Gly | Phe | Ile | Gly | Tyr | Lys | Cys | Asn | Phe | Ser | Asn | Glu | Gly | Val | His | Asn |
|---|---|---|---|---|---|---|---|---|---|---|---|---|---|---|---|
| | | | 20 | | | | | 25 | | | | | 30 | | |

| Leu | Lys | Pro | Asp | Met | Arg | Glu | Arg | Arg | Ser | Ile | Phe | Cys | Thr | Ile | His |
|---|---|---|---|---|---|---|---|---|---|---|---|---|---|---|---|
| | | 35 | | | | | 40 | | | | | 45 | | | |

| Ser | Tyr | Phe | Ile | Tyr | Asp | Lys | Ile | Arg | Leu | Ile | Ile | Pro | Lys | Lys | Ser |
|---|---|---|---|---|---|---|---|---|---|---|---|---|---|---|---|
| | 50 | | | | | 55 | | | | | 60 | | | | |

| Ser | Ser | Pro | Glu | Phe | Lys | Ile | Leu | Pro | Glu | Lys | Cys | Phe | Gln | Lys | Val |
|---|---|---|---|---|---|---|---|---|---|---|---|---|---|---|---|
| 65 | | | | | 70 | | | | | 75 | | | | | 80 |

| Tyr | Thr | Asp | Tyr | Glu | Asn | Arg | Val | Glu | Thr | Asp | Ile | Ser | Glu | Leu | Gly |
|---|---|---|---|---|---|---|---|---|---|---|---|---|---|---|---|
| | | | | 85 | | | | | 90 | | | | | 95 | |

| Leu | Ile | Glu | Tyr | Glu | Ile | Glu | Glu | Asn | Asp | Thr | Asn | Pro | Asn | Tyr | Asn |
|---|---|---|---|---|---|---|---|---|---|---|---|---|---|---|---|
| | | | 100 | | | | | 105 | | | | | 110 | | |

| Glu | Arg | Thr | Leu | Thr | Ile | Ser | Pro | Phe | Ser | Pro | Lys | Asp | Ile | Glu | Phe |
|---|---|---|---|---|---|---|---|---|---|---|---|---|---|---|---|
| | | 115 | | | | | 120 | | | | | 125 | | | |

| Phe | Cys | Phe | Cys | Asp | Asn | Thr | Glu | Lys | Val | Ile | Ser | Ser | Ile | Glu | Gly |
|---|---|---|---|---|---|---|---|---|---|---|---|---|---|---|---|
| | 130 | | | | | 135 | | | | | 140 | | | | |

| Arg | Ser | Ala | Met | Val | His | Val | Arg | Val | Leu | Lys | Tyr | Pro | His | Asn | Ile |
|---|---|---|---|---|---|---|---|---|---|---|---|---|---|---|---|
| 145 | | | | | 150 | | | | | 155 | | | | | 160 |

| Leu | Phe | Thr | Asn | Leu | Thr | Asn | Asp | Leu | Phe | Thr | Tyr | Leu | Pro | Lys | Thr |
|---|---|---|---|---|---|---|---|---|---|---|---|---|---|---|---|
| | | | | 165 | | | | | 170 | | | | | 175 | |

| Tyr | Asn | Glu | Ser | Asn | Phe | Val | Ser | Asn | Val | Leu | Glu | Val | Glu | Leu | Asn |
|---|---|---|---|---|---|---|---|---|---|---|---|---|---|---|---|
| | | | 180 | | | | | 185 | | | | | 190 | | |

| Asp | Gly | Glu | Leu | Phe | Val | Leu | Ala | Cys | Glu | Leu | Ile | Asn | Lys | Lys | Cys |
|---|---|---|---|---|---|---|---|---|---|---|---|---|---|---|---|
| | | 195 | | | | | 200 | | | | | 205 | | | |

| Phe | Gln | Glu | Gly | Lys | Glu | Lys | Ala | Leu | Tyr | Lys | Ser | Asn | Lys | Ile | Ile |
|---|---|---|---|---|---|---|---|---|---|---|---|---|---|---|---|
| | 210 | | | | | 215 | | | | | 220 | | | | |

| Tyr | His | Lys | Asn | Leu | Thr | Ile | Phe | Lys | Ala | Pro | Phe | Tyr | Val | Thr | Ser |
|---|---|---|---|---|---|---|---|---|---|---|---|---|---|---|---|
| 225 | | | | | 230 | | | | | 235 | | | | | 240 |

| Lys | Asp | Val | Asn | Thr | Glu | Cys | Thr | Cys | Lys | Phe | Lys | Asn | Asn | Asn | Tyr |
|---|---|---|---|---|---|---|---|---|---|---|---|---|---|---|---|
| | | | | 245 | | | | | 250 | | | | | 255 | |

| Lys | Ile | Val | Leu | Lys | Pro | Lys | Tyr | Glu | Lys | Lys | Val | Ile | His | Gly | Cys |
|---|---|---|---|---|---|---|---|---|---|---|---|---|---|---|---|
| | | | 260 | | | | | 265 | | | | | 270 | | |

| Asn | Phe | Ser | Ser | Asn | Val | Ser | Ser | Lys | His | Thr | Phe | Thr | Asp | Ser | Leu |
|---|---|---|---|---|---|---|---|---|---|---|---|---|---|---|---|
| | | 275 | | | | | 280 | | | | | 285 | | | |

| Asp | Ile | Ser | Leu | Val | Asp | Asp | Ser | Ala | His | Ile | Ser | Cys | Asn | Val | His |
|---|---|---|---|---|---|---|---|---|---|---|---|---|---|---|---|
| | 290 | | | | | 295 | | | | | 300 | | | | |

| Leu | Ser | Glu | Pro | Lys | Tyr | Asn | His | Leu | Val | Gly | Leu | Asn | Cys | Pro | Gly |
|---|---|---|---|---|---|---|---|---|---|---|---|---|---|---|---|
| 305 | | | | | 310 | | | | | 315 | | | | | 320 |

| Asp | Ile | Ile | Pro | Asp | Cys | Phe | Phe | Gln | Val | Tyr | Gln | Pro | Glu | Ser | Glu |
|---|---|---|---|---|---|---|---|---|---|---|---|---|---|---|---|
| | | | | 325 | | | | | 330 | | | | | 335 | |

| Glu | Leu | Glu | Pro | Ser | Asn | Ile | Val | Tyr | Leu | Asp | Ser | Gln | Ile | Asn | Ile |
|---|---|---|---|---|---|---|---|---|---|---|---|---|---|---|---|
| | | | 340 | | | | | 345 | | | | | 350 | | |

| Gly | Asp | Ile | Glu | Tyr | Tyr | Glu | Asp | Ala | Glu | Gly | Asp | Asp | Lys | Ile | Lys |
|---|---|---|---|---|---|---|---|---|---|---|---|---|---|---|---|
| | | 355 | | | | | 360 | | | | | 365 | | | |

| Leu | Phe | Gly | Ile | Val | Gly | Ser | Ile | Pro | Lys | Thr | Thr | Ser | Phe | Thr | Cys |
|---|---|---|---|---|---|---|---|---|---|---|---|---|---|---|---|
| | 370 | | | | | 375 | | | | | 380 | | | | |

```
Ile Cys Lys Lys Asp Lys Ser Ala Tyr Met Thr Val Thr Ile Asp
385                 390                 395                 400

Ser Ala Tyr Tyr Gly Phe Leu Ala Lys Thr Phe Ile Phe Leu Ile Val
                405                 410                 415

Ala Ile Leu Leu Tyr Ile
            420

<210> SEQ ID NO 21
<211> LENGTH: 448
<212> TYPE: PRT
<213> ORGANISM: Plasmodium sp.

<400> SEQUENCE: 21

Met Met Leu Tyr Ile Ser Ala Lys Lys Ala Gln Val Ala Phe Ile Leu
1               5                   10                  15

Tyr Ile Val Leu Val Leu Arg Ile Ile Ser Gly Asn Asn Asp Phe Cys
            20                  25                  30

Lys Pro Ser Ser Leu Asn Ser Glu Ile Ser Gly Phe Ile Gly Tyr Lys
            35                  40                  45

Cys Asn Phe Ser Asn Glu Gly Val His Asn Leu Lys Pro Asp Met Arg
50                  55                  60

Glu Arg Arg Ser Ile Phe Cys Thr Ile His Ser Tyr Phe Ile Tyr Asp
65                  70                  75                  80

Lys Ile Arg Leu Ile Ile Pro Lys Lys Ser Ser Pro Glu Phe Lys
                85                  90                  95

Ile Leu Pro Glu Lys Cys Phe Gln Lys Val Tyr Thr Asp Tyr Glu Asn
            100                 105                 110

Arg Val Glu Thr Asp Ile Ser Glu Leu Gly Leu Ile Glu Tyr Glu Ile
            115                 120                 125

Glu Glu Asn Asp Thr Asn Pro Asn Tyr Asn Glu Arg Thr Leu Thr Ile
130                 135                 140

Ser Pro Phe Ser Pro Lys Asp Ile Glu Phe Phe Cys Phe Cys Asp Asn
145                 150                 155                 160

Thr Glu Lys Val Ile Ser Ser Ile Glu Gly Arg Ser Ala Met Val His
                165                 170                 175

Val Arg Val Leu Lys Tyr Pro His Asn Ile Leu Phe Thr Asn Leu Thr
            180                 185                 190

Asn Asp Leu Phe Thr Tyr Leu Pro Lys Thr Tyr Asn Glu Ser Asn Phe
            195                 200                 205

Val Ser Asn Val Leu Glu Val Glu Leu Asn Asp Gly Glu Leu Phe Val
210                 215                 220

Leu Ala Cys Glu Leu Ile Asn Lys Lys Cys Phe Gln Glu Gly Lys Glu
225                 230                 235                 240

Lys Ala Leu Tyr Lys Ser Asn Lys Ile Ile Tyr His Lys Asn Leu Thr
                245                 250                 255

Ile Phe Lys Ala Pro Phe Tyr Val Thr Ser Lys Asp Val Asn Thr Glu
            260                 265                 270

Cys Thr Cys Lys Phe Lys Asn Asn Tyr Lys Ile Val Leu Lys Pro
            275                 280                 285

Lys Tyr Glu Lys Lys Val Ile His Gly Cys Asn Phe Ser Ser Asn Val
290                 295                 300

Ser Ser Lys His Thr Phe Thr Asp Ser Leu Asp Ile Ser Leu Val Asp
305                 310                 315                 320

Asp Ser Ala His Ile Ser Cys Asn Val His Leu Ser Glu Pro Lys Tyr
```

-continued

```
                    325                 330                 335
Asn His Leu Val Gly Leu Asn Cys Pro Gly Asp Ile Ile Pro Asp Cys
                340                 345                 350

Phe Phe Gln Val Tyr Gln Pro Glu Ser Glu Leu Glu Pro Ser Asn
            355                 360                 365

Ile Val Tyr Leu Asp Ser Gln Ile Asn Ile Gly Asp Ile Glu Tyr Tyr
370                 375                 380

Glu Asp Ala Glu Gly Asp Asp Lys Ile Lys Leu Phe Gly Ile Val Gly
385                 390                 395                 400

Ser Ile Pro Lys Thr Thr Ser Phe Thr Cys Ile Cys Lys Lys Asp Lys
                405                 410                 415

Lys Ser Ala Tyr Met Thr Val Thr Ile Asp Ser Ala Tyr Tyr Gly Phe
                420                 425                 430

Leu Ala Lys Thr Phe Ile Phe Leu Ile Val Ala Ile Leu Leu Tyr Ile
                435                 440                 445

<210> SEQ ID NO 22
<211> LENGTH: 426
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (63)..(64)
<223> OTHER INFORMATION: Any amino acid
<220> FEATURE:
<221> NAME/KEY: MOD_RES
<222> LOCATION: (79)..(79)
<223> OTHER INFORMATION: Any amino acid
<220> FEATURE:
<221> NAME/KEY: MOD_RES
<222> LOCATION: (85)..(85)
<223> OTHER INFORMATION: Any amino acid
<220> FEATURE:
<221> NAME/KEY: MOD_RES
<222> LOCATION: (88)..(88)
<223> OTHER INFORMATION: Any amino acid
<220> FEATURE:
<221> NAME/KEY: MOD_RES
<222> LOCATION: (102)..(102)
<223> OTHER INFORMATION: Any amino acid
<220> FEATURE:
<221> NAME/KEY: MOD_RES
<222> LOCATION: (110)..(110)
<223> OTHER INFORMATION: Any amino acid
<220> FEATURE:
<221> NAME/KEY: MOD_RES
<222> LOCATION: (117)..(117)
<223> OTHER INFORMATION: Ile or Leu
<220> FEATURE:
<221> NAME/KEY: MOD_RES
<222> LOCATION: (118)..(118)
<223> OTHER INFORMATION: Any amino acid
<220> FEATURE:
<221> NAME/KEY: MOD_RES
<222> LOCATION: (127)..(127)
<223> OTHER INFORMATION: Any amino acid
<220> FEATURE:
<221> NAME/KEY: MOD_RES
<222> LOCATION: (130)..(130)
<223> OTHER INFORMATION: Any amino acid
<220> FEATURE:
<221> NAME/KEY: MOD_RES
<222> LOCATION: (162)..(162)
<223> OTHER INFORMATION: Any amino acid
```

```
<220> FEATURE:
<221> NAME/KEY: MOD_RES
<222> LOCATION: (186)..(186)
<223> OTHER INFORMATION: Any amino acid
<220> FEATURE:
<221> NAME/KEY: MOD_RES
<222> LOCATION: (191)..(191)
<223> OTHER INFORMATION: Any amino acid
<220> FEATURE:
<221> NAME/KEY: MOD_RES
<222> LOCATION: (194)..(194)
<223> OTHER INFORMATION: Any amino acid
<220> FEATURE:
<221> NAME/KEY: MOD_RES
<222> LOCATION: (203)..(203)
<223> OTHER INFORMATION: Any amino acid
<220> FEATURE:
<221> NAME/KEY: MOD_RES
<222> LOCATION: (213)..(214)
<223> OTHER INFORMATION: Any amino acid
<220> FEATURE:
<221> NAME/KEY: MOD_RES
<222> LOCATION: (224)..(224)
<223> OTHER INFORMATION: Any amino acid
<220> FEATURE:
<221> NAME/KEY: MOD_RES
<222> LOCATION: (233)..(233)
<223> OTHER INFORMATION: Any amino acid
<220> FEATURE:
<221> NAME/KEY: MOD_RES
<222> LOCATION: (247)..(247)
<223> OTHER INFORMATION: Any amino acid
<220> FEATURE:
<221> NAME/KEY: MOD_RES
<222> LOCATION: (265)..(265)
<223> OTHER INFORMATION: Any amino acid
<220> FEATURE:
<221> NAME/KEY: MOD_RES
<222> LOCATION: (271)..(271)
<223> OTHER INFORMATION: Any amino acid
<220> FEATURE:
<221> NAME/KEY: MOD_RES
<222> LOCATION: (281)..(281)
<223> OTHER INFORMATION: Any amino acid
<220> FEATURE:
<221> NAME/KEY: MOD_RES
<222> LOCATION: (285)..(286)
<223> OTHER INFORMATION: Any amino acid
<220> FEATURE:
<221> NAME/KEY: MOD_RES
<222> LOCATION: (298)..(298)
<223> OTHER INFORMATION: Any amino acid
<220> FEATURE:
<221> NAME/KEY: MOD_RES
<222> LOCATION: (301)..(302)
<223> OTHER INFORMATION: Any amino acid
<220> FEATURE:
<221> NAME/KEY: MOD_RES
<222> LOCATION: (309)..(309)
<223> OTHER INFORMATION: Ile or Leu
<220> FEATURE:
<221> NAME/KEY: MOD_RES
<222> LOCATION: (334)..(334)
<223> OTHER INFORMATION: Any amino acid
<220> FEATURE:
<221> NAME/KEY: MOD_RES
<222> LOCATION: (336)..(336)
<223> OTHER INFORMATION: Any amino acid
<220> FEATURE:
<221> NAME/KEY: MOD_RES
<222> LOCATION: (338)..(339)
<223> OTHER INFORMATION: Any amino acid
<220> FEATURE:
<221> NAME/KEY: MOD_RES
<222> LOCATION: (343)..(344)
<223> OTHER INFORMATION: Any amino acid
<220> FEATURE:
<221> NAME/KEY: MOD_RES
<222> LOCATION: (348)..(348)
```

```
<223> OTHER INFORMATION: Any amino acid
<220> FEATURE:
<221> NAME/KEY: MOD_RES
<222> LOCATION: (372)..(372)
<223> OTHER INFORMATION: Any amino acid
<220> FEATURE:
<221> NAME/KEY: MOD_RES
<222> LOCATION: (375)..(375)
<223> OTHER INFORMATION: Any amino acid
<220> FEATURE:
<221> NAME/KEY: MOD_RES
<222> LOCATION: (379)..(379)
<223> OTHER INFORMATION: Any amino acid
<220> FEATURE:
<221> NAME/KEY: MOD_RES
<222> LOCATION: (382)..(384)
<223> OTHER INFORMATION: Any amino acid
<220> FEATURE:
<221> NAME/KEY: MOD_RES
<222> LOCATION: (389)..(389)
<223> OTHER INFORMATION: Any amino acid
<220> FEATURE:
<221> NAME/KEY: MOD_RES
<222> LOCATION: (392)..(392)
<223> OTHER INFORMATION: Any amino acid
<220> FEATURE:
<221> NAME/KEY: MOD_RES
<222> LOCATION: (395)..(395)
<223> OTHER INFORMATION: Any amino acid
<220> FEATURE:
<221> NAME/KEY: MOD_RES
<222> LOCATION: (398)..(398)
<223> OTHER INFORMATION: Any amino acid
<220> FEATURE:
<221> NAME/KEY: MOD_RES
<222> LOCATION: (401)..(401)
<223> OTHER INFORMATION: Any amino acid
<220> FEATURE:
<221> NAME/KEY: MOD_RES
<222> LOCATION: (409)..(409)
<223> OTHER INFORMATION: Any amino acid
<220> FEATURE:
<221> NAME/KEY: MOD_RES
<222> LOCATION: (412)..(412)
<223> OTHER INFORMATION: Any amino acid
<220> FEATURE:
<221> NAME/KEY: MOD_RES
<222> LOCATION: (418)..(418)
<223> OTHER INFORMATION: Any amino acid
<220> FEATURE:
<221> NAME/KEY: MOD_RES
<222> LOCATION: (420)..(420)
<223> OTHER INFORMATION: Any amino acid
<220> FEATURE:
<221> NAME/KEY: MOD_RES
<222> LOCATION: (423)..(425)
<223> OTHER INFORMATION: Any amino acid

<400> SEQUENCE: 22

Gly Lys Asn Glu Tyr Val Ser Pro Asp Glu Leu Asn Ile Lys Thr Ser
1               5                   10                  15

Gly Phe Leu Gly Tyr Lys Cys Asx Phe Ser Thr Glu Gly Xaa His Asn
                20                  25                  30

Leu Glu Pro Asp Ile Val Glu Arg Arg Ser Val Ile Cys Ser Ile Asn
            35                  40                  45

Ser Tyr Phe Ile Tyr Asp Lys Ile Lys Leu Ile Ile Pro Lys Xaa Xaa
        50                  55                  60

Asp Pro Lys Ser Lys Phe Lys Leu Leu Pro Glu Lys Cys Phe Xaa Lys
65                  70                  75                  80

Val Tyr Thr Asp Xaa Glu Gly Xaa Thr Glu Ile Pro Ile Glu Gln Thr
                85                  90                  95

Gly Leu Ile Glu Tyr Xaa Leu Glu Glu Asn Asp Thr Asn Xaa Asp Tyr
```

```
                100              105              110
Asn Glu Arg Ile Xaa Xaa Ile Ser Pro Phe Asn Asn Lys Asp Xaa Glu
            115              120              125

Phe Xaa Cys Ile Cys Asp Asn Thr Glu Gln Val Ile Ser His Ile Asp
130              135              140

Gly Arg Ser Ala Leu Val His Val Thr Val Leu Lys Tyr Pro His Lys
145              150              155              160

Ile Xaa Ser Val Asn Leu Thr Asp Gln Lys Tyr Pro Tyr Leu Pro Asp
                165              170              175

Ala Tyr Asn Lys Asn Asn Phe Ile Ser Xaa Lys Leu Glu Ile Xaa Leu
            180              185              190

Lys Xaa Gly Glu Leu Leu Val Leu Ala Cys Xaa Lys Ile Asp Asn Lys
    195              200              205

Cys Phe Gln Lys Xaa Xaa Glu Ser Lys Asn Gly Asp Leu Tyr Lys Xaa
210              215              220

Asn Lys Ile Ile Tyr His Lys Asx Xaa Ala Ile Phe Lys Ala Pro Ile
225              230              235              240

Tyr Val Lys Ser Asn Asp Xaa Thr Ala Glu Cys Thr Cys Lys Ile Asp
                245              250              255

Glu Thr Asn Ile Tyr Thr Leu Val Xaa Lys Pro Asp Tyr Asp Xaa Lys
            260              265              270

Val Ile His Gly Cys Asn Phe Ser Xaa Asp Leu Ser Xaa Xaa Thr Phe
        275              280              285

Thr Asn Asn Met Asx Leu Leu Lys Tyr Xaa Glu Asn Xaa Xaa Ile Asn
    290              295              300

Cys Asn Val Glu Xaa Ser Gln Pro Phe Tyr Asx His Leu Ile Gly Ile
305              310              315              320

Ser Cys Pro Gly Thr Ile Ile Pro Asp Cys Phe Phe Gln Xaa Tyr Xaa
                325              330              335

Pro Xaa Xaa Asn Glu Leu Xaa Xaa Ser Glu Ile Xaa Tyr Leu Asp Ser
            340              345              350

Gln Leu Asn Ile Gly Asn Ile Glu Tyr Tyr Glu Asp Ile His Gly Asn
        355              360              365

Asn Glu Ile Xaa Ile Phe Xaa Ile Val Gly Xaa Ile Pro Xaa Xaa Xaa
    370              375              380

Ser Phe Thr Cys Xaa Cys Lys Xaa Asp Lys Xaa Thr Gly Xaa Met Asn
385              390              395              400

Xaa Lys Ile Gly Ser Ala Tyr Tyr Xaa Phe Leu Xaa Lys Leu Phe Ile
            405              410              415

Ile Xaa Ile Xaa Leu Phe Xaa Xaa Xaa Leu
        420              425
```

<210> SEQ ID NO 23
<211> LENGTH: 274
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:

```
<221> NAME/KEY: MOD_RES
<222> LOCATION: (39)..(39)
<223> OTHER INFORMATION: Any amino acid
<220> FEATURE:
<221> NAME/KEY: MOD_RES
<222> LOCATION: (42)..(42)
<223> OTHER INFORMATION: Any amino acid
<220> FEATURE:
<221> NAME/KEY: MOD_RES
<222> LOCATION: (51)..(51)
<223> OTHER INFORMATION: Any amino acid
<220> FEATURE:
<221> NAME/KEY: MOD_RES
<222> LOCATION: (61)..(62)
<223> OTHER INFORMATION: Any amino acid
<220> FEATURE:
<221> NAME/KEY: MOD_RES
<222> LOCATION: (72)..(72)
<223> OTHER INFORMATION: Any amino acid
<220> FEATURE:
<221> NAME/KEY: MOD_RES
<222> LOCATION: (81)..(81)
<223> OTHER INFORMATION: Any amino acid
<220> FEATURE:
<221> NAME/KEY: MOD_RES
<222> LOCATION: (95)..(95)
<223> OTHER INFORMATION: Any amino acid
<220> FEATURE:
<221> NAME/KEY: MOD_RES
<222> LOCATION: (113)..(113)
<223> OTHER INFORMATION: Any amino acid
<220> FEATURE:
<221> NAME/KEY: MOD_RES
<222> LOCATION: (119)..(119)
<223> OTHER INFORMATION: Any amino acid
<220> FEATURE:
<221> NAME/KEY: MOD_RES
<222> LOCATION: (129)..(129)
<223> OTHER INFORMATION: Any amino acid
<220> FEATURE:
<221> NAME/KEY: MOD_RES
<222> LOCATION: (133)..(134)
<223> OTHER INFORMATION: Any amino acid
<220> FEATURE:
<221> NAME/KEY: MOD_RES
<222> LOCATION: (146)..(146)
<223> OTHER INFORMATION: Any amino acid
<220> FEATURE:
<221> NAME/KEY: MOD_RES
<222> LOCATION: (149)..(150)
<223> OTHER INFORMATION: Any amino acid
<220> FEATURE:
<221> NAME/KEY: MOD_RES
<222> LOCATION: (157)..(157)
<223> OTHER INFORMATION: Ile or Leu
<220> FEATURE:
<221> NAME/KEY: MOD_RES
<222> LOCATION: (182)..(182)
<223> OTHER INFORMATION: Any amino acid
<220> FEATURE:
<221> NAME/KEY: MOD_RES
<222> LOCATION: (184)..(184)
<223> OTHER INFORMATION: Any amino acid
<220> FEATURE:
<221> NAME/KEY: MOD_RES
<222> LOCATION: (186)..(187)
<223> OTHER INFORMATION: Any amino acid
<220> FEATURE:
<221> NAME/KEY: MOD_RES
<222> LOCATION: (191)..(192)
<223> OTHER INFORMATION: Any amino acid
<220> FEATURE:
<221> NAME/KEY: MOD_RES
<222> LOCATION: (196)..(196)
<223> OTHER INFORMATION: Any amino acid
<220> FEATURE:
<221> NAME/KEY: MOD_RES
<222> LOCATION: (220)..(220)
<223> OTHER INFORMATION: Any amino acid
```

```
<220> FEATURE:
<221> NAME/KEY: MOD_RES
<222> LOCATION: (223)..(223)
<223> OTHER INFORMATION: Any amino acid
<220> FEATURE:
<221> NAME/KEY: MOD_RES
<222> LOCATION: (227)..(227)
<223> OTHER INFORMATION: Any amino acid
<220> FEATURE:
<221> NAME/KEY: MOD_RES
<222> LOCATION: (230)..(232)
<223> OTHER INFORMATION: Any amino acid
<220> FEATURE:
<221> NAME/KEY: MOD_RES
<222> LOCATION: (237)..(237)
<223> OTHER INFORMATION: Any amino acid
<220> FEATURE:
<221> NAME/KEY: MOD_RES
<222> LOCATION: (240)..(240)
<223> OTHER INFORMATION: Any amino acid
<220> FEATURE:
<221> NAME/KEY: MOD_RES
<222> LOCATION: (243)..(243)
<223> OTHER INFORMATION: Any amino acid
<220> FEATURE:
<221> NAME/KEY: MOD_RES
<222> LOCATION: (246)..(246)
<223> OTHER INFORMATION: Any amino acid
<220> FEATURE:
<221> NAME/KEY: MOD_RES
<222> LOCATION: (249)..(249)
<223> OTHER INFORMATION: Any amino acid
<220> FEATURE:
<221> NAME/KEY: MOD_RES
<222> LOCATION: (257)..(257)
<223> OTHER INFORMATION: Any amino acid
<220> FEATURE:
<221> NAME/KEY: MOD_RES
<222> LOCATION: (260)..(260)
<223> OTHER INFORMATION: Any amino acid
<220> FEATURE:
<221> NAME/KEY: MOD_RES
<222> LOCATION: (266)..(266)
<223> OTHER INFORMATION: Any amino acid
<220> FEATURE:
<221> NAME/KEY: MOD_RES
<222> LOCATION: (268)..(268)
<223> OTHER INFORMATION: Any amino acid
<220> FEATURE:
<221> NAME/KEY: MOD_RES
<222> LOCATION: (271)..(273)
<223> OTHER INFORMATION: Any amino acid

<400> SEQUENCE: 23

Thr Val Leu Lys Tyr Pro His Lys Ile Xaa Ser Val Asn Leu Thr Asp
1               5                   10                  15

Gln Lys Tyr Pro Tyr Leu Pro Asp Ala Tyr Asn Lys Asn Asn Phe Ile
            20                  25                  30

Ser Xaa Lys Leu Glu Ile Xaa Leu Lys Xaa Gly Glu Leu Leu Val Leu
        35                  40                  45

Ala Cys Xaa Lys Ile Asp Asn Lys Cys Phe Gln Lys Xaa Xaa Glu Ser
50                  55                  60

Lys Asn Gly Asp Leu Tyr Lys Xaa Asn Lys Ile Ile Tyr His Lys Asx
65                  70                  75                  80

Xaa Ala Ile Phe Lys Ala Pro Ile Tyr Val Lys Ser Asn Asp Xaa Thr
                85                  90                  95

Ala Glu Cys Thr Cys Lys Ile Asp Glu Thr Asn Ile Tyr Thr Leu Val
            100                 105                 110

Xaa Lys Pro Asp Tyr Asp Xaa Lys Val Ile His Gly Cys Asn Phe Ser
        115                 120                 125
```

```
Xaa Asp Leu Ser Xaa Xaa Thr Phe Thr Asn Asn Met Asx Leu Leu Lys
    130             135                 140

Tyr Xaa Glu Asn Xaa Xaa Ile Asn Cys Asn Val Glu Xaa Ser Gln Pro
145             150                 155                 160

Phe Tyr Asx His Leu Ile Gly Ile Ser Cys Pro Gly Thr Ile Ile Pro
            165                 170                 175

Asp Cys Phe Phe Gln Xaa Tyr Xaa Pro Xaa Xaa Asn Glu Leu Xaa Xaa
            180             185                 190

Ser Glu Ile Xaa Tyr Leu Asp Ser Gln Leu Asn Ile Gly Asn Ile Glu
            195             200                 205

Tyr Tyr Glu Asp Ile His Gly Asn Asn Glu Ile Xaa Ile Phe Xaa Ile
210             215                 220

Val Gly Xaa Ile Pro Xaa Xaa Xaa Ser Phe Thr Cys Xaa Cys Lys Xaa
225             230                 235                 240

Asp Lys Xaa Thr Gly Xaa Met Asn Xaa Lys Ile Gly Ser Ala Tyr Tyr
            245                 250                 255

Xaa Phe Leu Xaa Lys Leu Phe Ile Ile Xaa Ile Xaa Leu Phe Xaa Xaa
            260                 265                 270

Xaa Leu
```

<210> SEQ ID NO 24
<211> LENGTH: 426
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (88)..(88)
<223> OTHER INFORMATION: Any amino acid
<220> FEATURE:
<221> NAME/KEY: MOD_RES
<222> LOCATION: (110)..(110)
<223> OTHER INFORMATION: Any amino acid
<220> FEATURE:
<221> NAME/KEY: MOD_RES
<222> LOCATION: (247)..(247)
<223> OTHER INFORMATION: Any amino acid
<220> FEATURE:
<221> NAME/KEY: MOD_RES
<222> LOCATION: (281)..(281)
<223> OTHER INFORMATION: Any amino acid

<400> SEQUENCE: 24

```
Gly Lys Asn Glu Tyr Val Ser Pro Asp Glu Leu Asn Ile Lys Thr Ser
1               5                   10                  15

Gly Phe Leu Gly Tyr Lys Cys Asp Phe Ser Thr Glu Gly Ile His Asn
            20                  25                  30

Leu Glu Pro Asp Ile Val Glu Arg Arg Ser Val Ile Cys Ser Ile Asn
            35                  40                  45

Ser Tyr Phe Ile Tyr Asp Lys Ile Lys Leu Ile Pro Lys Gln Asp
    50                  55                  60

Asp Pro Lys Ser Lys Phe Lys Leu Leu Pro Glu Lys Cys Phe Ala Lys
65                  70                  75                  80

Val Tyr Thr Asp Ile Glu Gly Xaa Thr Glu Ile Pro Ile Glu Gln Thr
            85                  90                  95

Gly Leu Ile Glu Tyr Thr Leu Glu Glu Asn Asp Thr Asn Xaa Asp Tyr
            100                 105                 110

Asn Glu Arg Ile Ile Gln Ile Ser Pro Phe Asn Asn Lys Asp Val Glu
            115                 120                 125
```

```
Phe Tyr Cys Ile Cys Asp Asn Thr Glu Gln Val Ile Ser His Ile Asp
            130                 135                 140

Gly Arg Ser Ala Leu Val His Val Thr Val Leu Lys Tyr Pro His Lys
145                 150                 155                 160

Ile Ile Ser Val Asn Leu Thr Asp Gln Lys Tyr Pro Tyr Leu Pro Asp
                165                 170                 175

Ala Tyr Asn Lys Asn Asn Phe Ile Ser Tyr Lys Leu Glu Ile Gly Leu
            180                 185                 190

Lys Glu Gly Glu Leu Leu Val Leu Ala Cys Lys Gln Ile Asp Asn Lys
        195                 200                 205

Cys Phe Gln Lys Asn Asp Glu Ser Lys Asn Gly Asp Leu Tyr Lys Thr
    210                 215                 220

Asn Lys Ile Ile Tyr His Lys Asp Phe Ala Ile Phe Lys Ala Pro Ile
225                 230                 235                 240

Tyr Val Lys Ser Asn Asp Xaa Thr Ala Glu Cys Thr Cys Lys Ile Asp
                245                 250                 255

Glu Thr Asn Ile Tyr Thr Leu Val Val Lys Pro Asp Tyr Asp Glu Lys
            260                 265                 270

Val Ile His Gly Cys Asn Phe Ser Xaa Asp Leu Ser Ile Arg Thr Phe
        275                 280                 285

Thr Asn Asn Met Asn Leu Leu Lys Tyr Asn Glu Asn Thr Asp Ile Asn
    290                 295                 300

Cys Asn Val Glu Ile Ser Gln Pro Phe Tyr Asp His Leu Ile Gly Ile
305                 310                 315                 320

Ser Cys Pro Gly Thr Ile Ile Pro Asp Cys Phe Phe Gln Ile Tyr Lys
                325                 330                 335

Pro Leu Thr Asn Glu Leu Lys Ser Ser Glu Ile Thr Tyr Leu Asp Ser
            340                 345                 350

Gln Leu Asn Ile Gly Asn Ile Glu Tyr Tyr Glu Asp Ile His Gly Asn
        355                 360                 365

Asn Glu Ile Arg Ile Phe Ser Ile Val Gly Ala Ile Pro Gln Ser Ala
    370                 375                 380

Ser Phe Thr Cys Met Cys Lys Met Asp Lys Ile Thr Gly Phe Met Asn
385                 390                 395                 400

Val Lys Ile Gly Ser Ala Tyr Tyr Ala Phe Leu Ser Lys Leu Phe Ile
                405                 410                 415

Ile Phe Ile Pro Leu Phe Phe Met Trp Leu
            420                 425

<210> SEQ ID NO 25
<211> LENGTH: 274
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (95)..(95)
<223> OTHER INFORMATION: Any amino acid
<220> FEATURE:
<221> NAME/KEY: MOD_RES
<222> LOCATION: (129)..(129)
<223> OTHER INFORMATION: Any amino acid

<400> SEQUENCE: 25

Thr Val Leu Lys Tyr Pro His Lys Ile Ile Ser Val Asn Leu Thr Asp
1               5                   10                  15
```

```
Gln Lys Tyr Pro Tyr Leu Pro Asp Ala Tyr Asn Lys Asn Asn Phe Ile
            20                  25                  30

Ser Tyr Lys Leu Glu Ile Gly Leu Lys Glu Gly Glu Leu Leu Val Leu
        35                  40                  45

Ala Cys Lys Gln Ile Asp Asn Lys Cys Phe Gln Lys Asn Asp Glu Ser
    50                  55                  60

Lys Asn Gly Asp Leu Tyr Lys Thr Asn Lys Ile Ile Tyr His Lys Asp
65                  70                  75                  80

Phe Ala Ile Phe Lys Ala Pro Ile Tyr Val Lys Ser Asn Asp Xaa Thr
                85                  90                  95

Ala Glu Cys Thr Cys Lys Ile Asp Glu Thr Asn Ile Tyr Thr Leu Val
            100                 105                 110

Val Lys Pro Asp Tyr Asp Glu Lys Val Ile His Gly Cys Asn Phe Ser
        115                 120                 125

Xaa Asp Leu Ser Ile Arg Thr Phe Thr Asn Asn Met Asn Leu Leu Lys
    130                 135                 140

Tyr Asn Glu Asn Thr Asp Ile Asn Cys Asn Val Glu Ile Ser Gln Pro
145                 150                 155                 160

Phe Tyr Asp His Leu Ile Gly Ile Ser Cys Pro Gly Thr Ile Ile Pro
                165                 170                 175

Asp Cys Phe Phe Gln Ile Tyr Lys Pro Leu Thr Asn Glu Leu Lys Ser
            180                 185                 190

Ser Glu Ile Thr Tyr Leu Asp Ser Gln Leu Asn Ile Gly Asn Ile Glu
        195                 200                 205

Tyr Tyr Glu Asp Ile His Gly Asn Asn Glu Ile Arg Ile Phe Ser Ile
    210                 215                 220

Val Gly Ala Ile Pro Gln Ser Ala Ser Phe Thr Cys Met Cys Lys Met
225                 230                 235                 240

Asp Lys Ile Thr Gly Phe Met Asn Val Lys Ile Gly Ser Ala Tyr Tyr
                245                 250                 255

Ala Phe Leu Ser Lys Leu Phe Ile Ile Phe Ile Pro Leu Phe Phe Met
            260                 265                 270

Trp Leu

<210> SEQ ID NO 26
<211> LENGTH: 196
<212> TYPE: PRT
<213> ORGANISM: Plasmodium sp.

<400> SEQUENCE: 26

Met Ala Lys Val Thr Val Asp Thr Val Cys Lys Arg Gly Phe Leu Ile
1               5                   10                  15

Gln Met Ser Gly His Leu Glu Cys Lys Cys Glu Asn Asp Leu Val Leu
            20                  25                  30

Val Asn Glu Glu Thr Cys Glu Glu Lys Val Leu Lys Cys Asp Glu Lys
        35                  40                  45

Thr Val Asn Lys Pro Cys Gly Asp Phe Ser Lys Cys Ile Lys Ile Asp
    50                  55                  60

Gly Asn Pro Val Ser Tyr Ala Cys Lys Cys Asn Leu Gly Tyr Asp Met
65                  70                  75                  80

Val Asn Asn Val Cys Ile Pro Asn Glu Cys Lys Asn Val Thr Cys Gly
                85                  90                  95

Asn Gly Lys Cys Ile Leu Asp Thr Ser Asn Pro Val Lys Thr Gly Val
            100                 105                 110
```

```
Cys Ser Cys Asn Ile Gly Lys Val Pro Asn Val Gln Asp Gln Asn Cys
        115                 120                 125

Ser Lys Asp Gly Glu Thr Lys Cys Ser Leu Lys Cys Leu Lys Glu Asn
    130                 135                 140

Glu Thr Cys Lys Ala Val Asp Gly Ile Tyr Lys Cys Asp Cys Lys Asp
145                 150                 155                 160

Gly Phe Ile Ile Asp Asn Glu Ser Ser Ile Cys Thr Thr Gly Glu Asn
                165                 170                 175

Leu Tyr Phe Gln Gly Ser Gly Gly Gly Ser Asp Tyr Lys Asp Asp
            180                 185                 190

Asp Asp Lys Gly
        195

<210> SEQ ID NO 27
<211> LENGTH: 218
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (40)..(40)
<223> OTHER INFORMATION: Any amino acid
<220> FEATURE:
<221> NAME/KEY: MOD_RES
<222> LOCATION: (47)..(47)
<223> OTHER INFORMATION: Any amino acid
<220> FEATURE:
<221> NAME/KEY: MOD_RES
<222> LOCATION: (54)..(54)
<223> OTHER INFORMATION: Any amino acid
<220> FEATURE:
<221> NAME/KEY: MOD_RES
<222> LOCATION: (64)..(64)
<223> OTHER INFORMATION: Any amino acid
<220> FEATURE:
<221> NAME/KEY: MOD_RES
<222> LOCATION: (96)..(96)
<223> OTHER INFORMATION: Any amino acid
<220> FEATURE:
<221> NAME/KEY: MOD_RES
<222> LOCATION: (107)..(107)
<223> OTHER INFORMATION: Any amino acid
<220> FEATURE:
<221> NAME/KEY: MOD_RES
<222> LOCATION: (144)..(144)
<223> OTHER INFORMATION: Any amino acid
<220> FEATURE:
<221> NAME/KEY: MOD_RES
<222> LOCATION: (147)..(147)
<223> OTHER INFORMATION: Any amino acid
<220> FEATURE:
<221> NAME/KEY: MOD_RES
<222> LOCATION: (151)..(151)
<223> OTHER INFORMATION: Any amino acid
<220> FEATURE:
<221> NAME/KEY: MOD_RES
<222> LOCATION: (191)..(191)
<223> OTHER INFORMATION: Any amino acid
<220> FEATURE:
<221> NAME/KEY: MOD_RES
<222> LOCATION: (198)..(198)
<223> OTHER INFORMATION: Any amino acid
<220> FEATURE:
<221> NAME/KEY: MOD_RES
<222> LOCATION: (207)..(207)
<223> OTHER INFORMATION: Any amino acid
```

<400> SEQUENCE: 27

```
Met Asn Lys Leu Tyr Ser Leu Phe Leu Phe Leu Phe Ile Gln Leu Ser
1               5                   10                  15

Ile Lys Tyr Asn Asn Ala Lys Val Thr Val Asp Thr Val Cys Lys Xaa
            20                  25                  30

Gly Phe Leu Ile Gln Met Ser Xaa His Leu Glu Cys Lys Cys Xaa Asn
        35                  40                  45

Asp Leu Val Leu Val Xaa Glu Glu Thr Cys Glu Glu Lys Val Leu Xaa
    50                  55                  60

Cys Asp Glu Lys Thr Val Asn Lys Pro Cys Gly Asp Phe Ser Lys Cys
65                  70                  75                  80

Ile Lys Ile Asp Asp Gly Asn Pro Val Ser Tyr Ala Cys Lys Cys Xaa
                85                  90                  95

Leu Gly Tyr Asp Met Val Asn Asn Val Cys Xaa Pro Asn Glu Cys Lys
            100                 105                 110

Asn Val Thr Cys Gly Asn Gly Lys Cys Ile Leu Asp Thr Ser Asn Pro
            115                 120                 125

Val Lys Thr Gly Val Cys Ser Cys Asn Ile Gly Lys Val Pro Asn Xaa
        130                 135                 140

Glu Asp Xaa Asn Lys Cys Xaa Lys Asp Gly Glu Thr Lys Cys Ser Leu
145                 150                 155                 160

Lys Cys Leu Lys Glu Asn Glu Thr Cys Lys Ala Val Asp Gly Ile Tyr
                165                 170                 175

Lys Cys Asp Cys Lys Asp Gly Phe Ile Ile Asp Asn Glu Ser Xaa Ile
            180                 185                 190

Cys Thr Ala Phe Ser Xaa Tyr Asn Ile Leu Asn Leu Ser Ile Xaa Phe
        195                 200                 205

Ile Leu Phe Ser Val Cys Phe Phe Ile Met
    210                 215
```

<210> SEQ ID NO 28  
<211> LENGTH: 180  
<212> TYPE: PRT  
<213> ORGANISM: Artificial Sequence  
<220> FEATURE:  
<223> OTHER INFORMATION: Description of Artificial Sequence: Synthetic consensus sequence  
<220> FEATURE:  
<221> NAME/KEY: MOD_RES  
<222> LOCATION: (11)..(11)  
<223> OTHER INFORMATION: Any amino acid  
<220> FEATURE:  
<221> NAME/KEY: MOD_RES  
<222> LOCATION: (19)..(19)  
<223> OTHER INFORMATION: Any amino acid  
<220> FEATURE:  
<221> NAME/KEY: MOD_RES  
<222> LOCATION: (26)..(26)  
<223> OTHER INFORMATION: Any amino acid  
<220> FEATURE:  
<221> NAME/KEY: MOD_RES  
<222> LOCATION: (33)..(33)  
<223> OTHER INFORMATION: Any amino acid  
<220> FEATURE:  
<221> NAME/KEY: MOD_RES  
<222> LOCATION: (43)..(43)  
<223> OTHER INFORMATION: Any amino acid  
<220> FEATURE:  
<221> NAME/KEY: MOD_RES  
<222> LOCATION: (75)..(75)  
<223> OTHER INFORMATION: Any amino acid  
<220> FEATURE:  
<221> NAME/KEY: MOD_RES

```
<222> LOCATION: (86)..(86)
<223> OTHER INFORMATION: Any amino acid
<220> FEATURE:
<221> NAME/KEY: MOD_RES
<222> LOCATION: (123)..(123)
<223> OTHER INFORMATION: Any amino acid
<220> FEATURE:
<221> NAME/KEY: MOD_RES
<222> LOCATION: (126)..(126)
<223> OTHER INFORMATION: Any amino acid
<220> FEATURE:
<221> NAME/KEY: MOD_RES
<222> LOCATION: (130)..(130)
<223> OTHER INFORMATION: Any amino acid
<220> FEATURE:
<221> NAME/KEY: MOD_RES
<222> LOCATION: (170)..(170)
<223> OTHER INFORMATION: Any amino acid
<220> FEATURE:
<221> NAME/KEY: MOD_RES
<222> LOCATION: (177)..(177)
<223> OTHER INFORMATION: Any amino acid

<400> SEQUENCE: 28

Ala Lys Val Thr Val Asp Thr Val Cys Lys Xaa Gly Phe Leu Ile Gln
1               5                   10                  15

Met Ser Xaa His Leu Glu Cys Lys Cys Xaa Asn Asp Leu Val Leu Val
            20                  25                  30

Xaa Glu Glu Thr Cys Glu Glu Lys Val Leu Xaa Cys Asp Glu Lys Thr
        35                  40                  45

Val Asn Lys Pro Cys Gly Asp Phe Ser Lys Cys Ile Lys Ile Asp Asp
    50                  55                  60

Gly Asn Pro Val Ser Tyr Ala Cys Lys Cys Xaa Leu Gly Tyr Asp Met
65                  70                  75                  80

Val Asn Asn Val Cys Xaa Pro Asn Glu Cys Lys Asn Val Thr Cys Gly
                85                  90                  95

Asn Gly Lys Cys Ile Leu Asp Thr Ser Asn Pro Val Lys Thr Gly Val
            100                 105                 110

Cys Ser Cys Asn Ile Gly Lys Val Pro Asn Xaa Glu Asp Xaa Asn Lys
        115                 120                 125

Cys Xaa Lys Asp Gly Glu Thr Lys Cys Ser Leu Lys Cys Leu Lys Glu
    130                 135                 140

Asn Glu Thr Cys Lys Ala Val Asp Gly Ile Tyr Lys Cys Asp Cys Lys
145                 150                 155                 160

Asp Gly Phe Ile Ile Asp Asn Glu Ser Xaa Ile Cys Thr Ala Phe Ser
                165                 170                 175

Xaa Tyr Asn Ile
            180

<210> SEQ ID NO 29
<211> LENGTH: 182
<212> TYPE: PRT
<213> ORGANISM: Plasmodium sp.

<400> SEQUENCE: 29

Met Arg Val Thr Glu Asn Thr Ile Cys Lys Tyr Gly Tyr Leu Ile Gln
1               5                   10                  15

Met Ser Asn His Tyr Glu Cys Lys Cys Ile Glu Gly Tyr Val Leu Ile
            20                  25                  30

Asn Glu Asp Thr Cys Gly Lys Lys Val Val Cys Asp Lys Val Glu Asn
        35                  40                  45

Ser Phe Lys Ala Cys Asp Glu Tyr Ala Tyr Cys Phe Asp Leu Gly Asn
```

```
            50                  55                  60
Lys Asn Asn Glu Lys Gln Ile Lys Cys Met Cys Arg Thr Glu Tyr Thr
 65                  70                  75                  80

Leu Thr Ala Gly Val Cys Val Pro Asn Val Cys Arg Asp Lys Val Cys
                 85                  90                  95

Gly Lys Gly Lys Cys Ile Val Asp Pro Ala Asn Ser Leu Thr His Thr
                100                 105                 110

Cys Ser Cys Asn Ile Gly Thr Ile Leu Asn Gln Asn Lys Leu Cys Asp
                115                 120                 125

Ile Gln Gly Asp Thr Pro Cys Ser Leu Lys Cys Ala Glu Asn Glu Val
            130                 135                 140

Cys Thr Leu Glu Gly Asn Tyr Tyr Thr Cys Lys Glu Asp Pro Thr Gly
145                 150                 155                 160

Glu Asn Leu Tyr Phe Gln Gly Ser Gly Gly Gly Ser Asp Tyr Lys
                165                 170                 175

Asp Asp Asp Asp Lys Gly
            180

<210> SEQ ID NO 30
<211> LENGTH: 218
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (42)..(42)
<223> OTHER INFORMATION: Any amino acid
<220> FEATURE:
<221> NAME/KEY: MOD_RES
<222> LOCATION: (63)..(63)
<223> OTHER INFORMATION: Any amino acid
<220> FEATURE:
<221> NAME/KEY: MOD_RES
<222> LOCATION: (79)..(79)
<223> OTHER INFORMATION: Any amino acid
<220> FEATURE:
<221> NAME/KEY: MOD_RES
<222> LOCATION: (81)..(81)
<223> OTHER INFORMATION: Any amino acid
<220> FEATURE:
<221> NAME/KEY: MOD_RES
<222> LOCATION: (84)..(84)
<223> OTHER INFORMATION: Any amino acid
<220> FEATURE:
<221> NAME/KEY: MOD_RES
<222> LOCATION: (87)..(88)
<223> OTHER INFORMATION: Any amino acid
<220> FEATURE:
<221> NAME/KEY: MOD_RES
<222> LOCATION: (92)..(92)
<223> OTHER INFORMATION: Any amino acid
<220> FEATURE:
<221> NAME/KEY: MOD_RES
<222> LOCATION: (97)..(97)
<223> OTHER INFORMATION: Any amino acid
<220> FEATURE:
```

```
<221> NAME/KEY: MOD_RES
<222> LOCATION: (106)..(106)
<223> OTHER INFORMATION: Any amino acid
<220> FEATURE:
<221> NAME/KEY: MOD_RES
<222> LOCATION: (113)..(113)
<223> OTHER INFORMATION: Any amino acid
<220> FEATURE:
<221> NAME/KEY: MOD_RES
<222> LOCATION: (115)..(115)
<223> OTHER INFORMATION: Any amino acid
<220> FEATURE:
<221> NAME/KEY: MOD_RES
<222> LOCATION: (132)..(132)
<223> OTHER INFORMATION: Any amino acid
<220> FEATURE:
<221> NAME/KEY: MOD_RES
<222> LOCATION: (150)..(151)
<223> OTHER INFORMATION: Any amino acid
<220> FEATURE:
<221> NAME/KEY: MOD_RES
<222> LOCATION: (153)..(153)
<223> OTHER INFORMATION: Any amino acid
<220> FEATURE:
<221> NAME/KEY: MOD_RES
<222> LOCATION: (169)..(169)
<223> OTHER INFORMATION: Any amino acid
<220> FEATURE:
<221> NAME/KEY: MOD_RES
<222> LOCATION: (177)..(177)
<223> OTHER INFORMATION: Any amino acid
<220> FEATURE:
<221> NAME/KEY: MOD_RES
<222> LOCATION: (197)..(197)
<223> OTHER INFORMATION: Any amino acid
<220> FEATURE:
<221> NAME/KEY: MOD_RES
<222> LOCATION: (204)..(204)
<223> OTHER INFORMATION: Any amino acid
<220> FEATURE:
<221> NAME/KEY: MOD_RES
<222> LOCATION: (210)..(210)
<223> OTHER INFORMATION: Any amino acid
<220> FEATURE:
<221> NAME/KEY: MOD_RES
<222> LOCATION: (215)..(215)
<223> OTHER INFORMATION: Any amino acid
<220> FEATURE:
<221> NAME/KEY: MOD_RES
<222> LOCATION: (218)..(218)
<223> OTHER INFORMATION: Any amino acid

<400> SEQUENCE: 30

Met Asn Xaa Xaa Tyr Ser Phe Xaa Phe Leu Xaa Phe Ile Gln Leu Ala
1               5                   10                  15

Ile Arg Tyr Asn Asn Ala Lys Val Thr Val Asp Thr Ile Cys Lys Asn
            20                  25                  30

Gly Tyr Leu Ile Gln Met Ser Asn His Xaa Glu Cys Lys Cys Ile Glu
        35                  40                  45

Gly Tyr Val Leu Lys Asn Glu Asn Thr Cys Glu Lys Lys Val Xaa Cys
    50                  55                  60

Asp Lys Leu Glu Asn Ile Asn Lys Val Cys Gly Glu Tyr Ala Xaa Cys
65                  70                  75                  80

Xaa Asn Gln Xaa Asn Lys Xaa Xaa Glu Lys Ala Xaa Lys Cys Met Cys
                85                  90                  95

Xaa Asn Gly Tyr Thr Leu Ser Gln Gly Xaa Cys Lys Pro Asn Arg Cys
            100                 105                 110

Xaa Asn Xaa Val Cys Gly Lys Gly Lys Cys Ile Leu Asp Pro Ala Asn
        115                 120                 125

Pro Asn Asn Xaa Thr Cys Ser Cys Asn Ile Gly Thr Ile Leu Asn Gln
```

```
                130                 135                 140
Asn Gly Lys Cys Thr Xaa Xaa Gly Xaa Thr Lys Cys Ser Leu Lys Cys
145                 150                 155                 160

Lys Ala Asn Glu Glu Cys Lys Leu Xaa Gly Asn Tyr Tyr Glu Cys Val
                165                 170                 175

Xaa Lys Pro Ser Ser Pro Gly Thr Gly Asn Thr Val Asp Gln Thr Pro
            180                 185                 190

Thr Ser Tyr Ser Xaa Met Asn Gly Val Ser Ile Xaa Ser Ile Leu Ala
        195                 200                 205

Leu Xaa Val Ile Phe Ile Xaa Val Met Xaa
    210                 215
```

<210> SEQ ID NO 31
<211> LENGTH: 156
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (40)..(40)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (58)..(58)
<223> OTHER INFORMATION: Any amino acid
<220> FEATURE:
<221> NAME/KEY: MOD_RES
<222> LOCATION: (61)..(61)
<223> OTHER INFORMATION: Any amino acid
<220> FEATURE:
<221> NAME/KEY: MOD_RES
<222> LOCATION: (64)..(65)
<223> OTHER INFORMATION: Any amino acid
<220> FEATURE:
<221> NAME/KEY: MOD_RES
<222> LOCATION: (69)..(69)
<223> OTHER INFORMATION: Any amino acid
<220> FEATURE:
<221> NAME/KEY: MOD_RES
<222> LOCATION: (74)..(74)
<223> OTHER INFORMATION: Any amino acid
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (90)..(90)
<223> OTHER INFORMATION: Any amino acid
<220> FEATURE:
<221> NAME/KEY: MOD_RES
<222> LOCATION: (92)..(92)
<223> OTHER INFORMATION: Any amino acid
<220> FEATURE:
<221> NAME/KEY: MOD_RES
<222> LOCATION: (109)..(109)
<223> OTHER INFORMATION: Any amino acid
<220> FEATURE:
<221> NAME/KEY: MOD_RES
<222> LOCATION: (127)..(128)
<223> OTHER INFORMATION: Any amino acid
<220> FEATURE:
<221> NAME/KEY: MOD_RES
<222> LOCATION: (130)..(130)
<223> OTHER INFORMATION: Any amino acid
<220> FEATURE:
<221> NAME/KEY: MOD_RES
<222> LOCATION: (146)..(146)
<223> OTHER INFORMATION: Any amino acid
<220> FEATURE:
<221> NAME/KEY: MOD_RES
<222> LOCATION: (154)..(154)
<223> OTHER INFORMATION: Any amino acid

<400> SEQUENCE: 31

```
Val Thr Val Asp Thr Ile Cys Lys Asn Gly Tyr Leu Ile Gln Met Ser
1               5                   10                  15

Asn His Xaa Glu Cys Lys Cys Ile Glu Gly Tyr Val Leu Lys Asn Glu
            20                  25                  30

Asn Thr Cys Glu Lys Lys Val Xaa Cys Asp Lys Leu Glu Asn Ile Asn
        35                  40                  45

Lys Val Cys Gly Glu Tyr Ala Xaa Cys Xaa Asn Gln Xaa Asn Lys Xaa
    50                  55                  60

Xaa Glu Lys Ala Xaa Lys Cys Met Cys Xaa Asn Gly Tyr Thr Leu Ser
65                  70                  75                  80

Gln Gly Xaa Cys Lys Pro Asn Arg Cys Xaa Asn Xaa Val Cys Gly Lys
                85                  90                  95

Gly Lys Cys Ile Leu Asp Pro Ala Asn Pro Asn Asn Xaa Thr Cys Ser
            100                 105                 110

Cys Asn Ile Gly Thr Ile Leu Asn Gln Asn Gly Lys Cys Thr Xaa Xaa
        115                 120                 125

Gly Xaa Thr Lys Cys Ser Leu Lys Cys Lys Ala Asn Glu Glu Cys Lys
    130                 135                 140

Leu Xaa Gly Asn Tyr Tyr Glu Cys Val Xaa Lys Pro
145                 150                 155
```

<210> SEQ ID NO 32
<211> LENGTH: 309
<212> TYPE: DNA
<213> ORGANISM: Vibrio cholera

<400> SEQUENCE: 32

```
acaccacaaa atattactga tttatgtgca gaatatcaca atacacaaat tcacacatta      60
aatgataaaa ttttttcata tactgaatca ttagctggta aacgtgaaat ggctattatt    120
acattcaaaa acggtgctac atttcaagta gaagttcctg gttcacaaca cattgattct    180
caaaaaaaag ctattgaacg tatgaaagat acattagcta ttgcttattt aacagaagct    240
aaagtagaaa aattatgtgt ttggaataat aaaactcctc atgcaattgc agctatttca    300
atggcaaat                                                            309
```

<210> SEQ ID NO 33
<211> LENGTH: 103
<212> TYPE: PRT
<213> ORGANISM: Vibrio cholera

<400> SEQUENCE: 33

```
Thr Pro Gln Asn Ile Thr Asp Leu Cys Ala Glu Tyr His Asn Thr Gln
1               5                   10                  15

Ile His Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Thr Phe
        35                  40                  45
```

Gln Val Glu Val Pro Gly Ser Gln His Ile Asp Ser Gln Lys Lys Ala
            50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn
            100

<210> SEQ ID NO 34
<211> LENGTH: 1041
<212> TYPE: DNA
<213> ORGANISM: Plasmodium sp.

<400> SEQUENCE: 34
tatgtagatg aaaagaacg tcaaggtgaa atttatcctt tcggtgatga agaagaaaaa      60
gatgaaggtg gtgaatcatt cacttatgaa aaatcagaag ttgataaaac agatttattc    120
aaatttattg aaggtggtga aggtgatgat gtatataaag tagatggttc aaaagtatta    180
ttagatgatg atactatttc acgtgtttca aaaaaacata cagctcgtga tggtgaatat    240
ggtgaatatg gtgaagcagt tgaagatggt gaaaatgtaa ttaaaattat tcgttcagtt    300
ttacaatcag gtgctttacc ttcagtaggt gttgatgaat tagataaaat tgacttatct    360
tatgaaacaa cagaatcagg tgacacagca gtttcagaag actcatatga taaatatgct    420
tcaaataata ctaataaaga atatgtttgt gattttacag atcaattaaa accaactgaa    480
tcaggtccaa aagttaaaaa atgtgaagtt aaagttaatg aaccattaat taaagtaaaa    540
attatttgtc cattaaaagg ttcagttgaa aaattatatg ataatattga atatgtacct    600
aaaaaatcac cttatgttgt tttaactaaa gaagaaacaa aattaaaaga aaaattatta    660
tcaaaattaa tttatggttt attaatttca ccaacagtaa atgaaaaaga aaataatttt    720
aaagaaggtg taattgaatt tacattacca ccagtagttc ataaagcaac tgttttctat    780
ttcatttgtg ataattcaaa aactgaagat gataataaaa aagtaatcg tggtattgta    840 gaagtttatg ttgaacctta tggtaataaa attaatggtt gtgcattctt agatgaagat    900
gaagaagaag aaaaatatgg taatcaaatt gaagaagatg aacacaatga aaaattaaa    960 atgaaaactt ttttcacaca aaatatttat aaaaaaaata tatttatcc atgttatatg   1020 aaattatatt caggtgatat t                                             1041

<210> SEQ ID NO 35
<211> LENGTH: 347
<212> TYPE: PRT
<213> ORGANISM: Plasmodium sp.

<400> SEQUENCE: 35

Tyr Val Asp Glu Lys Glu Arg Gln Gly Glu Ile Tyr Pro Phe Gly Asp
1               5                   10                  15

Glu Glu Glu Lys Asp Glu Gly Gly Glu Ser Phe Thr Tyr Glu Lys Ser
                20                  25                  30

Glu Val Asp Lys Thr Asp Leu Phe Lys Phe Ile Glu Gly Gly Glu Gly
            35                  40                  45

Asp Asp Val Tyr Lys Val Asp Gly Ser Lys Val Leu Leu Asp Asp Asp
        50                  55                  60

Thr Ile Ser Arg Val Ser Lys Lys His Thr Ala Arg Asp Gly Glu Tyr
65                  70                  75                  80

```
Gly Glu Tyr Gly Glu Ala Val Glu Asp Gly Glu Asn Val Ile Lys Ile
                85                  90                  95

Ile Arg Ser Val Leu Gln Ser Gly Ala Leu Pro Ser Val Gly Val Asp
            100                 105                 110

Glu Leu Asp Lys Ile Asp Leu Ser Tyr Glu Thr Thr Glu Ser Gly Asp
        115                 120                 125

Thr Ala Val Ser Glu Asp Ser Tyr Asp Lys Tyr Ala Ser Asn Asn Thr
130                 135                 140

Asn Lys Glu Tyr Val Cys Asp Phe Thr Asp Gln Leu Lys Pro Thr Glu
145                 150                 155                 160

Ser Gly Pro Lys Val Lys Cys Glu Val Lys Val Asn Glu Pro Leu
                165                 170                 175

Ile Lys Val Lys Ile Ile Cys Pro Leu Lys Gly Ser Val Glu Lys Leu
            180                 185                 190

Tyr Asp Asn Ile Glu Tyr Val Pro Lys Lys Ser Pro Tyr Val Val Leu
        195                 200                 205

Thr Lys Glu Glu Thr Lys Leu Lys Glu Lys Leu Leu Ser Lys Leu Ile
    210                 215                 220

Tyr Gly Leu Leu Ile Ser Pro Thr Val Asn Glu Lys Glu Asn Phe
225                 230                 235                 240

Lys Glu Gly Val Ile Glu Phe Thr Leu Pro Pro Val Val His Lys Ala
                245                 250                 255

Thr Val Phe Tyr Phe Ile Cys Asp Asn Ser Lys Thr Glu Asp Asp Asn
            260                 265                 270

Lys Lys Gly Asn Arg Gly Ile Val Glu Val Tyr Val Glu Pro Tyr Gly
        275                 280                 285

Asn Lys Ile Asn Gly Cys Ala Phe Leu Asp Glu Asp Glu Glu Glu
290                 295                 300

Lys Tyr Gly Asn Gln Ile Glu Glu Asp Glu His Asn Glu Lys Ile Lys
305                 310                 315                 320

Met Lys Thr Phe Phe Thr Gln Asn Ile Tyr Lys Lys Asn Asn Ile Tyr
                325                 330                 335

Pro Cys Tyr Met Lys Leu Tyr Ser Gly Asp Ile
            340                 345

<210> SEQ ID NO 36
<211> LENGTH: 771
<212> TYPE: DNA
<213> ORGANISM: Plasmodium sp.

<400> SEQUENCE: 36
ttacctaaat acttattcga tttatcaggt aaaacatgta acaaattagg tgtatctctt      60
aacaaatggc gtaactcaga tggtaacttc tgtggttcat cagcaggtta ctgtttatct     120
gaaaacttat ttaaatacta ttacattcac aaaacatcag ttggtaatcg taaaccttca     180
aaatacaaaa ttaaaaacat ttacggttct gaaccacaaa ctaagtata tacatctgct      240 aaattaccaa actacttaaa agataaagtt gattctaaca acaataaatc atacgacatt     300
aatgatattg acaacaaaat tttctacaat gaaaatgcag cagctcattc acatttcatt     360
gattacaaat ataacggtaa tcatacagta gaaattaaat tcgaaacaaa tgctttagaa     420
gttcatgaaa ttcgtccagt atcttatggt acaattactc acattacaat tccaaaagat     480
tgttcatcta atcaaactaa ttctaaagaa tgtattttag ttgttcacac atggaacaac     540
aataaaacaa ttggtgctaa ttttcatgt catgtattat gtgttgataa atcaacacaa      600
```

```
caagtagcaa ctcacatttc acctatttct aaaattaatg ctcatattga tgctaataaa      660
aactatgcat tctatttcat tattaaattc ttaattaaca aaaaaattac atctaactgt      720
acagcaattt taaaagatgc tgatggtcgt gaatgttcaa aattatcatt t              771
```

<210> SEQ ID NO 37
<211> LENGTH: 257
<212> TYPE: PRT
<213> ORGANISM: Plasmodium sp.

<400> SEQUENCE: 37

```
Leu Pro Lys Tyr Leu Phe Asp Leu Ser Gly Lys Thr Cys Asn Lys Leu
1               5                   10                  15

Gly Val Ser Leu Asn Lys Trp Arg Asn Ser Asp Gly Asn Phe Cys Gly
            20                  25                  30

Ser Ser Ala Gly Tyr Cys Leu Ser Glu Asn Leu Phe Lys Tyr Tyr Tyr
        35                  40                  45

Ile His Lys Thr Ser Val Gly Asn Arg Lys Pro Ser Tyr Lys Ile
    50                  55                  60

Lys Asn Ile Tyr Gly Ser Glu Pro Gln Thr Lys Val Tyr Thr Ser Ala
65                  70                  75                  80

Lys Leu Pro Asn Tyr Leu Lys Asp Lys Val Asp Ser Asn Asn Lys
                85                  90                  95

Ser Tyr Asp Ile Asn Asp Ile Asp Asn Lys Ile Phe Tyr Asn Glu Asn
            100                 105                 110

Ala Ala Ala His Ser His Phe Ile Asp Tyr Lys Tyr Asn Gly Asn His
        115                 120                 125

Thr Val Glu Ile Lys Phe Glu Thr Asn Ala Leu Glu Val His Glu Ile
    130                 135                 140

Arg Pro Val Ser Tyr Gly Thr Ile Thr His Ile Thr Ile Pro Lys Asp
145                 150                 155                 160

Cys Ser Ser Asn Gln Thr Asn Ser Lys Glu Cys Ile Leu Val Val His
                165                 170                 175

Thr Trp Asn Asn Asn Lys Thr Ile Gly Ala Asn Phe Ser Cys His Val
            180                 185                 190

Leu Cys Val Asp Lys Ser Thr Gln Gln Val Ala Thr His Ile Ser Pro
        195                 200                 205

Ile Ser Lys Ile Asn Ala His Ile Asp Ala Asn Lys Asn Tyr Ala Phe
    210                 215                 220

Tyr Phe Ile Ile Lys Phe Leu Ile Asn Lys Lys Ile Thr Ser Asn Cys
225                 230                 235                 240

Thr Ala Ile Leu Lys Asp Ala Asp Gly Arg Glu Cys Ser Lys Leu Ser
                245                 250                 255

Phe
```

<210> SEQ ID NO 38
<211> LENGTH: 171
<212> TYPE: PRT
<213> ORGANISM: Plasmodium falciparum

<400> SEQUENCE: 38

```
Lys Val Thr Val Asp Thr Val Cys Lys Arg Gly Phe Leu Ile Gln Met
1               5                   10                  15

Ser Gly His Leu Glu Cys Lys Cys Glu Asn Asp Leu Val Leu Val Asn
            20                  25                  30
```

```
Glu Glu Thr Cys Glu Glu Lys Val Leu Lys Cys Asp Glu Lys Thr Val
             35                  40                  45

Asn Lys Pro Cys Gly Asp Phe Ser Lys Cys Ile Lys Ile Asp Gly Asn
 50                  55                  60

Pro Val Ser Tyr Ala Cys Lys Cys Asn Leu Gly Tyr Asp Met Val Asn
 65                  70                  75                  80

Asn Val Cys Ile Pro Asn Glu Cys Lys Asn Val Thr Cys Gly Asn Gly
                 85                  90                  95

Lys Cys Ile Leu Asp Thr Ser Asn Pro Val Lys Thr Ala Val Cys Ser
            100                 105                 110

Cys Asn Ile Gly Lys Val Pro Asn Val Gln Asp Gln Asn Lys Cys Ser
            115                 120                 125

Lys Asp Gly Glu Thr Lys Cys Ser Leu Lys Cys Leu Lys Glu Asn Glu
130                 135                 140

Thr Cys Lys Ala Val Asp Gly Ile Tyr Lys Cys Asp Cys Lys Asp Gly
145                 150                 155                 160

Phe Ile Ile Asp Asn Glu Ser Ser Ile Cys Thr
                165                 170

<210> SEQ ID NO 39
<211> LENGTH: 173
<212> TYPE: PRT
<213> ORGANISM: Plasmodium vivax

<400> SEQUENCE: 39

Ala Val Thr Val Asp Thr Ile Cys Lys Asn Gly Gln Leu Val Gln Met
 1               5                  10                  15

Ser Asn His Phe Lys Cys Met Cys Asn Glu Gly Leu Val His Leu Ser
                20                  25                  30

Glu Asn Thr Cys Glu Glu Lys Asn Glu Cys Lys Lys Glu Thr Leu Gly
             35                  40                  45

Lys Ala Cys Gly Glu Phe Gly Gln Cys Ile Glu Asn Pro Asp Pro Ala
 50                  55                  60

Gln Val Asn Met Tyr Lys Cys Gly Cys Ile Gln Gly Tyr Thr Leu Lys
 65                  70                  75                  80

Glu Asp Thr Cys Val Leu Asp Val Cys Gln Tyr Lys Asn Cys Gly Glu
                 85                  90                  95

Ser Gly Glu Cys Ile Val Glu Tyr Leu Ser Thr Lys Ser Ala Gly
            100                 105                 110

Cys Ser Cys Ala Ile Gly Lys Val Pro Asn Pro Glu Asp Glu Lys Lys
            115                 120                 125

Cys Thr Lys Thr Gly Glu Thr Ala Cys Gln Leu Lys Cys Asn Thr Asp
130                 135                 140

Asn Glu Val Cys Lys Asn Val Glu Gly Val Tyr Lys Cys Gln Cys Met
145                 150                 155                 160

Glu Gly Phe Thr Phe Asp Lys Glu Lys Asn Val Cys Leu
                165                 170

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
```

```
gattataaag atgatgatga caaa                                         24
```

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

```
gtgctaggta actaacgttt gattttt                                      27
```

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42

```
aatattactt ggttctaatt cttc                                         24
```

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

```
catggttgta atttctcatc                                              20
```

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44

```
gattctggtt gatatacttg                                              20
```

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45

```
agcaggtgct ggattcaaag                                              20
```

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46

```
cagctacagc agcaccacat                                              20
```

<210> SEQ ID NO 47
<211> LENGTH: 10
<212> TYPE: PRT
<213> ORGANISM: Plasmodium falciparum

<400> SEQUENCE: 47

Ile Leu Asp Thr Ser Asn Pro Val Lys Thr
1               5                   10

<210> SEQ ID NO 48
<211> LENGTH: 22
<212> TYPE: PRT
<213> ORGANISM: Plasmodium falciparum
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (22)..(22)
<223> OTHER INFORMATION: May or may not be present

<400> SEQUENCE: 48

Lys Tyr Pro His Asn Ile Leu Phe Thr Asn Leu Thr Asn Asp Leu Phe
1               5                   10                  15

Thr Tyr Leu Pro Lys Thr
            20

<210> SEQ ID NO 49
<211> LENGTH: 10
<212> TYPE: PRT
<213> ORGANISM: Plasmodium falciparum
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (10)..(10)
<223> OTHER INFORMATION: May or may not be present

<400> SEQUENCE: 49

Lys Ala Pro Phe Tyr Val Thr Ser Lys Asp
1               5                   10

<210> SEQ ID NO 50
<211> LENGTH: 12
<212> TYPE: PRT
<213> ORGANISM: Plasmodium falciparum
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (12)..(12)
<223> OTHER INFORMATION: May or may not be present

<400> SEQUENCE: 50

Lys Leu Phe Gly Ile Val Gly Ser Ile Pro Lys Thr
1               5                   10

<210> SEQ ID NO 51
<211> LENGTH: 172
<212> TYPE: PRT
<213> ORGANISM: Artificial Sequence
<220> FEATURE:
<223> OTHER INFORMATION: Description of Artificial Sequence: Synthetic

```
       polypeptide

<400> SEQUENCE: 51

Met Ala Lys Val Thr Val Asp Thr Val Cys Lys Arg Gly Phe Leu Ile
1               5                   10                  15

Gln Met Ser Gly His Leu Glu Cys Lys Cys Glu Asn Asp Leu Val Leu
            20                  25                  30

Val Asn Glu Glu Thr Cys Glu Glu Lys Val Ile Lys Cys Asp Glu Lys
        35                  40                  45

Thr Val Asn Lys Pro Cys Gly Asp Phe Ser Lys Cys Ile Lys Ile Asp
    50                  55                  60

Gly Asn Pro Val Ser Tyr Ala Cys Lys Cys Asn Leu Tyr Asp Met Val
65                  70                  75                  80

Asn Asn Val Cys Ile Pro Asn Glu Cys Lys Asn Val Thr Cys Gly Asn
                85                  90                  95

Gly Lys Cys Ile Leu Asp Thr Ser Asn Pro Val Lys Thr Gly Val Cys
            100                 105                 110

Ser Cys Asn Ile Gly Lys Val Pro Asn Val Gln Asp Gln Asn Lys Cys
        115                 120                 125

Ser Lys Asp Gly Glu Thr Lys Cys Ser Leu Lys Cys Leu Lys Glu Asn
    130                 135                 140

Glu Thr Cys Lys Ala Val Asp Gly Ile Tyr Lys Cys Asp Cys Lys Asp
145                 150                 155                 160

Gly Phe Ile Ile Asp Asn Glu Ser Ser Ile Cys Thr
                165                 170
```

ALGAL PRODUCED MALARIAL TRANSMISSION BLOCKING VACCINES

CROSS-REFERENCE TO RELATED APPLICATIONS

This application is a U.S. national phase under 35 U.S.C. §371 of International Appl. No. PCT/US2012/036010, filed on May 1, 2012, which claims the benefit of U.S. Provisional Application No. 61/493,911, filed on Jun. 6, 2011, both of which are hereby incorporated herein in their entirety for all purposes.

STATEMENT OF GOVERNMENTAL SUPPORT

This invention was made with government support under Grant No. GM068524 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 17, 2014, is named UCSDP021_SL.txt and is 82,271 bytes in size.

FIELD OF THE INVENTION

The present invention relates to the production of malaria transmission blocking vaccines in single-celled green algae, particularly algae of the genus *Chlamydomonas*, e.g., *Chlamydomonas reinhardtii*; the immunogenic *Plasmodium* polypeptides produced and compositions comprising them; and methods for preventing, ameliorating, reducing, delaying, treating and blocking the transmission of malaria by administration of immunogenic *Plasmodium* polypeptides produced in an algal host cell.

BACKGROUND OF THE INVENTION

Malaria is a widespread infectious disease leading to a million deaths annually. Human infections are caused by a protozoan parasite from the genus *Plasmodium* often resulting in debilitating illness commonly treated using drug-based therapies. However, an increase in drug resistant strains of *Plasmodium* has led to the need for new methods of treatment. Transmission blocking vaccines have been designed against antigens expressed during the lifecycle of the parasite. For use as vaccines, *Plasmodium* transmission blocking antigens need to be expressed at very large amounts and for a fraction of the cost of traditional vaccine proteins. The present invention demonstrates the use of algae as a suitable platform for the low cost, large-scale production of malarial vaccines. Fragments of three illustrative *Plasmodium falciparum* (Pfs) antigens were expressed: Pfs25, Pfs28, Pfs48/45, in the eukaryotic algal expression host *Chlamydomonas reinhardtii*. Animal studies have shown that immunization with these antigens results in the production of antibodies capable of blocking the transmission of malaria. Also, the bioproduction of this protein in common production hosts is difficult and often results in poor expression levels. The present invention is based, in part, on the generation of transgenic *C. reinhardtii* chloroplasts transformed with codon-optimized versions of the pfs25, pfs28, and pfs48/45 genes. The identities of these proteins have been confirmed using mass spectrometry proteomics. The production of immunogenic *Plasmodium* proteins in algae allows for the development of a cost effective transmission blocking vaccine to facilitate the eradication of malaria.

SUMMARY OF THE INVENTION

The present invention provides malarial transmission blocking *Plasmodium* polynucleotides for expression in algal host cells, particularly unicellular green algae cells, particularly *Chlamydomonas reinhardtii*. In various embodiments, the coding sequences of the *Plasmodium* polynucleotides are altered for improved expression in algal host cells. Further provided are methods for producing malarial transmission blocking in algal host cells, particularly unicellular green algae cells, particularly *Chlamydomonas reinhardtii*.

Accordingly, in one aspect, the invention provides polynucleotides comprising a nucleic acid sequence having at least about 60% sequence identity to SEQ ID NO: 11 or SEQ ID NO:1, for example, at least about 65%, 70%, 75%, 80%, 85%, 90%, 95%, 98% or 99% sequence identity to SEQ ID NO: 11 or SEQ ID NO:1, wherein the nucleic acid sequence encodes a *Plasmodium* surface protein P48/45, or an immunogenic fragment thereof. In some embodiments, the polynucleotide comprises a nucleic acid sequence of SEQ ID NO: 11 or SEQ ID NO:1. In various embodiments, the *Plasmodium* surface protein P48/45, or immunogenic fragment thereof, is expressed from the polynucleotide in an algal host cell is bound by a conformationally dependent antibody against P48/45, e.g., in the absence of denaturing and refolding.

In a further aspect, the invention provides polynucleotides comprising a nucleic acid sequence having at least about 60% sequence identity to SEQ ID NO:13 or SEQ ID NO:2, for example, at least about 65%, 70%, 75%, 80%, 85%, 90%, 95%, 98% or 99% sequence identity to SEQ ID NO:2, wherein the nucleic acid sequence encodes a *Plasmodium* surface protein P25, or immunogenic fragment thereof. In some embodiments, the polynucleotide comprises a nucleic acid sequence of SEQ ID NO:13 or SEQ ID NO:2. In various embodiments, the *Plasmodium* surface protein P25, or immunogenic fragment thereof, is expressed from the polynucleotide in an algal host cell is bound by a conformationally dependent antibody against P25, e.g., in the absence of denaturing and refolding.

In a further aspect, the invention provides polynucleotides comprising a nucleic acid sequence having at least about 60% sequence identity to SEQ ID NO:16 or SEQ ID NO:6, for example, at least about 65%, 70%, 75%, 80%, 85%, 90%, 95%, 98% or 99% sequence identity to SEQ ID NO:16 or SEQ ID NO:6, wherein the nucleic acid sequence encodes a *Plasmodium* surface protein P28, or immunogenic fragment thereof. In some embodiments, the polynucleotide comprises a nucleic acid sequence of SEQ ID NO:16 or SEQ ID NO:6. In various embodiments, the *Plasmodium* surface protein P28, or immunogenic fragment thereof, is expressed from the polynucleotide in an algal host cell is bound by a conformationally dependent antibody against P28, e.g., in the absence of denaturing and refolding.

In a further aspect, the invention provides polynucleotides comprising a nucleic acid sequence having at least about 60% sequence identity to SEQ ID NO: 34, for example, at least about 65%, 70%, 75%, 80%, 85%, 90%, 95%, 98% or 99% sequence identity to SEQ ID NO:34, wherein the nucleic acid sequence encodes a *Plasmodium* surface protein P230, or immunogenic fragment thereof. In some embodiments, the polynucleotide encodes amino acid residues 444-730 of *Plasmodium* surface protein P230. In some embodiments, the polynucleotide encodes a *Plasmodium* surface protein P230, or immunogenic fragment thereof, having at least about 60% sequence identity to SEQ ID NO:35, for example, at least about 65%, 70%, 75%, 80%, 85%, 90%, 95%, 98% or 99% sequence identity to SEQ ID NO: 35.

In a further aspect, the invention provides polynucleotides comprising a nucleic acid sequence having at least about 60% sequence identity to SEQ ID NO: 36, for example, at least about 65%, 70%, 75%, 80%, 85%, 90%, 95%, 98% or 99% sequence identity to SEQ ID NO:36, wherein the nucleic acid sequence encodes a *Plasmodium* surface protein HAP2, or immunogenic fragment thereof. In some embodiments, the polynucleotide encodes a *Plasmodium* surface protein HAP2, or immunogenic fragment thereof, having at least about 60% sequence identity to SEQ ID NO: 37, for example, at least about 65%, 70%, 75%, 80%, 85%, 90%, 95%, 98% or 99% sequence identity to SEQ ID NO:37.

With respect to the embodiments of the polynucleotides, in some embodiments, the *Plasmodium* surface protein is from *Plasmodium falciparum, Plasmodium vivax, Plasmodium ovale, Plasmodium malariae, Plasmodium chabaudi, Plasmodium berghei, Plasmodium knowlesi, Plasmodium reichenowi* or *Plasmodium yoelii*. In some embodiments, the *Plasmodium* surface protein is a *Plasmodium falciparum* surface protein.

In some embodiments, the nucleic acid sequence encoding the *Plasmodium* surface protein is operably linked to a nucleic acid sequence encoding on or more tags selected from the group consisting of an affinity tag, a purification tag, an immunogenicity tag, a delivery tag, a secretion signal peptide and a stability tag. For example, in some embodiments, the nucleic acid sequence is operably linked to a nucleic acid sequence encoding one or more tags selected from the group consisting of poly-His, Mistic, serum amyloid A (SAA), translocon at the inner envelope membrane of chloroplasts (Tic40), small ubiquitin modifier peptide (SUMO), Streptavidin-Binding Peptide (SBP), green fluorescent protein (GFP), FLAG, cholera toxin beta subunit (CTB), and heat-labile enterotoxin beta subunit (LTB). The nucleic acid sequences encoding the tags can be positioned at either the 5'-end or 3'-end of the coding sequence for the *Plasmodium* surface protein (e.g., such that the expressed tags are positioned at either the N-terminal end or the C-terminal end of the polypeptide). In some embodiments, the *Plasmodium* antigen comprises at least one EGF domain or EGF-like domain and does not comprise the signal peptide or transmembrane domain of the native or full-length peptide. In various embodiments, the nucleic acid sequence is operably linked to a nucleic acid sequence encoding a cholera toxin beta subunit (CTB). In some embodiments, the nucleic acid sequence encoding a cholera toxin beta subunit (CTB) has at least 60% sequence identity, for example, at least 65%, 70%, 75%, 80%, 85%, 90%, 95%, 98% or 99% sequence identity to SEQ ID NO:32. In some embodiments, the nucleic acid sequence encoding a cholera toxin beta subunit (CTB) has a nucleic acid sequence of SEQ ID NO:32.

In a related aspect, the invention provides expression cassettes comprising the polynucleotides described above and herein, wherein the nucleic acid encoding the *Plasmodium* surface protein is operably linked to a promoter that promotes expression in an algal host cell. For example, in some embodiments, the promoter is selected from the group consisting of psbA and psbD.

In a further aspect, the invention provides expression cassettes comprising a promoter that drives expression of a coding sequence in an algal host cell operably linked to a nucleic acid sequence coding for one or more *Plasmodium* polypeptides. In various embodiments, the nucleic acid sequence encodes one or more *Plasmodium* polypeptides selected from the group consisting of calcium-dependent protein kinase 4 (CDPK4), Hapless 2 (HAP2), MAPK-2, MDV 1/Peg3, P47, P48/45, P230, PKG, AP2-0, DOZI, HMGP2, Nek-4, CelTOS, CDPK3, Chitinase, CTRP, IMC1b, MAOP, P25, P28, SOAP, Cap380, CSP, ECP1, IMC1a, LAP1/CCp3/SR, LAP2/CCp1, LAP3/CCp5, LAP4/CCp2, LAPS/FNPA, LAP6/CCp4, transglutaminase, CSP, CRMP1, CRMP2, MAEBL, TRAP, and UOS3/TREP/S6. In some embodiments, the nucleic acid sequence encodes one or more *Plasmodium* surface proteins, e.g., expressed on the surface of a gamete, zygote, ookinete, oocyst or sporozoite. In some embodiments, the nucleic acid sequence encodes one or more *Plasmodium* polypeptides selected from the group consisting of P48/45, P25, P28, P230 and HAP2. The nucleic acid sequence may encode polypeptide fragments and/or fusions. For example, in various embodiments, the *Plasmodium* antigen comprises at least one EGF domain or EGF-like domain and does not comprise the signal peptide or transmembrane domain of the native or full-length peptide. In some embodiments, the nucleic acid encodes amino acid residues 22-193 of P25 and does not comprise the signal peptide or transmembrane domain of the native or full-length P25. In some embodiments, the nucleic acid encodes a fragment of P25 no longer than amino acid residues 22-193 of P25. In some embodiments, the nucleic acid encodes amino acid residues 23-179 or 24-179 of P28 and does not comprise the signal peptide or transmembrane domain of the native or full-length P28. In some embodiments, the nucleic acid encodes a fragment of P28 no longer than amino acid residues 23-179 or 24-179 of P28. In some embodiments, the nucleic acid encodes amino acid residues 178-448 of P48/45 and does not comprise the signal peptide or transmembrane domain of the native or full-length P48/45. In some embodiments, the nucleic acid encodes a fragment of P48/45 no longer than amino acid residues 178-448 of P48/45.

With respect to embodiments of the expression cassettes, in some embodiments, the nucleic acid sequence encodes one or more *Plasmodium* polypeptides from *Plasmodium falciparum, Plasmodium vivax, Plasmodium ovale, Plasmodium malariae, Plasmodium chabaudi, Plasmodium berghei, Plasmodium knowlesi, Plasmodium reichenowi* or *Plasmodium yoelii*.

In some embodiments, the nucleic acid sequence encodes *Plasmodium* surface protein P48/45, or immunogenic fragment thereof, having at least about 60% sequence identity to SEQ ID NO: 11 or SEQ ID NO:1, for example, at least about 65%, 70%, 75%, 80%, 85%, 90%, 95%, 98% or 99% sequence identity to SEQ ID NO:11 or SEQ ID NO:1. In some embodiments, the nucleic acid sequence encodes *Plasmodium* surface protein P48/45 of SEQ ID NO: 11 or SEQ ID NO:1.

In some embodiments, the nucleic acid sequence encodes *Plasmodium* surface protein P48/45 residues 178-448 having at least about 60% sequence identity to SEQ ID NO:10, SEQ ID NO:23 or SEQ ID NO:25, for example, at least about 65%, 70%, 75%, 80%, 85%, 90%, 95%, 98% or 99% sequence identity to SEQ ID NO:10, SEQ ID NO:23 or SEQ ID NO:25. In some embodiments, the nucleic acid sequence encodes *Plasmodium* surface protein P48/45 residues 178-448 having 100% sequence identity to SEQ ID NO:10, SEQ ID NO:23 or SEQ ID NO:25. In various embodiments, the nucleic acid sequence encoding *Plasmodium* surface protein P48/45 residues 178-448 does not encode a signal peptide or transmembrane domain from the native or full-length P48/45 protein.

In some embodiments, the nucleic acid sequence encodes *Plasmodium* surface protein P25 and has at least about 60% sequence identity to SEQ ID NO:13 or SEQ ID NO:2, for example, at least about 65%, 70%, 75%, 80%, 85%, 90%, 95%, 98% or 99% sequence identity to SEQ ID NO: 13 or SEQ ID NO:2. In some embodiments, the nucleic acid sequence encodes *Plasmodium* surface protein P25 of SEQ ID NO: 13 or SEQ ID NO:2.

In some embodiments, the nucleic acid sequence encodes a *Plasmodium* surface protein P25 residues 22-193 having at least about 60% sequence identity to SEQ ID NO:12, SEQ ID NO:28, SEQ ID NO:38 and/or SEQ ID NO:39, for example, at least about 65%, 70%, 75%, 80%, 85%, 90%, 95%, 98% or 99% sequence identity to SEQ ID NO:12, SEQ ID NO:28, SEQ ID NO:38 and/or SEQ ID NO:39. In some embodiments, the nucleic acid sequence encodes *Plasmodium* surface protein P25 residues 22-193 having 100% sequence identity to SEQ ID NO:12, SEQ ID NO:28, SEQ ID NO:38 and/or SEQ ID NO:39. In various embodiments, the nucleic acid sequence encoding *Plasmodium* surface protein P25 residues 22-193 does not encode a signal peptide or transmembrane domain from the native or full-length P25 protein.

In some embodiments, the nucleic acid sequence encodes *Plasmodium* surface protein P28 and has at least about 60% sequence identity to SEQ ID NO: 16 or SEQ ID NO:6, for example, at least about 65%, 70%, 75%, 80%, 85%, 90%, 95%, 98% or 99% sequence identity to SEQ ID NO:16 or SEQ ID NO:6. In some embodiments, the nucleic acid sequence encodes *Plasmodium* surface protein P28 of SEQ ID NO:16 or SEQ ID NO:6.

In some embodiments, the nucleic acid sequence encodes *Plasmodium* surface protein P28 residues 23-179 or 24-179 having at least about 60% sequence identity to SEQ ID NO:15, SEQ ID NO:18 or SEQ ID NO:31, for example, at least about 65%, 70%, 75%, 80%, 85%, 90%, 95%, 98% or 99% sequence identity to SEQ ID NO:15, SEQ ID NO:18 or SEQ ID NO:31. In some embodiments, the nucleic acid sequence encodes *Plasmodium* surface protein P28 residues 23-179 or 24-179 having 100% sequence identity to SEQ ID NO:15, SEQ ID NO:18 or SEQ ID NO:31. In various embodiments, the nucleic acid sequence encoding *Plasmodium* surface protein P28 residues 23-179 or 24-179 does not encode a signal peptide or transmembrane domain from the native or full-length P28 protein.

In some embodiments, the nucleic acid sequence encodes *Plasmodium* surface protein P230, or immunogenic fragment thereof, and has at least about 60% sequence identity to SEQ ID NO: 34, for example, at least about 65%, 70%, 75%, 80%, 85%, 90%, 95%, 98%, 99% or 100% sequence identity to SEQ ID NO:34. In some embodiments, the nucleic acid sequence encodes amino acid residues 444-730 of *Plasmodium* surface protein P230. In some embodiments, the nucleic acid sequence encodes a *Plasmodium* surface protein P230, or immunogenic fragment thereof, having at least about 60% sequence identity to SEQ ID NO: 35, for example, at least about 65%, 70%, 75%, 80%, 85%, 90%, 95%, 98%, 99% or 100% sequence identity to SEQ ID NO:35. In various embodiments, the nucleic acid sequence encoding *Plasmodium* surface protein P230 residues 444-730 does not encode a signal peptide or transmembrane domain from the native or full-length P230 protein.

In some embodiments, the nucleic acid sequence encodes *Plasmodium* surface protein HAP2, or immunogenic fragment thereof, and has at least about 60% sequence identity to SEQ ID NO: 36, for example, at least about 65%, 70%, 75%, 80%, 85%, 90%, 95%, 98% or 100% sequence identity to SEQ ID NO:36. In some embodiments, the nucleic acid sequence encodes a *Plasmodium* surface protein HAP2, or immunogenic fragment thereof, having at least about 60% sequence identity to SEQ ID NO: 37, for example, at least about 65%, 70%, 75%, 80%, 85%, 90%, 95%, 98%, 99% or 100% sequence identity to SEQ ID NO:37. In various embodiments, the nucleic acid sequence encoding *Plasmodium* surface protein HAP2 does not encode a signal peptide or transmembrane domain from the native or full-length HAP2 protein.

In some embodiments, the promoter is selected from the group consisting of psbA and psbD.

In some embodiments, the nucleic acid sequence is operably linked to a nucleic acid sequence encoding one or more tags selected from the group consisting of an affinity tag, a purification tag, an immunogenicity tag, a delivery tag, a secretion signal peptide and a stability tag. For example, in various embodiments, the nucleic acid sequence is operably linked to a nucleic acid sequence encoding one or more tags selected from the group consisting of poly-His, Mistic, serum amyloid A (SAA), Tic40, small ubiquitin modifier peptide (SUMO), Streptavidin-Binding Peptide (SBP), green fluorescent protein (GFP), FLAG, cholera toxin beta subunit (CTB), and heat-labile enterotoxin beta subunit (LTB). In various embodiments, the nucleic acid sequence is operably linked to a nucleic acid sequence encoding a cholera toxin beta subunit (CTB). In some embodiments, the nucleic acid sequence encoding a cholera toxin beta subunit (CTB) has at least 60% sequence identity, for example, at least 65%, 70%, 75%, 80%, 85%, 90%, 95%, 98%, 99% or 100% sequence identity to SEQ ID NO:32. In some embodiments, the nucleic acid sequence encoding a cholera toxin beta subunit (CTB) has a nucleic acid sequence of SEQ ID NO:32.

In another aspect, the invention provides methods of producing a vaccine that interferes with or prevents the transmission of *Plasmodium* in a mammalian subject, comprising expressing a nucleic acid sequence encoding at least one epitope of an antigen of a parasite of the genus *Plasmodium* in an algal host cell, for example, a unicellular green algae host cell, for example, a *Chlamydomonas* host cell, for example, a *Chlamydomonas reinhardtii* host cell.

With respect to embodiments of the methods, in some embodiments, the *Plasmodium* is *Plasmodium falciparum*, *Plasmodium vivax*, *Plasmodium ovale*, *Plasmodium malariae*, *Plasmodium chabaudi*, *Plasmodium berghei*, *Plasmodium knowlesi*, *Plasmodium reichenowi* or *Plasmodium yoelii*.

In a further aspect, the invention provides algal host cells comprising the polynucleotides and/or expression cassettes described herein integrated into the chloroplast genome. In some embodiments, the algal cell is a *Chlamydomonas* cell. In some embodiments, the algal cell is a *Chlamydomonas reinhardtii* cell.

With respect to the embodiments of the methods for producing a transmission blocking vaccine, in some embodiments, the one or more *Plasmodium* polypeptides are selected from the group consisting of CDPK4, HAP2, MAPK-2, MDV 1/Peg3, P47, P48/45, P230, PKG, AP2-0, DOZI, HMGP2, Nek-4, CelTOS, CDPK3, Chitinase, CTRP, IMC1b, MAOP, P25, P28, SOAP, Cap380, CSP, ECP1, IMC1a, LAP1/CCp3/SR, LAP2/CCp1, LAP3/CCp5, LAP4/CCp2, LAPS/FNPA, LAP6/CCp4, transglutaminase, CSP, CRMP1, CRMP2, MAEBL, TRAP, and UOS3/TREP/S6. In some embodiments, the one or more *Plasmodium* polypeptides are selected from the group consisting of P48/45, P25, P28, P230 and HAP2.

In some embodiments, the nucleic acid sequence encodes a *Plasmodium* surface protein P48/45, or immunogenic fragment thereof, having at least about 60% sequence identity to SEQ ID NO: 11 or SEQ ID NO:1, for example, at least about 65%, 70%, 75%, 80%, 85%, 90%, 95%, 98% or 99% sequence identity to SEQ ID NO:11 or SEQ ID NO:1. In some embodiments, the nucleic acid sequence encodes *Plasmodium* surface protein P48/45 of SEQ ID NO: 11 or SEQ ID NO:1.

In some embodiments, the nucleic acid sequence encodes *Plasmodium* surface protein P48/45 residues 178-448 having at least about 60% sequence identity to SEQ ID NO:10, SEQ ID NO:23 or SEQ ID NO:25, for example, at least about 65%, 70%, 75%, 80%, 85%, 90%, 95%, 98% or 99% sequence identity to SEQ ID NO:10, SEQ ID NO:23 or SEQ ID NO:25. In some embodiments, the nucleic acid sequence encodes *Plasmodium* surface protein P48/45 residues 178-448 having 100% sequence identity to SEQ ID NO:10, SEQ ID NO:23 or SEQ ID NO:25. In various embodiments, the nucleic acid sequence encoding *Plasmodium* surface protein P48/45 residues 178-448 does not encode a signal peptide or transmembrane domain from the native or full-length P48/45 protein.

In some embodiments, the nucleic acid sequence encodes *Plasmodium* surface protein P25 and has at least about 60% sequence identity to SEQ ID NO:13 or SEQ ID NO:2, for example, at least about 65%, 70%, 75%, 80%, 85%, 90%, 95%, 98% or 99% sequence identity to SEQ ID NO: 13 or SEQ ID NO:2. In some embodiments, the nucleic acid sequence encodes *Plasmodium* surface protein P25 of SEQ ID NO: 13 or SEQ ID NO:2.

In some embodiments, the nucleic acid sequence encodes *Plasmodium* surface protein P25 residues 22-193 having at least about 60% sequence identity to SEQ ID NO:12, SEQ ID NO:28, SEQ ID NO:38 and/or SEQ ID NO:39, for example, at least about 65%, 70%, 75%, 80%, 85%, 90%, 95%, 98% or 99% sequence identity to SEQ ID NO:12, SEQ ID NO:28, SEQ ID NO:38 and/or SEQ ID NO:39. In some embodiments, the nucleic acid sequence encodes *Plasmodium* surface protein P25 residues 22-193 having 100% sequence identity to SEQ ID NO:12, SEQ ID NO:28, SEQ ID NO:38 and/or SEQ ID NO:39. In various embodiments, the nucleic acid sequence encoding *Plasmodium* surface protein P25 residues 22-193 does not encode a signal peptide or transmembrane domain from the native or full-length P25 protein.

In some embodiments, the nucleic acid sequence encodes *Plasmodium* surface protein P28 and has at least about 60% sequence identity to SEQ ID NO: 16 or SEQ ID NO:6, for example, at least about 65%, 70%, 75%, 80%, 85%, 90%, 95%, 98% or 99% sequence identity to SEQ ID NO:16 or SEQ ID NO:6. In some embodiments, the nucleic acid sequence encodes *Plasmodium* surface protein P28 of SEQ ID NO:16 or SEQ ID NO:6.

In some embodiments, the nucleic acid sequence encodes *Plasmodium* surface protein P28 residues 23-179 or 24-179 having at least about 60% sequence identity to SEQ ID NO:15, SEQ ID NO:18 or SEQ ID NO:31, for example, at least about 65%, 70%, 75%, 80%, 85%, 90%, 95%, 98% or 99% sequence identity to SEQ ID NO:15, SEQ ID NO:18 or SEQ ID NO:31. In some embodiments, the nucleic acid sequence encodes *Plasmodium* surface protein P28 residues 23-179 or 24-179 having 100% sequence identity to SEQ ID NO:15, SEQ ID NO:18 or SEQ ID NO:31. In various embodiments, the nucleic acid sequence encoding *Plasmodium* surface protein P28 residues 23-179 or 24-179 does not encode a signal peptide or transmembrane domain from the native or full-length P28 protein.

In some embodiments, the nucleic acid sequence encodes *Plasmodium* surface protein P230, or immunogenic fragment thereof, and has at least about 60% sequence identity to SEQ ID NO: 34, for example, at least about 65%, 70%, 75%, 80%, 85%, 90%, 95%, 98%, 99% or 100% sequence identity to SEQ ID NO:34. In some embodiments, the nucleic acid sequence encodes amino acid residues 444-730 of *Plasmodium* surface protein P230. In some embodiments, the nucleic acid sequence encodes a *Plasmodium* surface protein P230, or immunogenic fragment thereof, having at least about 60% sequence identity to SEQ ID NO: 35, for example, at least about 65%, 70%, 75%, 80%, 85%, 90%, 95%, 98%, 99% or 100% sequence identity to SEQ ID NO:35. In various embodiments, the nucleic acid sequence encoding *Plasmodium* surface protein P230 residues 444-730 does not encode a signal peptide or transmembrane domain from the native or full-length P230 protein.

In some embodiments, the nucleic acid sequence encodes *Plasmodium* surface protein HAP2, or immunogenic fragment thereof, and has at least about 60% sequence identity to SEQ ID NO: 36, for example, at least about 65%, 70%, 75%, 80%, 85%, 90%, 95%, 98%, 99% or 100% sequence identity to SEQ ID NO:36. In some embodiments, the nucleic acid sequence encodes a *Plasmodium* surface protein HAP2, or immunogenic fragment thereof, having at least about 60% sequence identity to SEQ ID NO: 37, for example, at least about 65%, 70%, 75%, 80%, 85%, 90%, 95%, 98%, 99% or 100% sequence identity to SEQ ID NO:37. In various embodiments, the nucleic acid sequence encoding *Plasmodium* surface protein HAP2 does not encode a signal peptide or transmembrane domain from the native or full-length HAP2 protein.

In some embodiments, the nucleic acid sequence is operably linked to a nucleic acid sequence encoding one or more tags selected from the group consisting of an affinity tag, a purification tag, an immunogenicity tag, a delivery tag, a secretion signal peptide and a stability tag. In some embodiments, the nucleic acid sequence is operably linked to a nucleic acid sequence encoding one or more tags selected from the group consisting of poly-His, Mistic, serum amyloid A (SAA), Tic40, small ubiquitin modifier peptide (SUMO), Streptavidin-Binding Peptide (SBP), green fluorescent protein (GFP), FLAG, cholera toxin beta subunit (CTB), and heat-labile enterotoxin beta subunit (LTB). In various embodiments, the nucleic acid sequence is operably linked to a nucleic acid sequence encoding a cholera toxin beta subunit (CTB). In some embodiments, the nucleic acid sequence encoding a cholera toxin beta subunit (CTB) has at least 60% sequence identity, for example, at least 65%, 70%, 75%, 80%, 85%, 90%, 95%, 98%, 99% or 100% sequence identity to SEQ ID NO:32. In some embodiments, the nucleic acid sequence encoding a cholera toxin beta subunit (CTB) has a nucleic acid sequence of SEQ ID NO:32.

In some embodiments, the methods do not comprise the step of denaturing and refolding the *Plasmodium* polypeptide. In some embodiments, the *Plasmodium* polypeptide is not fused to granule bound starch synthase (GBSS).

In a related aspect, the invention further provides methods for interfering with, reducing, preventing, inhibiting and/or delaying the transmission of a *Plasmodium* infection in a susceptible host, e.g., a mammal, by administration to the host of an effective amount of a *Plasmodium* polypeptide produced in an algal host cell, or an immunogenic fragment thereof, sufficient for the host to develop transmission blocking antibodies against the administered polypeptide, thereby interfering with, reducing, preventing, inhibiting and/or delaying the transmission of the *Plasmodium* infection. In various embodiments, the *Plasmodium* polypeptide is in the algal host cell which has been engineered to express the *Plasmodium* polypeptide. In such embodiments, the *Plasmo-*

*dium* polypeptide may be fused to a cholera toxin beta subunit (CTB). The algal host cell is administered orally to the susceptible host. In various embodiments, the algal host cell is freeze-dried prior to oral administration. The embodiments of the *Plasmodium* polynucleotides and polypeptides are as described herein. The inoculating *Plasmodium* polypeptides produced in an algal host cell are not glycosylated and typically have not been denatured and refolded. The *Plasmodium* polypeptides can be isolated and/or purified prior to administration to the susceptible host. The embodiments of the polynucleotides and encoded *Plasmodium* polypeptides expressed in the algal host cell are described herein.

DEFINITIONS

The terms "treating" and "treatment" and variants thereof refer to delaying the onset of, retarding or reversing the progress of, alleviating or preventing either the disease or condition to which the term applies (e.g., malaria), or one or more symptoms of such disease or condition. Treating and treatment encompass both therapeutic and prophylactic treatment regimens.

The terms "inhibiting," "reducing," "decreasing" with respect to malaria or *Plasmodium* infection refers to extent of infection and/or progression of disease in a subject by a measurable amount using any method known in the art. The infection and/or progression of malaria is inhibited, reduced or decreased if the *Plasmodium* parasitic burden is at least about 10%, 20%, 30%, 50%, 80%, or 100% reduced in comparison to the *Plasmodium* parasitic burden prior to administration with one or more of the *Plasmodium* transmission blocking polypeptides, as described herein.

The term "effective amount" or "pharmaceutically effective amount" refer to the amount and/or dosage, and/or dosage regime of one or more compounds necessary to bring about the desired result e.g., an amount sufficient to induce or elicit a transmission blocking immune response in a susceptible host and/or for preventing and/or mitigating in a mammal one or more symptoms associated with a *Plasmodium* infection.

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

The terms "subject," "patient," or "individual" interchangeably refer to any mammal, for example, humans and non-human primates, domestic mammals (e.g., canine, feline), agricultural mammals (e.g., bovine, equine, ovine, porcine) and laboratory mammals (e.g., mouse, rat, rabbit, hamster).

A "susceptible organism" or "susceptible host" is a *Plasmodium* host that is susceptible to malaria, for example, humans, non-human mammals, and chickens. The susceptible host may or may not be presently or previously infected by a *Plasmodium* parasite. In various embodiments, the susceptible host has been or will be exposed to potential infection with a *Plasmodium* parasite.

As used herein, "isolated," when referring to a molecule or composition, such as, e.g., a *Plasmodium* nucleic acid or polypeptide, means that the molecule or composition is separated from at least one other compound, such as a protein, other nucleic acids (e.g., RNAs), or other contaminants with which it is associated in vivo or in its naturally occurring state. Thus, a *Plasmodium* nucleic acid or polypeptide composition is considered isolated when the *Plasmodium* nucleic acid or polypeptide has been isolated from any other component with which it is naturally associated, e.g., cell membrane, as in a cell extract. An isolated composition can, however, also be substantially pure. An isolated composition can be in a homogeneous state and can be in a dry or an aqueous solution. Purity and homogeneity can be determined, for example, using analytical chemistry techniques such as polyacrylamide gel electrophoresis (SDS-PAGE) or high performance liquid chromatography (HPLC). Thus, the isolated *Plasmodium* nucleic acid or polypeptide compositions of this invention do not contain materials normally associated with their in situ environment. Even where a protein has been isolated to a homogenous or dominant band, there are trace contaminants which co-purify with the desired protein.

The terms "identical" or percent "identity," and variants thereof in the context of two or more polynucleotide sequences, refer to two or more sequences or subsequences that are the same. Sequences are "substantially identical" if they have a specified percentage of nucleic acid residues or nucleotides that are the same (i.e., at least 60% identity, optionally at least 65%, 70%, 75%, 80%, 85%, 90%, 95%, 96%, 97%, 98%, or 99% identity over a specified region (or the whole reference sequence when not specified)), when compared and aligned for maximum correspondence over a comparison window, or designated region as measured using one of the following sequence comparison algorithms or by manual alignment and visual inspection. The present invention provides polynucleotides improved for expression in algal host cells that are substantially identical to the polynucleotides of SEQ ID NOs: 1-9, 11, 13, 16, 34 and/or 36. Optionally, the identity exists over a region that is at least about 50 amino acids in length, or more preferably over a region that is 100, 200, 300, 400, 500, 600, 800, 1000, or more, nucleic acids in length, or over the full-length of the sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "comparison window", and variants thereof, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can also be conducted by the local homology algorithm of Smith and Waterman Add. APL. Math. 2:482 (1981), by the homology alignment algorithm of Needle man and Wunsch J. Mol. Biol. 48:443 (1970), by the search for similarity method of Pearson and Lipman Proc. Natl. Acad. Sci. (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), Karlin and Altschul Proc. Natl. Acad. Sci. (U.S.A.) 87:2264-2268 (1990), or by manual alignment and visual inspection (see, e.g., Ausubel et al., Current Protocols in Molecular Biology (1995 supplement)).

Examples of an algorithm that is suitable for determining percent sequence identity and sequence similarity include the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information (on the internet at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Standard BLAST algorithm parameters have an expected threshold of 10 (according to the stochastic model of Karlin and Altschul (PNAS, 87:2264-2268 (1990)); a word size of 28; reward and penalty of 1/−2 (a ratio of 0.5, or 1/−2, is used for sequences that are 95% conserved); and a linear GAP cost.

The term "substantial identity" of polynucleotide sequences means that a polynucleotide comprises a sequence that has at least 80% sequence identity, preferably at least 85%, more preferably at least 90% and most preferably at least 95%, compared to a reference sequence, the programs described above using standard parameters. Thus, if a sequence has about 80% sequence homology to a known *Plasmodium* polynucleotide or variant thereof, then that sequence is considered to be from a species of *Plasmodium*, respectfully. One of skill will recognize that these values can be appropriately adjusted to determine corresponding identity of proteins encoded by two nucleotide sequences by taking into account codon degeneracy, amino acid similarity, reading frame positioning and the like.

Substantial identity" of amino acid sequences for these purposes means sequence identity of at least 60%, preferably at least 90%, and most preferably at least 95%. Thus, if a sequence has about 60% sequence identity to a known *Plasmodium* polypeptide or variant thereof, then that sequence is considered to be from a species of *Plasmodium*, respectfully. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, asp artic acid-glutamic acid, and asparagine-glutamine.

Determination of "substantial identity" can be focused over defined subsequences, such as known structural domains. For example, for P25 and P28 polypeptides, another measure of structural similarity will be the striking alignment of cysteine (cys) residues and the spacing between the cys residues. The reason why these residues are of higher importance than others is that they are involved in recreating the disulfide bond arrangements that comprise the epidermal growth factor (EGF)-like domains (evolutionary conserved protein domains encompassed by Pfam PF00008 and/or Pfam PF00053). These domains are the hallmarks of P25 and P28 polypeptides from different species of *Plasmodium*. See, e.g., FIG. 6.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 1 molar at pH 7 and the temperature is at least about 60° C.

In the present invention, mRNA encoded by the nucleic acids of the invention can be identified in Northern blots under stringent conditions using the sequences disclosed here or fragments of, typically, at least about 100 nucleotides. For the purposes of this disclosure, stringent conditions for such RNA-DNA hybridizations are those which include at least one wash in 6×SSC for 20 minutes at a temperature of at least about 50° C., usually about 55° C. to about 60° C., or equivalent conditions.

Another indication that protein sequences are substantially identical is if one protein is immunologically reactive with antibodies raised against the other protein. Thus, the proteins of the invention include proteins immunologically reactive with antibodies raised against P25 and/or P28 polypeptides, and fusion proteins thereof.

Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine, and UGG, the single codon for Trp) can be modified to yield a functionally identical molecule by standard techniques. Accordingly, each "silent variation" of a nucleic acid which encodes a polypeptide is implicit in each described sequence.

The term "conservatively modified variations" refers to individual substitutions, deletions or additions which alter, add or delete a single amino acid or a small percentage of amino acids (typically less than 5%, more typically less than 1%) in an encoded sequence, where the alterations result in the substitution of an amino acid with a chemically similar amino acid; and the alterations, deletions or additions do not alter the structure, function and/or immunogenicity of the sequence. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The term "P25" and "P28" polynucleotide refers to nucleic acid molecules which encode *Plasmodium* surface proteins P25 and P28 polypeptides, respectively, and nucleotides with substantial identity to these sequences, as described herein. P25 and P28 polypeptides are polypeptides containing a sequence identical to or substantially identical to the amino acid sequence of a class of 28 kD proteins expressed on the surface of *Plasmodium* ookinetes. Wild-type nucleic acid sequences for P25 and P28 are known in the art. Exemplary GenBank reference numbers for *Plasmodium* P25 polynucleotides and the encoded P25 polypeptides include without limitation XM_001347551.1→XP_001347587.1; AF179423.1→AAD55785.1; AF154117_1→AAD39544.1; AF193769.1→AAF63684.1; XM_739934.1→XP_745027.1; XM_670232.1→XP_675324.1; XM_001608410.1→XP_001608460.1; and XM_002261792.1→XP_002261828.1). Exemplary GenBank reference numbers for *Plasmodium* P28 polynucleotides and the encoded P28 polypeptides include without limitation XM_720006.1→XP_725099.1; XM_001608411.1→XP_001608461.1; AF232052.1→AAG27292.1; AF232046.1→AAG27286.1. Further P28 homologs are described, e.g., in Taylor, et al., *Mol. Biochem. Parasitol.* (2000) 110 (2), 429-434 and in Intl. Patent Publ. Nos. WO 99/029868; WO 98/014472 and WO 95/08631. *Plasmodium* ookinete surface protein P28 and *Plasmodium* ookinete surface protein P25 comprise conserved domains (e.g., EGF and EGF-like domains, defined by Pfam PF00008 and Pfam PF00053) and are defined by Pfam PF06247. See also, Sharma, *In Silico Biology* (2008) 8:193-206.

The term "P48/45" polynucleotide refers to nucleic acid molecules which encode *Plasmodium* surface protein P48/45 and nucleotides with substantial identity to these sequences. P48/45 polypeptides are polypeptides containing a sequence identical to or substantially identical to the amino acid sequence of a class of proteins expressed on the surface of *Plasmodium* gametes. Wild-type nucleic acid sequences for P48/45 are known in the art. Exemplary GenBank reference numbers for *Plasmodium* P48/45 polynucleotides and the encoded polypeptides include without limitation XM_001614196.1→XP_001614246.1; X81648.1→CAA57308.1; AF356146.1→AAL74380.1. *Plasmodium* sexual stage antigen P48/45 comprises conserved domains (e.g., EGF and EGF-like domains, defined by Pfam PF00008 and Pfam PF00053) and is defined by Pfam PF07422.

The term "P230" polynucleotide refers to nucleic acid molecules which encode *Plasmodium* surface protein P230 and nucleotides with substantial identity to these sequences. P230 polypeptides are polypeptides containing a sequence identical to or substantially identical to the amino acid sequence of a class of proteins expressed on the surface of *Plasmodium* gametes. Wild-type nucleic acid sequences for P230 are known in the art. Exemplary GenBank reference numbers for *Plasmodium* P230 polynucleotides and the encoded polypeptides include without limitation XM_002260973.1→XP_002261009.1;
1.XM_001613322.1→XP_001613372.1;
1.XM_001612970.1→XP_001613020.1;
1.XM_001349564.1→XP_001349600.1.

The terms "Hapless 2" and "HAP2" polynucleotide interchangeably refer to nucleic acid molecules which encode *Plasmodium* surface protein HAP2 and nucleotides with substantial identity to these sequences. HAP2 polypeptides are polypeptides containing a sequence identical to or substantially identical to the amino acid sequence of a class of proteins expressed on the surface of *Plasmodium* gametes. Wild-type nucleic acid sequences for HAP2 are known in the art. Exemplary GenBank reference numbers for *Plasmodium* HAP2 polynucleotides and the encoded polypeptides include without limitation 1.XM_001347388.1→XP_001347424.1;
1.XM_002808802.1→XP_002808848.1;
1.XM_002258745.1→XP_002258781.1;
1.XM_002258139.1→XP_002258175.1;
1.XM_001614958.1→XP_001615008.1;
1.XM_001614403.1→XP_001614453.1;
1.XM_671808.1→XP_676900.1;
1.XM_666981.1→XP_672073.1;
1.XM_664994.1→XP_670086.1;
1.XM_664787.1→XP_669879.1;
1.XM_719993.1→XP_725086.1;
1.XM_735338.1→XP_740431.1;
1.XM_733669.1→XP_738762.1;
1.XM_729905.1→XP_734998.1;
1.XM_727737.1→XP_732830.1.

The terms P25, P28, P48/45, P230 and HAP2 polypeptides encompass native proteins as well as recombinantly produced modified proteins that induce an immune response (i.e., immunogenic fragments thereof), including a transmission blocking immune response. It also includes immunologically active fragments of these proteins. The terms P25, P28, P48/45, P230 and/or HAP2 polypeptides also encompass partially or completely deglycosylated forms. P25, P28, P48/45, P230 and/or HAP2 polypeptides of the invention (i.e., expressed or produced from an algal host cell) can be full-length or an immunologically active fragment, and alternatively, fusion proteins comprising two or more *Plasmodium* polypeptides. The polypeptides can be between about 30 and 200 amino acids, typically at least about 50, 75 or 100 amino acids in length. P25, P28, P48/45, P230 and/or HAP2 polypeptides are characterized by their ability to induce transmission blocking immune responses. The terms P25, P28, P48/45, P230 and/or HAP2 polypeptides encompasses homologues and allelic variants of P25, P28, P48/45, P230 and/or HAP2. Such homologues, also referred to as P25, P28, P48/45, P230 and/or HAP2 polypeptides, respectively, include variants of the native proteins constructed by in vitro techniques, and proteins from *Plasmodium* parasites related to *P. vivax* and *P. falciparum*, e.g., *Plasmodium ovale, Plasmodium malariae, Plasmodium chabaudi, Plasmodium berghei, Plasmodium knowlesi, Plasmodium reichenowi* or *Plasmodium yoelii*. For example, one skilled in the art will appreciate that for certain uses it is advantageous to produce a P25, P28, P48/45, P230 and/or HAP2 polypeptide sequence that is lacking a structural characteristic; e.g., one may remove a transmembrane domain to obtain a polypeptide that is more soluble in aqueous solution. In various embodiments, the encoded *Plasmodium* polypeptide comprises one or more EGF domains or EGF-like domains and does not comprise a native signal peptide or transmembrane domain. The P25, P28, P48/45, P230 and/or HAP2 polypeptides of the invention, and sequences encoding these proteins, also include fusion proteins comprising one or *Plasmodium* surface polypeptides as well as non-malarial sequences, e.g., epitope tags, enzyme cleavage recognition sequences, signal sequences, secretion signals (e.g., yeast alpha mating pheromone signal sequence) and the like.

In the expression of recombinant genes, such as expression cassette or vector-expressed sequences or transgenes, one of skill will recognize that the inserted polynucleotide sequence need not be identical and may be "substantially identical" to a sequence of the gene from which it was derived. These variants are specifically covered by the terms P25, P28, P48/45, P230 and/or HAP2. These variations include partially or completely deglycosylated forms of the polypeptides, and the nucleic acids which encode these variations.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the above term. In addition, the term "polynucleotide sequence from a P25, P28, P48/45, P230 and/or HAP2 gene" specifically includes those sequences substantially identical (determined as described below) with a P25, P28, P48/45, P230 and/or HAP2 gene sequence and that encode proteins that retain the function of the P25, P28, P48/45, P230 and/or HAP2 protein, respectively. Thus, in the case of the P25, P28, P48/45, P230 and/or HAP2 genes disclosed herein, the above term includes variant polynucleotide sequences which have substantial identity with the sequences disclosed here and which encode proteins capable of inducing an immune response, such as, but not limited to, a transmission blocking immune response.

A "fusion protein" refers to a composition comprising at least one polypeptide or peptide domain which is associated with a second domain. The second domain can be a polypeptide, peptide, polysaccharide, or the like. The "fusion" can be an association generated by a peptide bond, a chemical linking, a charge interaction (e.g., electrostatic attractions, such as salt bridges, H-bonding, etc.) or the like. If the polypeptides are recombinant, the "fusion protein" can be translated from a common message. Alternatively, the compositions of the domains can be linked by any chemical or electrostatic means. The P25, P28, P48/45, P230 and/or HAP2 fusion proteins of the invention can comprise two or more *Plasmodium* immunogenic polypeptides and/or also include non-malarial sequences, e.g., linkers, epitope tags, enzyme cleavage recognition sequences, signal sequences, secretion signals, delivery sequences (e.g., CTB, LTB) and the like.

An "immunogen" refers to a compound or composition comprising a peptide, polypeptide or protein which is "immunogenic," i.e., capable of eliciting, augmenting or boosting a cellular and/or humoral immune response, either alone or in combination or linked or fused to another substance. An immunogenic composition can be a peptide of at least about 5 amino acids, a peptide of 10 amino acids in length, a fragment 15 amino acids in length, a fragment 20 amino acids in length or greater. The immunogen can comprise a "carrier" polypeptide and a hapten, e.g., a fusion protein or a carrier polypeptide fused or linked (chemically or otherwise) to another composition (described below). The immunogen can be recombinantly expressed in an immunization vector, which can be simply naked DNA comprising the immunogen's coding sequence operably linked to a promoter, e.g., a simple expression cassette. The immunogen includes antigenic determinants, or epitopes (described below), to which antibodies or TCRs bind, which are typically 3 to 10 amino acids in length.

An "antibody" refers to a polypeptide of the immunoglobulin family or a polypeptide comprising fragments of an immunoglobulin that is capable of noncovalently, reversibly, and in a specific manner binding a corresponding antigen. An exemplary antibody structural unit comprises a tetramer. Each tetramer is composed of two identical pairs of polypeptide chains, each pair having one "light" (about 25 kD) and one "heavy" chain (about 50-70 kD), connected through a disulfide bond. The recognized immunoglobulin genes include the $\kappa$, $\lambda$, $\alpha$, $\gamma$, $\delta$, $\epsilon$, and $\mu$ constant region genes, as well as the myriad immunoglobulin variable region genes. Light chains are classified as either $\kappa$ or $\lambda$. Heavy chains are classified as $\gamma$, $\mu$, $\alpha$, $\delta$, or $\epsilon$, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain (VL) and variable heavy chain (VH) refer to these regions of light and heavy chains respectively. As used in this application, an "antibody" encompasses all variations of antibody and fragments thereof that possess a particular binding specifically, e.g., for tumor associated antigens. Thus, within the scope of this concept are full length antibodies, chimeric antibodies, humanized antibodies, human antibodies, singly domain antibodies or nanobodies, single chain antibodies (ScFv), Fab, Fab', and multimeric versions of these fragments (e.g., F(ab')2) with the same binding specificity.

The phrase "specifically (or selectively) bind," when used in the context of describing the interaction between an antigen, e.g., a protein, to an antibody or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under designated immunoassay conditions, the antibodies or binding agents with a particular binding specificity bind to a particular antigen at least two times the background and do not substantially bind in a significant amount to other antigens present in the sample. Specific binding to an antibody or binding agent under such conditions may require the antibody or agent to have been selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least than 10 to 100 times over the background.

A "transmission blocking antibody" is an antibody which inhibits the growth or replication of a malarial parasite during the sexual stage of parasite development in the mosquito gut.

An "immunogenic composition" is a composition which elicits the production of antibodies or a cell-mediated immune response when administered to a mammal or other susceptible organism.

An "immunological carrier" or "carrier" in the immunological context (as opposed to a carrier which is a nonactive composition for the purpose of formulating, storing or carrying a pharmaceutical) is an composition which, when linked, joined, chemically coupled or fused to a second composition (e.g., protein, peptide, polysaccharide or the like) boosts or augments the cellular or humoral response to the composition. Any physiologic mechanism can be involved in this augmentation or boosting of the immune response. An immunogenic carrier is typically a polypeptide linked or fused to a second composition of interest comprising a protein, peptide or polysaccharide, where the carrier stimulates a cellular (T cell mediated) immune response that boosts or augments the humoral (B cell mediated, antibody-generating) immune response to the composition of interest. These second compositions can be "haptens," which are typically defined as compounds of low molecular weight that are not immunogenic by themselves, but that, when coupled to carrier molecules, can elicit antibodies directed to epitopes on the hapten. For example, the lack of an adequate immune response to the major polysaccharide of the *Haemophilus influenzae* type b capsule (PRP) in very young infants can be overcome by conjugating PRP to a T-cell dependent carrier protein (see Zepp (1997) Eur. J. Pediatr. 156:18-24). Alternatively, a peptide can be linked to a carrier simply to facilitate manipulation of the peptide in the generation of the immune response (see, e.g., Rondard (1997) Biochemistry 36:8962-8968).

An "epitope" refers to an antigenic determinant or antigen site that interacts with an antibody or a T cell receptor (TCR). An "antigen" is a molecule or composition that induces the production of an immune response. An antibody or TCR binds to a specific conformational (possibly charge-dependent) domain of the antigen, called the "antigenic determinant" or "epitope" (TCRs bind the epitope in association with a third molecule, a major histocompatibility complex (MHC) protein).

FIG. 4 illustrates a schematic for incorporation of a *Plasmodium* polypeptide into the genome of an algal chloroplast for heterologous expression in a unicellular green algal host cell. Expression of the *Plasmodium* polypeptide can be increased by altering the coding nucleic acid sequence to replace codons rarely expressed in algal host cells with codons more commonly expressed in algal host cells.

FIG. 5 illustrates representative options for gene constructs encoding *Plasmodium* polypeptides useful as transmission blocking vaccines to increase immunogenicity, stability, ease of purification and detection.

FIG. 6 illustrates a Web logo representation of 8 non-redundant sequences of P25 family of ookinete surface proteins (e.g., from *Plasmodium falciparum, Plasmodium vivax, Plasmodium ovale, Plasmodium malariae, Plasmodium chabaudi, Plasmodium berghei, Plasmodium knowlesi*, and *Plasmodium yoelii*). The conserved cysteines are represented in yellow color. Negatively charged (D and E), positively charged (K and R), and cysteine (C) residues are shown in red, blue and yellow color respectively whereas rest all residues are shown in black color. Conservation of cysteine residues in all the four EGF domains is well represented by the logos.

FIGS. 7A-C illustrate a map of plasmids used to construct *C. reinhardtii* strains harboring pfs48/45, pfs28, and pfs25. (A) Plasmid used for recombination at the psbH locus utilizing the psbD promoter. (B) Plasmid used for recombination at the psbA locus. (C) Plasmid used for recombination at the psbH locus using the psbA promoter.

FIGS. 8A-C illustrate a schematic diagram of codon-optimized algal expression constructs for the *Plasmodium falciparum* surface proteins Pfs48/45, Pfs25, and Pfs28. (A) Construct design for the expression of the C10 region of Pfs48/45 with a FLAG affinity sequence for purification. (B) Three constructs (JAGS, JAG7, and JAG28) created for the expression of Pfs25 each with varying peptide fusions to increase protein stability (GFP and SUMO) and for affinity purification. (C) Three constructs (JAG15, JAG13, JAG43) created for the expression of Pfs28 each with varying peptide fusions to increase protein stability (GFP and Tic-40) and for affinity purification. All expression constructs have kanamycin resistance cassette for selection.

FIGS. 9A-C illustrate nine plasmids containing variations in the c.r.-Pfs 48/45 gene, with altered codons for improved expression in algae, were created and integrated into the *C. reinhardtii* chloroplast genome using homologous recombination. A) List of *C. reinhardtii* strains created showing variations in the promoter and 5' UTR regions, the expression tag (FLAG or SAA) and in the length of the gene sequence integrated. B) Diagram of the integrated region of plasmids containing the psbD promoter and 5' UTR (D2) and the site of homologous recombination within the *C. reinhardtii* chloroplast genome resulting in the recovery of photosynthesis. C) Diagram of the integrated region of plasmids containing the psbA promoter and 5' UTR (D1) and the site of homologous recombination within the *C. reinhardtii* chloroplast genome resulting in kanamycin resistance.

Figure 10:
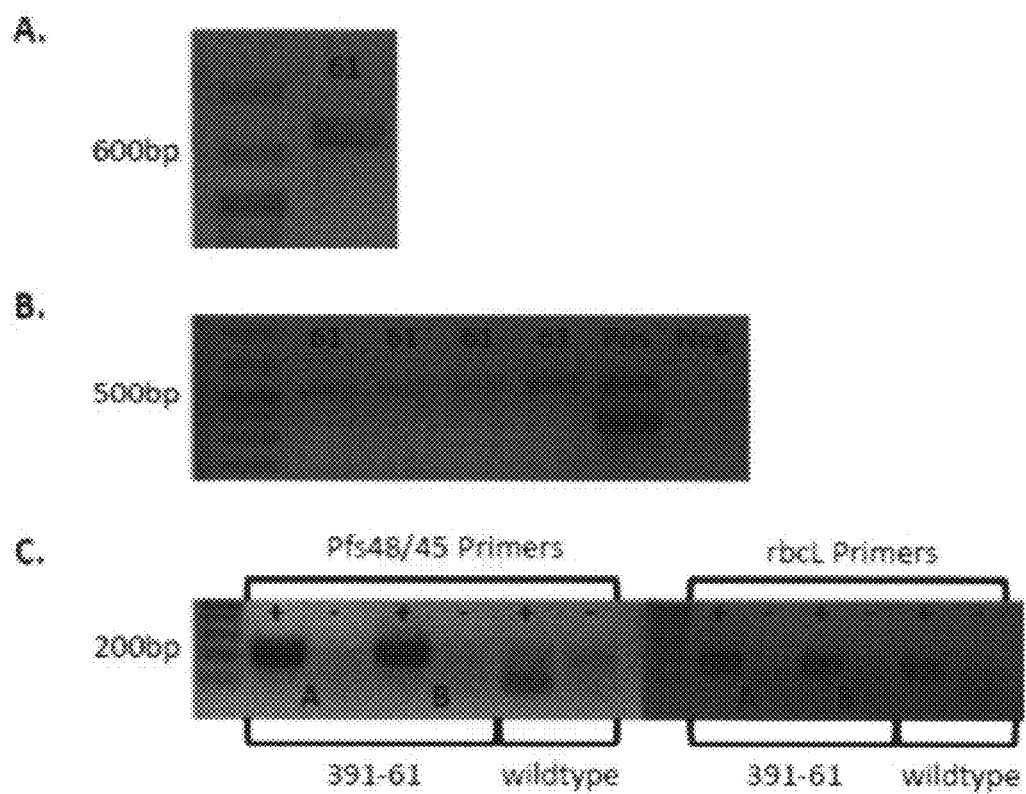

FIGS. 10A-C illustrate confirmation of complete integration and transcriptional expression for strain 391 (Line 61). A) Gene specific PCR confirmation of the presence of the c.r.Pfs 48/45 gene. B) PCR screen showing the loss of the endogenous psbA gene when compared to a control PCR product indicating 100% replacement of the psbA gene within all copies of the C. reinhardtii chloroplast genome. C) Qualitative cDNA analysis showing the transcription of the c.r.Pfs 48/45 gene compared to the rbcL control. A and B represent duplicate samples of the c.r.Pfs48/45 cDNA product.

Figure 11C:
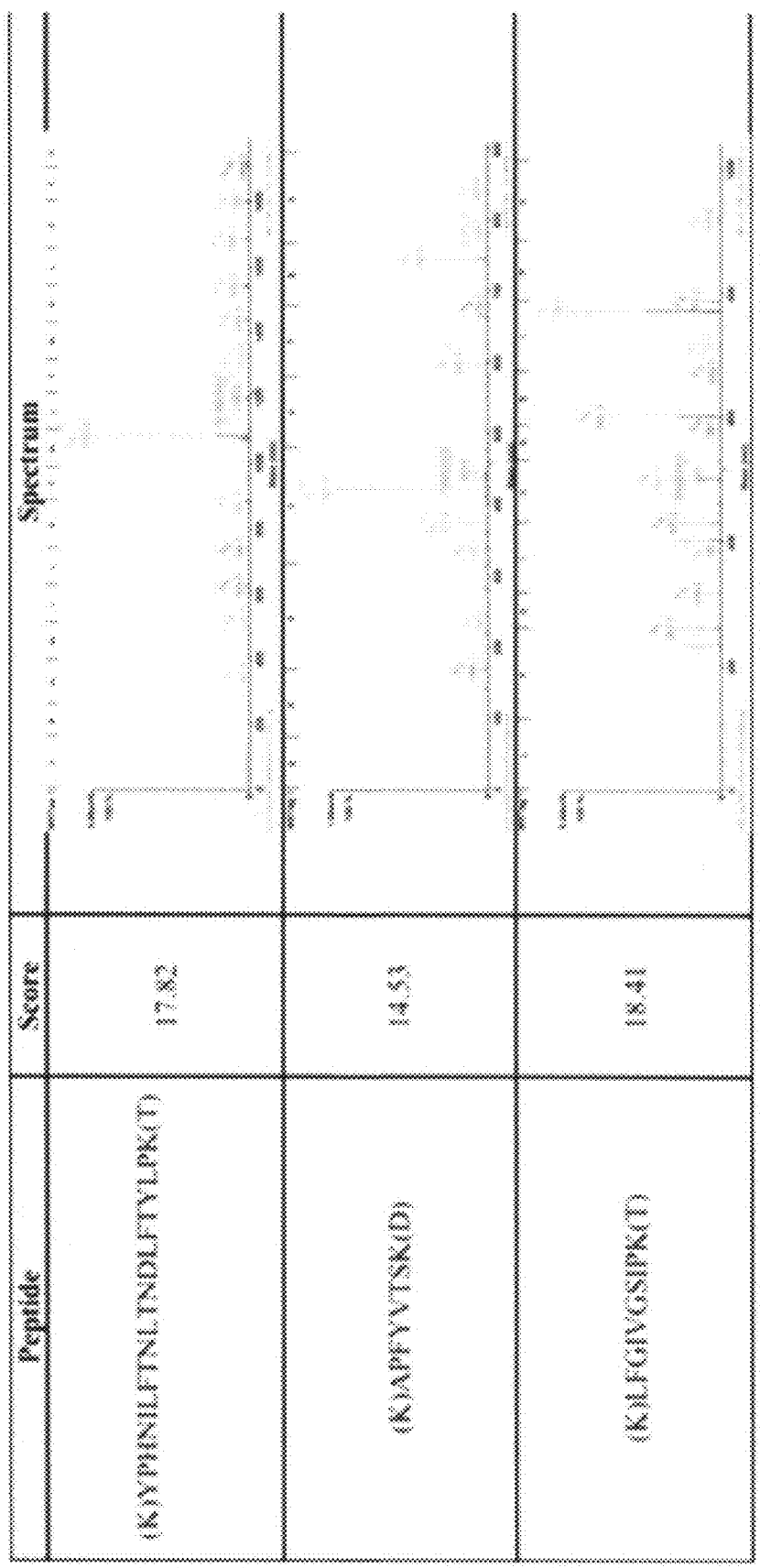

FIGS. 11A-C illustrate heterologous expression of c.r.-Pfs 48/45 protein (C10) fragment and peptide identification by mass spectrometry. A) Western blot of protein purification extracts including total protein (T), soluble protein (S), wash (W), and 5 elutions (E). FLAG specific primary antibody conjugated with amino peroxidase recognizes protein of approximately the correct size in the total protein extract and clearly in the second and third elution. B) Strain 391 c.r.Pfs48/45 amino acid sequence (SEQ ID NO: 19) showing the location of three peptides (bold and underlined) identified by mass spectrometry. C) Strain 391 c.r.Pfs48/45 peptide identification from by mass spectrometry (SEQ ID NO: 48, residues 2-18 of SEQ ID NO: 48, 49, residues 2-9 of SEQ ID NO: 49, SEQ ID NO: 50 and residues 2-11 of SEQ ID NO: 50, respectively, from left to right).

Figure 12:
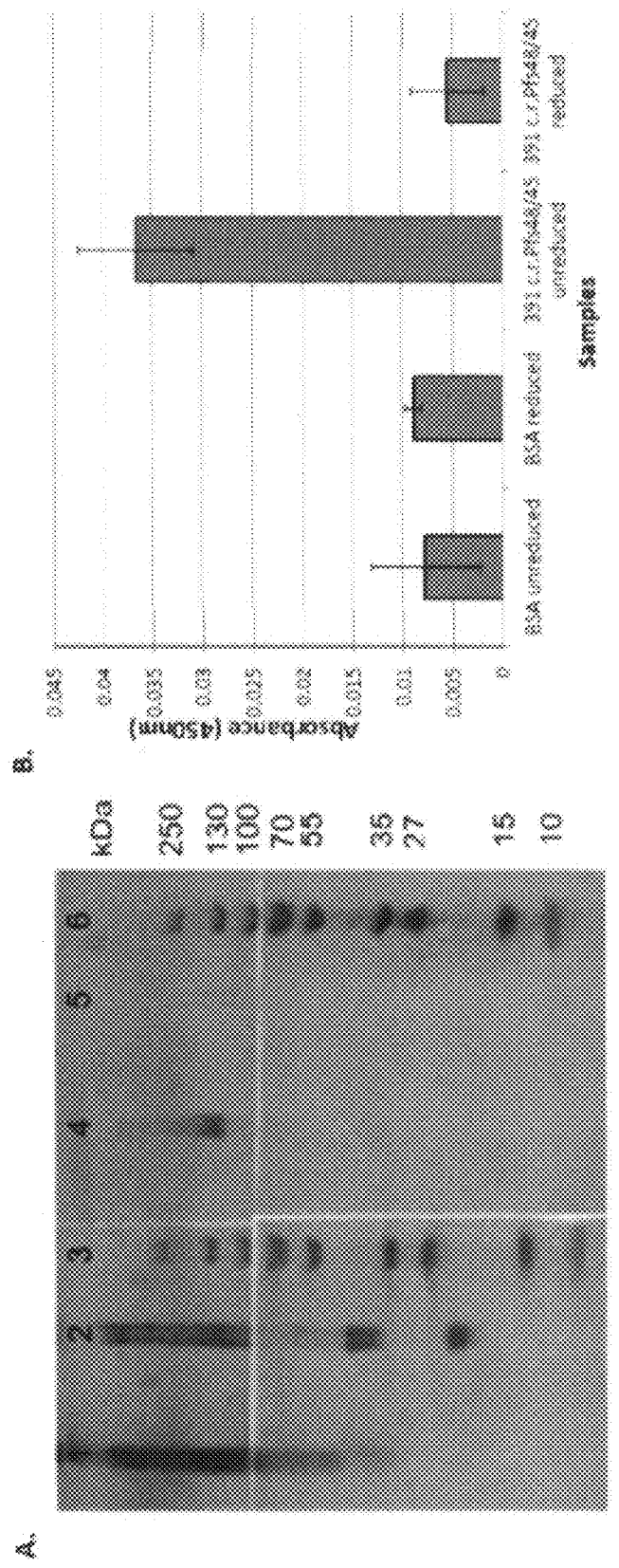

FIGS. 12A-B illustrate recognition of strain 391 c.r.Pfs48/45 recombinant protein conformation through Western Blot and ELISA assays. A) Western blot using antibody IIC5-10 (MRA-26), a conformation-specific anti-Pfs48/45 antibody showing that reduction of the 391 c.r.Pfs48/45 recombinant protein prevents recognition by antibody when compared to Western analysis using a FLAG antibody. B) ELISA assay confirming the Western Blot results showing that unreduced 391 c.r.Pfs48/45 recombinant protein is recognized at a higher level than either the reduced 391 c.r.Pfs48/45 protein sample or the BSA control standards.

Figure 13:
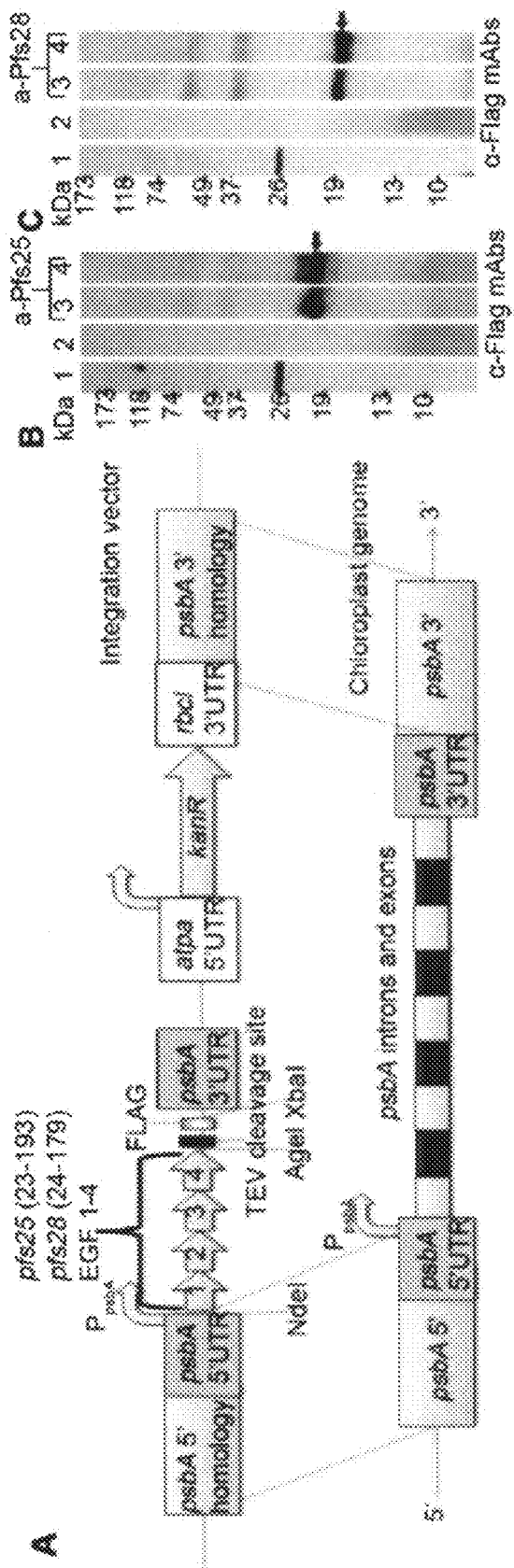
Figure 14:
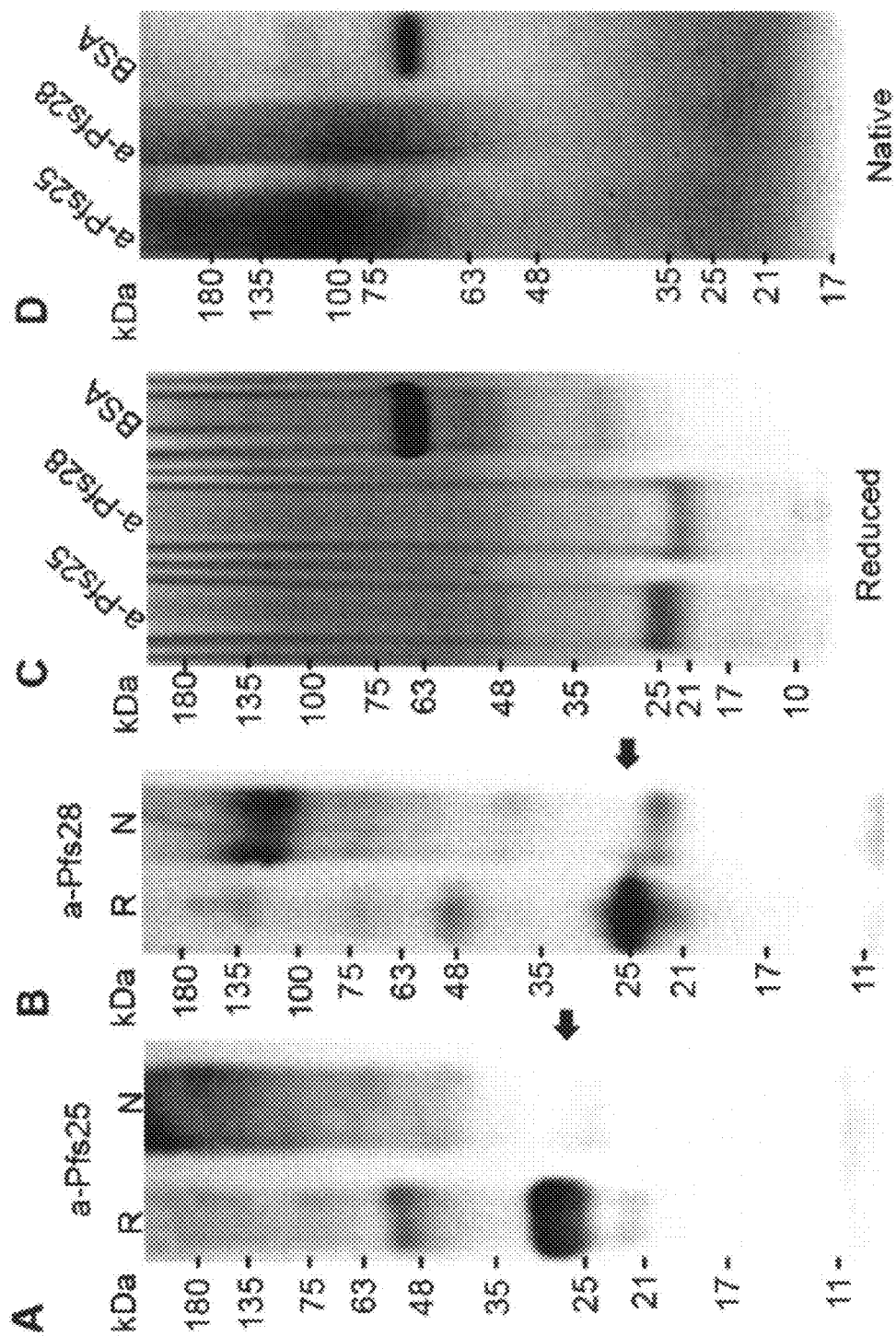

FIGS. 13A-C illustrate a diagram of chloroplast transformation vector and Western blots of C. reinhardtii transformed with vectors containing codon optimized pfs25 or pfs28. (A) The codon optimized nucleotide sequences corresponding to EGF domains 1-4 of pfs25 and pfs28 were separately cloned into an open reading frame that is upstream of a TEV protease site and FLAG epitope. Transgenes were integrated at the psbA locus by homologous recombination. Gene expression is driven by the psbA promoter and mRNA is stabilized by the psbA 5' and 3' untranslated regions (UTRs). (B) Western blot analysis of purified algae-produced HMGB1 containing a FLAG epitope (lane 1), lysate of untransformed parental strain (lane 2), lysate of C. reinhardtii containing a-pfs25 total protein (lane 3) and soluble protein (lane 4) probed with anti-FLAG mAbs. (C) Western blot using anti-FLAG mAbs of purified algae-produced HMGB1 containing a FLAG epitope (lane 1), lysate of untransformed parental strain (lane 2), lysate of C. reinhardtii containing a-pfs28 total protein (lane 3) and soluble protein (lane 4) probed with anti-FLAG mAbs.

FIGS. 14A-D illustrate immunoblot and Coomassie-blue stain of algae-produced Pfs25 and Pfs28 analyzed by SDS and Native-PAGE. Five micrograms of reduced and non-reduced affinity purified (A) a-Pfs25 and (B) a-Pfs28 were resolved by SDS-PAGE, transferred to nitrocellulose, and detected with anti-FLAG mAbs. (C) Five micrograms of reduced a-Pfs25, a-Pfs28, and BSA were resolved by SDS-PAGE and stained with Coomassie-blue. (D) Five micrograms of non-reduced a-Pfs25, a-Pfs28, and BSA were resolved by Native-PAGE and stained with Coomassie-blue. (R—reduced, N—non-reduced).

Figure 15:
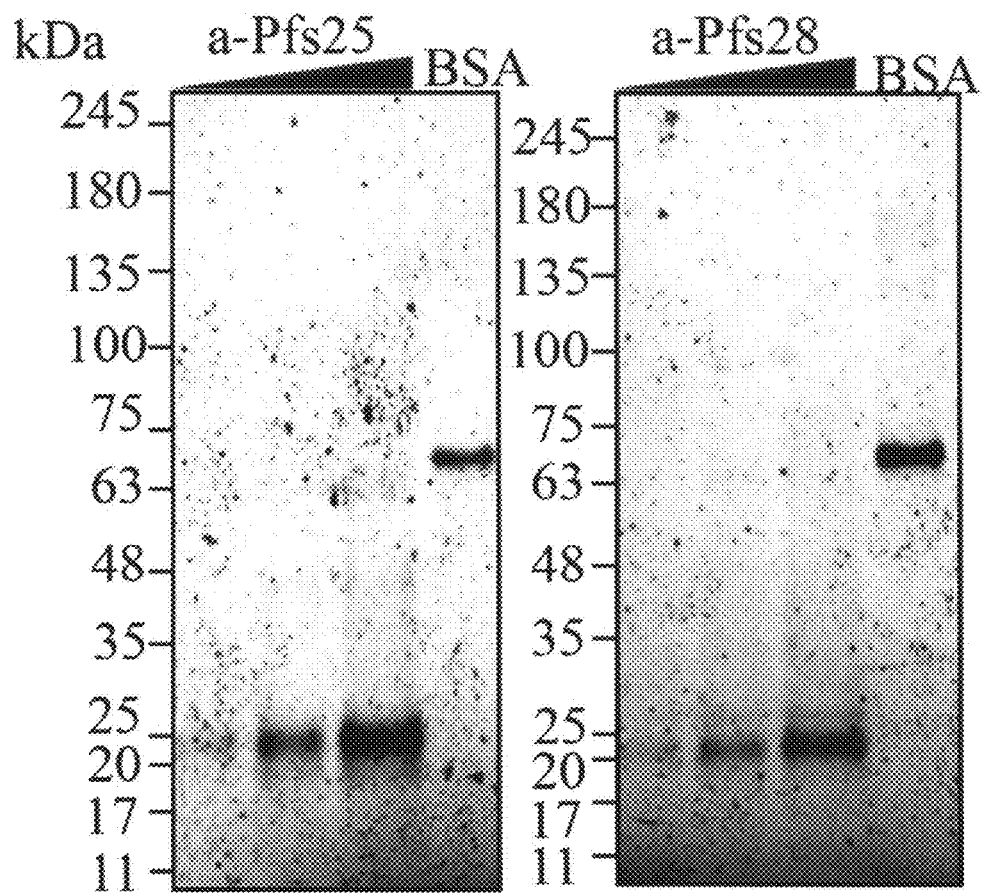

FIG. 15 illustrates silver stain analysis of algae-produced Pfs25 and Pfs28. Increasing amounts of affinity purified a-Pfs25 and a-Pfs28 (100, 200, and 400 ng) and 200 ng of BSA were resolved on 16% SDS-PAGE and total protein was detected using silver stain.

FIGS. 16A-B illustrate an immunoblot of reduced and non-reduced algae-produced Pfs25 and Pfs28 with monoclonal transmission blocking antibodies. Reduced and non-reduced a-Pfs25 and a-Pfs28 were resolved by SDS-PAGE, transferred to nitrocellulose, and detected with (A) anti-Pfs25 4B7 mAb and (B) anti-Pfs28-2D8 mAbs, respectively.

Figure 17:
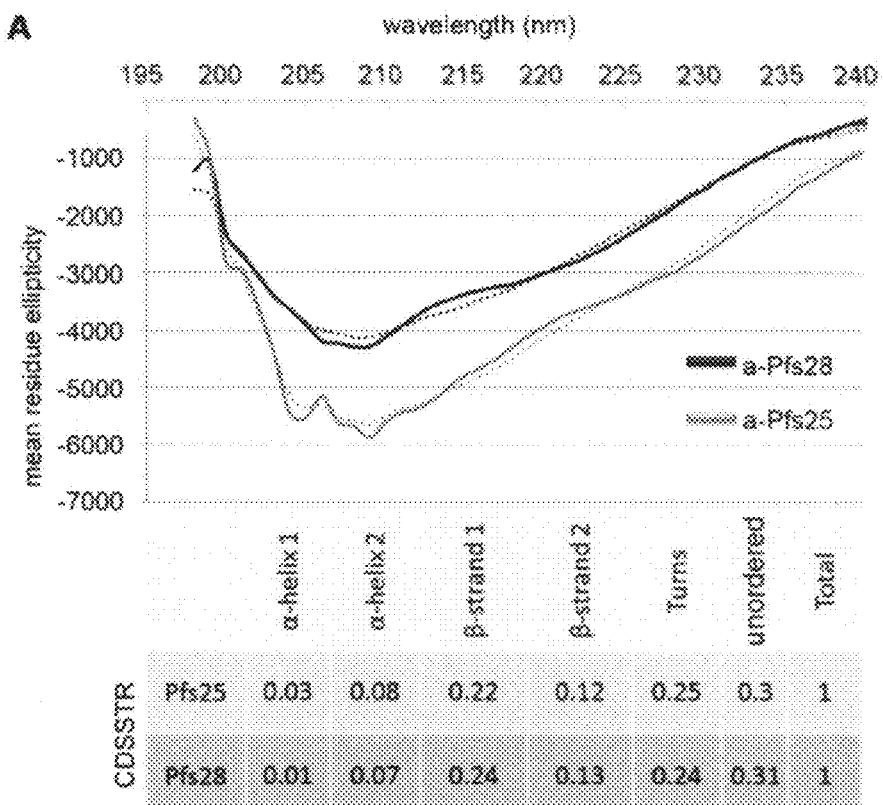
Figure 17:
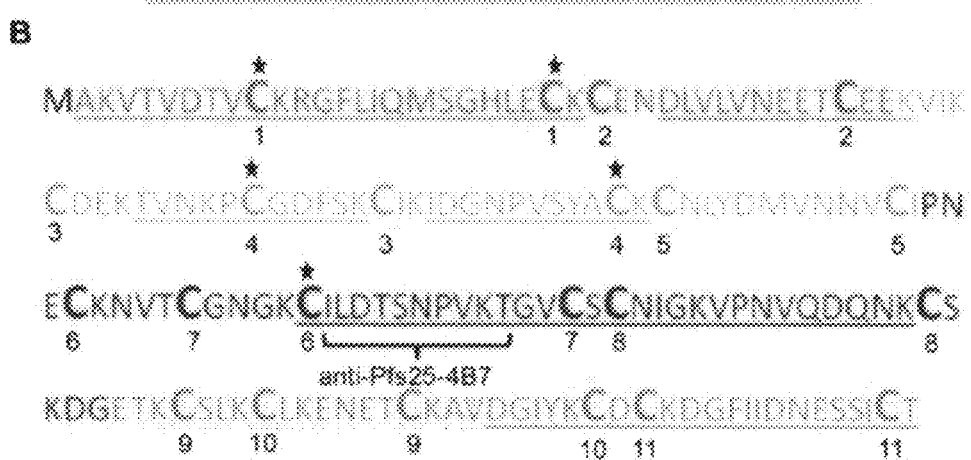

FIGS. 17A-B illustrate structural analysis of algae-produced Pfs25 and Pfs28. (A) Far-UV circular dichroism spectra of algae-produced Pfs25 (Gray) and Pfs28 (Black). Spectra shown are measured mean residue ellipticity (solid lines) and best fit (dotted lines) using CDSSTR. The contribution (shown as fractions) of each secondary structure to the overall spectra as predicted by CDSSTR. (B) Analysis of protected cysteines in a-Pfs25 by tandem mass spectrometry. The peptide sequence of Pfs25 from Ala22 to Thr193 is shown with EGF-like domain 1 (blue), 2(pink), 3(green), 4(orange) (SEQ ID NO: 51). Peptides detected by mass spectrometry are underlined and protected cysteines are marked by stars. Disulfide linkages between cysteines are marked numerically (i.e. the two cysteines labeled 1 form a disulfide linkage and so on). The epitope recognized by anti-Pfs25 4B7 mAb is indicated.

FIGS. 18A-D illustrate an analysis of antibodies from mice immunized with algae-produced Pfs25 or Pfs28. (A) ELISA titers of mouse anti-sera elicited by algae-produced Pfs25 and Pfs28. Mice were immunized with affinity purified a-Pfs25 or a-Pfs28 using complete Freund's adjuvant followed by boosters with incomplete Freund's adjuvant by intraperitoneal injection. Pooled sera was serially diluted and tested in triplicate against the corresponding algae-produced Pfs antigen; error bars are one standard deviation. Prebleed sera were tested as a negative control; error bars are four standard deviations. (B-D) Western blot analysis of P. falciparum mixed sexual stage lysates with anti-Pfs25-4B7 mAbs, a-Pfs 25 antisera, or a-Pfs28 antisera. Reduced and non-reduced sexual stage lysates were resolved by SDS-PAGE and transferred to nitrocellulose. Blots were probed with (B) anti-Pfs25-4B7 mAbs, (C) antibodies raised to a-Pfs25, and (D) antibodies raised to a-Pfs28 (R—reduced, N—non-reduced).

Figure 19:
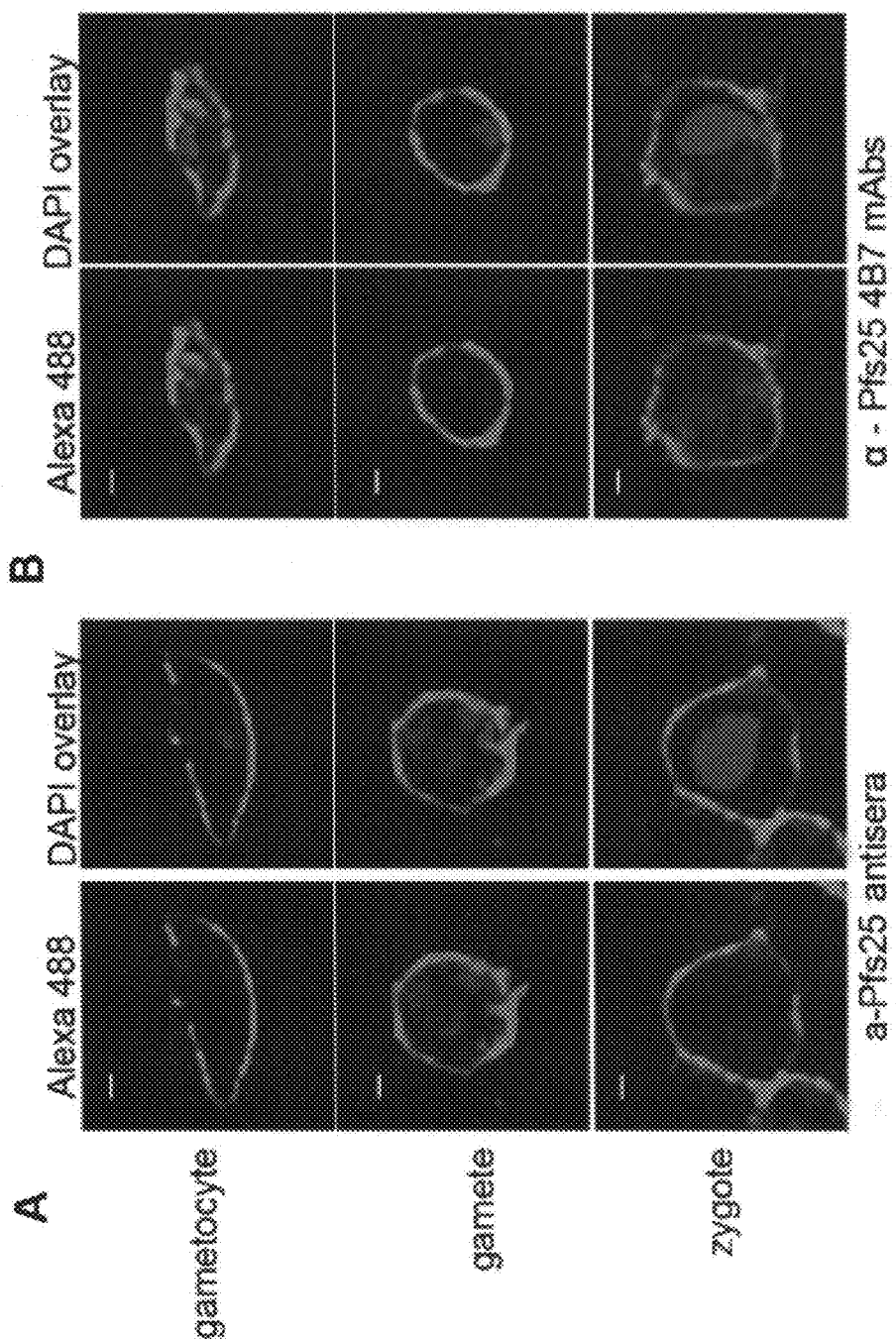

FIGS. 19A-B illustrate indirect immunofluorescence using immune sera from mice immunized with algae-produced Pfs25 or Pfs28 on in-vitro cultured P. falciparum gametocytes, gametes, and zygotes. DNA was stained using DAPI (blue) and antibody binding was visualized using Alexa Fluor 488-conjugated rabbit anti-mouse IgG (green) for (A) a-Pfs25 antisera and (B) anti-Pfs25 4B7 mAbs. Scale bars, 1 μm.

Figure 20:
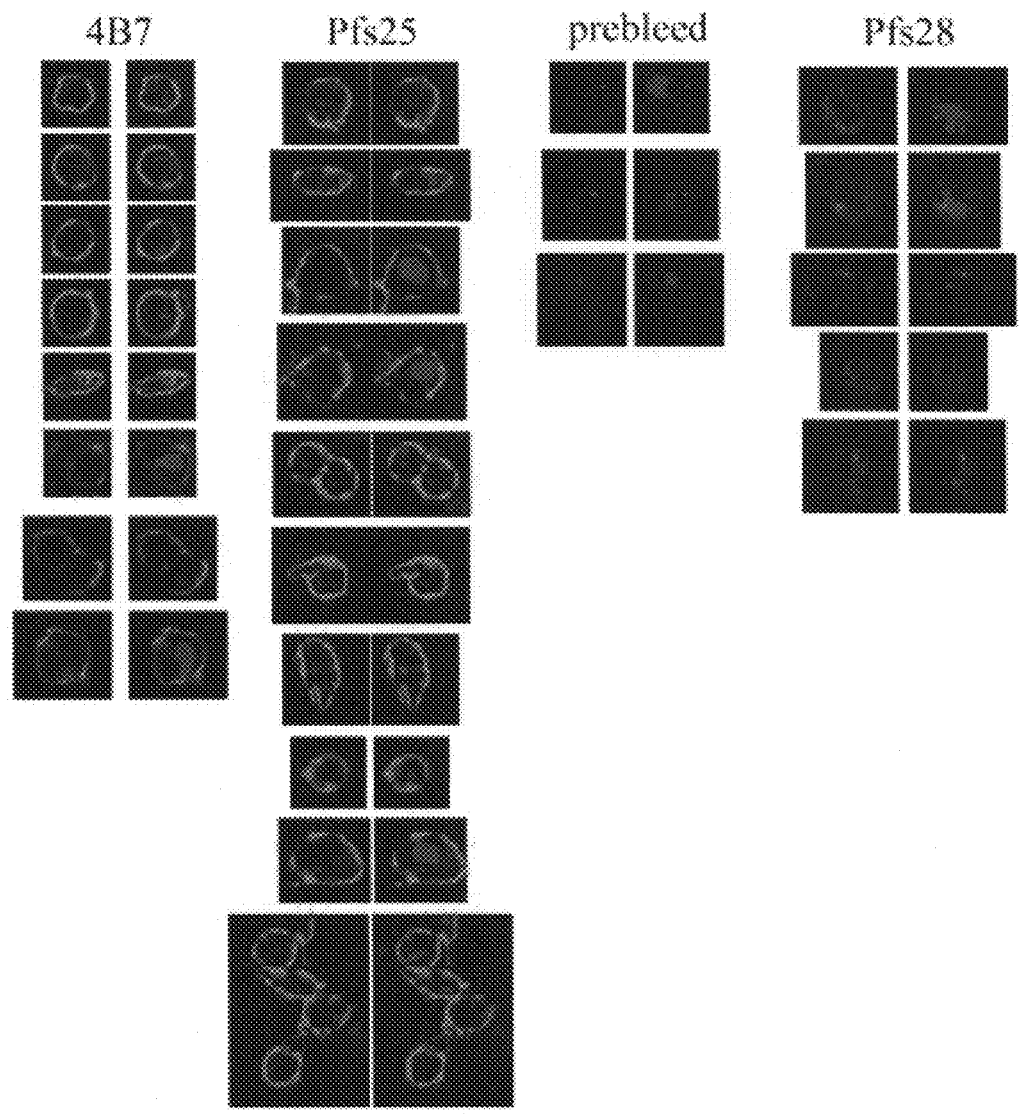

FIG. 20 illustrates indirect immunofluorescence using immune sera from mice injected with algae-produced Pfs25 or Pfs28 on in-vitro cultured P. falciparum gametocytes, gametes, and zygotes. DNA was stained using DAPI (blue) and antibody binding was visualized using Alexa Fluor 488-conjugated rabbit anti-mouse IgG (green) for a-Pfs25 antisera, a-Pfs28 antisera, anti-Pfs25 4B7 mAbs, and sera from isogenic unvaccinated mice.

Figure 21:
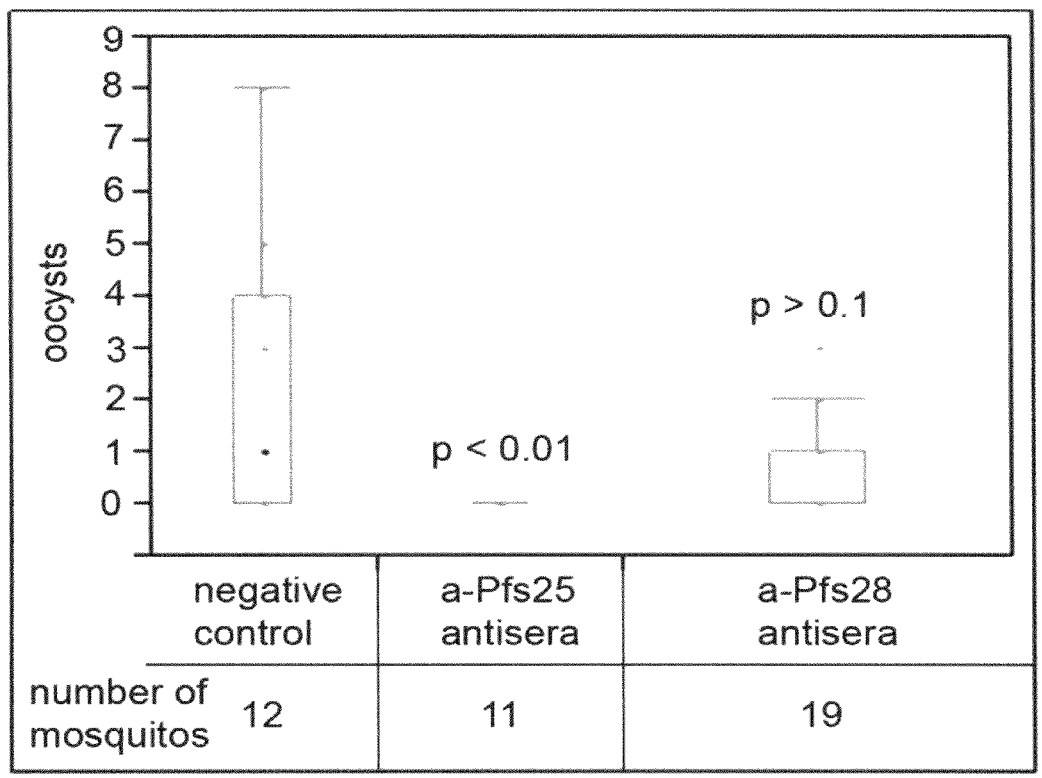

FIG. 21 illustrates standard membrane feeding assay with sera from mice immunized with algae-produced Pfs25 or Pfs28. Mosquitos midguts were dissected and analyzed for the presence of oocysts following SMFA. Oocyst numbers are presented as a boxplot. The total number of mosquitos analyzed is listed. Statistics were calculated with a single-tailed Wilcoxon nonparametric comparison.

Figure 22:
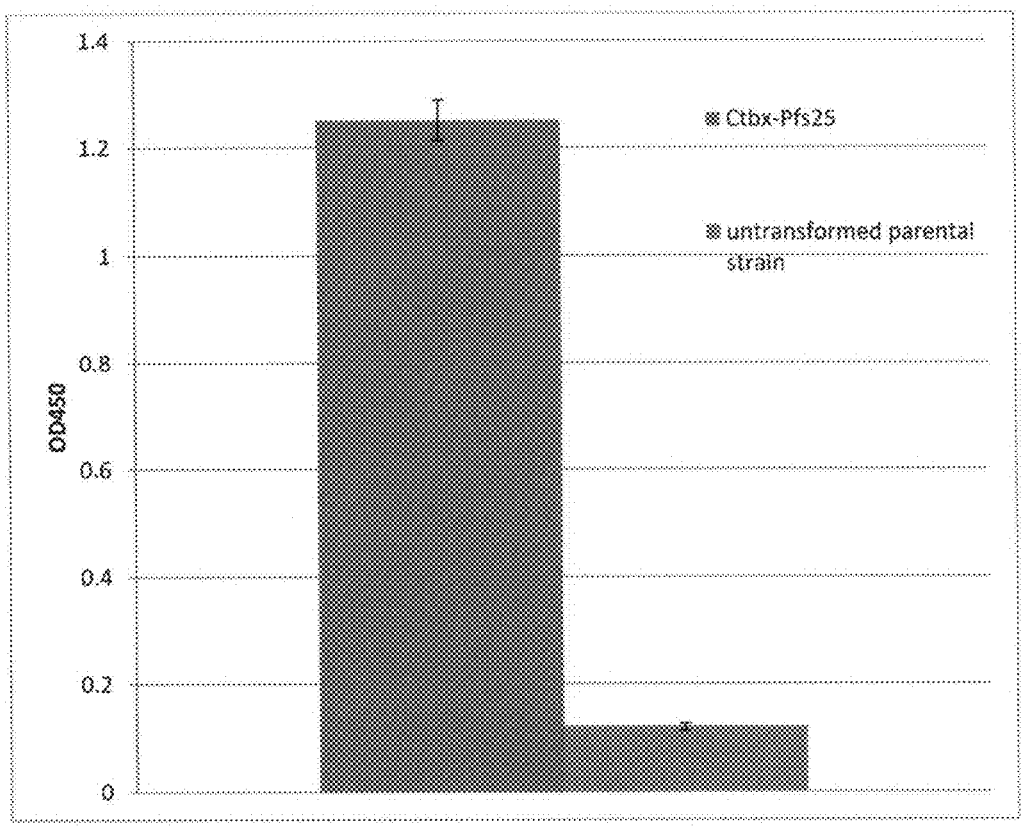

FIG. 22 illustrates the ability of the Ctbx-Pfs25 fusion protein to bind the GM1 receptor by ELISA. Ctbx binds to the GM1 ganglioside receptor on gut epithelial cells only when it folds correctly into a homopentamer. The β subunit of the toxin (Ctbx) from *Vibrio cholerae* is a potent mucosal adjuvant when co-administered with vaccine antigens. A nucleic acid encoding amino acids 22-121 of Ctbx (NCBI reference sequence YP_004937110.1), with codon bias for improved expression in algae, was fused to a nucleic acid encoding transmission *Plasmodium* immunogenic polypeptides Pfs25, Pfs28, Pfs48/45, Pfs230 or Hap2, with codon bias for improved expression in algae. Plates were coated with GM1 ganglioside receptor, blocked with 5% milk in PBS, and then incubated with lysates from algae strains with Ctbx-Pfs25 or the untransformed parental strain. Binding to the GM1 receptor was detected with rabbit anti-Ctbx antibodies followed by goat anti-rabbit-HRP and visualized with the TMB substrate and read at 450 nm on a Tecan plate reader.

DETAILED DESCRIPTION

1. Introduction

The present invention is based, in part, on the discovery and development of a process to make transmission blocking immunogenic proteins from malaria-causing *Plasmodium*, e.g., *Plasmodium falciparum*, in algal chloroplasts where they are correctly folded and disulfide bonds are formed, but the proteins are not glycosylated. Polypeptides produced by *Plasmodium* are not glycosylated. Therefore, recombinant proteins produced in algal host cells that also do not glycosylate proteins are more similar to the native *Plasmodium*-produced proteins. The native *Plasmodium* proteins have been shown to have transmission blocking activity against the spread of malaria. In order to create these proteins as a therapeutic vaccine candidate in an economically viable manner, it will be important to produce them in an inexpensive expression system, such as algal chloroplasts. Herein we demonstrate that algae are the first recombinant system to successfully produce unmodified and aglycosylated versions of *Plasmodium* surface proteins (e.g., P25, P28, P230 and P48/45). These antigens are structurally similar to the native proteins and antibodies raised to these recombinant proteins recognize Pfs25 and Pfs28 from *P. falciparum*. Furthermore, antibodies to algae-produced Pfs25 bind the surface of in-vitro cultured *P. falciparum* sexual stage parasites and exhibit transmission blocking activity.

Strategies for expression of *Plasmodium* polypeptides, particularly *Plasmodium* surface proteins (e.g., P25, P28, P230 and P48/45), in algal chloroplast is an important advancement because *Plasmodium* surface proteins have many disulfide bonds and are not glycosylated, two factors that have limited the use of more commonly employed protein expression systems, e.g., mammalian and prokaryotic systems. The algal chloroplast expression system overcomes these barriers and therefore represents an advantageous expression system to make these specific antigens.

Presently, *Plasmodium* surface proteins for the treatment and prevention of malaria are made in bacteria, then denatured and allowed to refold under oxidizing conditions, to allow disulfide bond formation. This is a cumbersome process and is not compatible with producing inexpensive vaccines, which malaria vaccines will need to be.

2. Transmission Blocking *Plasmodium* Antigens Subject to Expression in Algae Numerous *Plasmodium* antigens may find use in a vaccine that inhibits or prevents the transmission and/or continued life cycle of a *Plasmodium* parasite, and/or the progression of a *Plasmodium* parasitic infection. For example, antigens associate with the intra-mosquito stage (sexual stages), one can distinguish: antigen P27, P16, P25, P28, P48/45 or P230; for the intravascular (sporozoite) stage: antigen CSP-1, STARP, SALSA or SSP-2; for the intrahepatic stage: antigen LSA-1, EXP-1, LSA-3, STARP, SALSA or SSP-2; and for the intra-erythrocyte (merozoite) stage: antigen RAP-1, RAP-2, SERA-1, MSP-1, MSP-2, MSP-3, MSP-4, MSP-5, AMA-1, EMP-1, Pf35, Pf55 or EBA-175. *Plasmodium* polypeptides, including without limitation, CDPK4, HAP2, MAPK-2, MDV 1/Peg3, P47, P48/45, P230, PKG, AP2-0, DOZI, HMGP2, Nek-4, CelTOS, CDPK3, Chitinase, CTRP, IMC1b, MAOP, P25, P28, SOAP, Cap380, CSP, ECP1, IMC1a, LAP1/CCp3/SR, LAP2/CCp1, LAP3/CCp5, LAP4/CCp2, LAPS/FNPA, LAP6/CCp4, transglutaminase, CSP, CRMP1, CRMP2, MAEBL, TRAP, and UOS3/TREP/S6, and immunogenic fragments thereof, also find use.

The *Plasmodium* polypeptides, or immunogenic fragments thereof, can be from any member of the genus *Plasmodium* that causes malaria. For example, in various embodiments, the *Plasmodium* polypeptides, or immunogenic fragments thereof, are from *Plasmodium falciparum*, *Plasmodium vivax*, *Plasmodium ovale*, *Plasmodium malariae*, *Plasmodium chabaudi*, *Plasmodium berghei*, *Plasmodium knowlesi*, *Plasmodium reichenowi* or *Plasmodium yoelii*.

In some embodiments, the transmission blocking antigens are one or more *Plasmodium* surface proteins, e.g., expressed on the surface of a gamete, zygote, ookinete, oocyst or sporozoite. In some embodiments, the transmission blocking antigens are selected from P48/45, P25, P28, P230, HAP2, and/or immunogenic fragments thereof. In some embodiments, the *Plasmodium* antigens are surface proteins from *Plasmodium falciparum*, e.g., Pfs48/45, Pfs25, Pfs28, Pfs230 or immunogenic fragments thereof. For example, in some embodiments, the nucleic acid encodes a fragment of P25 no longer than amino acid residues 22-193 of P25. In some embodiments, the nucleic acid encodes a fragment of P28 no longer than amino acid residues 23-179 of P28. In some embodiments, the nucleic acid encodes a fragment of P28 no longer than amino acid residues 23-193 of P28. In some embodiments, the nucleic acid encodes a fragment of P48/45 no longer than amino acid residues 178-448 of P48/45.

Polynucleotides encoding one or more *Plasmodium* polypeptides, or immunogenic fragments thereof, can be altered for improved expression in an algal host cells. For example, codons in the wild-type polynucleotides encoding one or more *Plasmodium* polypeptides rarely used by the algal host cell can be replaced with a codon coding for the same or a similar amino acid residue that is more commonly used by the algal host cell (i.e., employing algal chloroplast codon bias), thereby allowing for more efficient expression of the *Plasmodium* polypeptide and higher yields of the expressed *Plasmodium* polypeptide in the algal host, in comparison to expression of the *Plasmodium* polypeptide from the wild-type polynucleotide. Methods for altering polynucleotides for improved expression in an algal host cell, particularly in a *Chlamydomonas reinhardtii* host cell, are known in the art and described in, e.g., Franklin et al (2002) *Plant J* 30:733-744; Fletcher, et al., *Adv Exp Med. Biol.* (2007) 616:90-8; Heitzer, et al., *Adv Exp Med. Biol.* (2007) 616:46-53; Rasala and Mayfield, *Bioeng Bugs.* (2011) 2(1): 50-4; Rasala, et al, *Plant Biotechnol J.* (2010) 8(6):719-33;

Wu, et al., *Bioresour Technol.* (2011) 102(3):2610-6; Morton, *J Mol Evol.* (1993) 37(3):273-80; Morton, *J Mol Evol.* (1996) 43(1):28-31; and Morton, *J Mol Evol.* (1998) 46(4):449-59.

In various embodiments, polynucleotide sequences encoding *Plasmodium* surface polypeptides can be improved for expression in algae by changing codons that are not common in the algae host cell (e.g., used less than ~20% of the time). For improved expression of polynucleotide sequences encoding *Plasmodium* surface polypeptides in *C. reinhardtii* host cells, codons rare or not common to the chloroplast of *C. reinhardtii* in the native *Plasmodium* nucleic acid sequences are reduced or eliminated. A representative codon table summarizing codon usage in the *C. reinhardtii* chloroplast is found on the internet at kazusa.or.jp/codon/cgi-bin/showcodon.cgi?species=3055.chloroplast. In various embodiments, preferred or more common codons for amino acid residues in *C. reinhardtii* are as follows:

| Amino Acid Residue | Preferred codons for improved expression in algae |
| --- | --- |
| Ala | GCT, GCA |
| Arg | CGT |
| Asn | AAT |
| Asp | GAT |
| Cys | TGT |
| Gln | CAA |
| Glu | GAA |
| Gly | GGT |
| Ile | ATT |
| His | CAT |
| Leu | TTA |
| Lys | AAA |
| Met | ATG |
| Phe | TTT |
| Pro | CCA |
| Ser | TCA |
| Thr | ACA, ACT |
| Trp | TGG |
| Tyr | TAT |
| Val | GTT, GTA |
| STOP | TAA |

In certain instances, less preferred or less common codons for expression in an algae host cell can be included in a polynucleotide sequence encoding a *Plasmodium* surface polypeptide, for example, to avoid sequences of multiple or extended codon repeats, or sequences of reduced stability (e.g., extended A/T-rich sequences), or having a higher probability of secondary structure that could reduce or interfere with expression efficiency. In various embodiments, the polynucleotide sequence can be synthetically prepared. For example, the desired amino acid sequence of a *Plasmodium* surface polypeptide (e.g., a P48/45, P25, P28, P230 or HAP2 polypeptide) can be entered into a software program with algorithms for determining codon usage for an algal host cell. Illustrative software includes GeneDesigner available from DNA 2.0, on the internet at dna20.com/genedesigner2.

Exemplary polynucleotides, altered for improved expression of *Plasmodium* surface polypeptides in an algal host cell, for example, a *Chlamydomonas* host cell, for example, a *Chlamydomonas reinhardtii* host cell, are provided as SEQ ID NOs:1-9, 11, 13, 16, herein. Polynucleotides having at least about 60% sequence identity to any one of SEQ ID NOs: 1-9, 11, 13, 16, 34 and/or 36, for example, at least about 65%, 70%, 75%, 80%, 85%, 90%, 95%, 98% or 99% sequence identity to any one of SEQ ID NOs: 1-9, 11, 13, 16, 34 and/or 36 can be integrated into the chloroplast genome of the algal host cell for expression of the encoded *Plasmodium* surface polypeptide(s).

In various embodiments, two or more *Plasmodium* polypeptides, or immunogenic fragments thereof, are expressed as a fusion protein.

In some embodiments, the *Plasmodium* polypeptides are fused to one or more tags, e.g., to facilitate purification (e.g., poly-His, SBP, FLAG), detection (e.g., FLAG, GFP), expression, stability (e.g., SUMO, Tic40), and/or delivery (e.g., CTB, LTB). Illustrative tags include without limitation poly-His, Mistic, serum amyloid A (SAA), Tic40, small ubiquitin modifier peptide (SUMO), Streptavidin-Binding Peptide (SBP), green fluorescent protein (GFP), FLAG, cholera toxin beta subunit (CTB), and heat-labile enterotoxin beta subunit (LTB).

The tags can be positioned at the N-terminal end, at the C-terminal end, or within or between the *Plasmodium* polypeptides. For example, in various embodiments, SUMO or Tic40 can be positioned N-terminal to the *Plasmodium* polypeptide and CTB and/or LTB can be positioned C-terminal to the *Plasmodium* polypeptide. The SUMO tag or Tic40 tag can be removed prior to isolation and/or purification. Such a configuration facilitates expression efficiency and stability of the *Plasmodium* polypeptide and allows for more efficient delivery across mucosal surfaces (e.g., for oral administration of the vaccine).

3. Formulation and Administration

The nucleic acids and polypeptides of the present invention are also useful as prophylactics, or vaccines, for blocking transmission of malaria or other diseases caused by parasites. Compositions containing the algal-produced *Plasmodium* polypeptides, nucleic acids or a cocktail thereof are administered to a subject, giving rise to an immune response in the mammal entailing the production of antibodies against the *Plasmodium* polypeptide immunogens (e.g., P25, P28, P48/45, P230, HAP2, and immunogenic fragments thereof). The immunoglobulins against the *Plasmodium* polypeptide immunogens then block transmission of the parasite from the subject to the arthropod vector, preventing the parasite from completing its life cycle. An amount of prophylactic composition sufficient to result in a titer of antiserum which, upon ingestion by the mosquito, is capable of blocking transmission or is capable of decreasing ability of the oocyte to mature in the mosquito (resulting in fewer infective particles passed to the mosquitoes' next target bloodmeal), is defined to be an "immunologically effective dose."

The algal-produced *Plasmodium* polypeptides and/or nucleic acids suitable for expression of *Plasmodium* polypeptides in an algal host cell can be used in pharmaceutical and vaccine compositions for administration to mammals and other susceptible organisms, particularly humans, to block transmission of *Plasmodium* and prevent the perpetuation of the *Plasmodium* life cycle in a host subject. The compositions are suitable for single administrations or a series of administrations. When given as a series, inoculations subsequent to the initial administration are given to boost the immune response and are typically referred to as booster inoculations. In various embodiments, the algal-produced *Plasmodium* polypeptides are administered to the susceptible host within an algal cell or population of algal cells. The algal cells can, but need not be, intact. In various embodiments, the algal cells are freeze dried. Usually, the algal cells comprising one or more algal-expressed *Plasmodium* polypeptides are administered orally to the subject. In such cases, the *Plasmodium* polypeptides may be expressed as a fusion protein with a delivery tag, e.g., a cholera toxin beta subunit (CTB) or a heat-labile enterotoxin beta subunit (LTB).

The pharmaceutical compositions of the invention are intended for parenteral, topical, oral or local administration.

In various embodiments, the pharmaceutical compositions are administered parenterally, e.g., intravenously, subcutaneously, intradermally, or intramuscularly. Thus, the invention provides compositions for parenteral administration that comprise a solution of the agents described above dissolved or suspended in an acceptable carrier, preferably an aqueous carrier. A variety of aqueous carriers may be used, e.g., phosphate buffered saline, water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient and more preferably at a concentration of 25%-75%.

For aerosol administration, the polypeptides or nucleic acids are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

In therapeutic applications, algal-produced *Plasmodium* polypeptides and/or nucleic acids suitable for expression of *Plasmodium* polypeptides in an algal host cell are administered to a patient in an amount sufficient to prevent parasite development in the arthropod and thus block transmission of the disease. An amount adequate to accomplish this is defined as a "therapeutically effective dose." Amounts effective for this use will depend on, e.g., the particular polypeptide, the manner of administration, the weight and general state of health of the patient, and the judgment of the prescribing physician.

The vaccines of the invention contain as an active ingredient an immunogenically effective amount of the algal-produced *Plasmodium* polypeptide(s), nucleic acids, as described herein. Useful carriers are well known in the art, and include, e.g., thyroglobulin, albumins such as human serum albumin, tetanus toxoid, polyamino acids such as poly (D-lysine:D-glutamic acid), influenza, hepatitis B virus core protein, hepatitis B virus recombinant vaccine and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art.

Vaccine compositions containing the polypeptides or nucleic acids of the invention are administered to a patient to elicit a transmission-blocking immune response against the antigen and thus prevent spread of the disease through the arthropod vector. Such an amount is defined as an "immunogenically effective dose." In this use, the precise amounts again depend on the patient's state of health and weight, the mode of administration, and the nature of the formulation.

4. Assays for Transmission Blocking

Methods of quantifying transmission-blocking antibodies in vitro is known in the art and described, e.g., in Quakyi, et al., *J. Immunol*. (1987) 139:4213. Briefly, mosquitoes are fed on *Plasmodium*-parasitized material (either infected blood or mature ookinetes mixed with naive blood) through a membrane. Infectivity is measured 1 week after feeding by counting the number of oocysts per mosquito midgut of 20 mosquitoes. By adding post-immunization mouse sera (diluted in heat-inactivated normal chicken serum) to the parasitized blood, the effect of the sera on parasite transmission is measured. If the addition of immune sera reduced infectivity compared with the control, then the immune sera demonstrated the presence of transmission-blocking antibodies. Further exemplary transmission-blocking assays are described, e.g., in Roeffen, et al., *Infect Immun*. (1995) 63(2): 467-71; Read, et al., *Parasite Immunol*. (1994) 16(10):511-9; and Kaslow, *Curr Opin Immunol*. (1993) 5(4):557-65.

5. Methods of Expressing Transmission Blocking *Plasmodium* Antigens in Unicellular Green Algae The *Plasmodium* polynucleotides encoding *Plasmodium* polypeptides, and immunogenic fragments thereof, are expressed in and produced from an algal host cell, particularly a unicellular green algae host cell, particularly an algae of the genus *Chlamydomonas*, in particular *Chlamydomonas reinhardtii*. An algal host cell of the genus *Chlorella*, in particular *Chlorella vulgaris* also finds use.

The chloroplasts of algal host cells are transformed, e.g., by homologous recombination techniques, to contain and stably express one or more polynucleotides encoding one or more *Plasmodium* polypeptides or an immunogenic fragment thereof, as described herein, integrated into the chloroplast genome.

Transformation of the chloroplasts of algal host cells can be carried out according to techniques well known to those persons skilled in the art. Examples of such techniques include without limitation electroporation, particle bombardment, cytoplasmic or nuclear microinjection, gene gun. See, e.g., FIG. 2.

Expression of the *Plasmodium* polypeptides in the algal host cell can be detected using any method known in the art, e.g., including immunoassays (ELISA, Western Blot) and/or nucleic acid assays (RT-PCR). Sequences of expressed polypeptides can be confirmed using any method known in the art (e.g., mass spectrometry).

*Plasmodium* polypeptides expressed in an algal host cell are generally properly folded without performing denaturation and refolding. Furthermore, the polypeptides are not glycosylated, so coding sequences do not need to be altered to remove glycosylation sites and glycosylated moieties do not need to be removed post-translationally.

Recombinant expression of proteins from heterologous polynucleotides incorporated into the chloroplast genome of an algal host cell, particularly an algal host cell of the genus *Chlamydomonas*, in particular *Chlamydomonas reinhardtii*, is known in the art and described in numerous publications, including, e.g., in Rasala and Mayfield, *Bioeng Bugs*. (2011) 2(1):50-4; Rasala, et al., *Plant Biotechnol J*. (2011) May 2, PMID 21535358; Coragliotti, et al., *Mol. Biotechnol*. (2011)

48(1):60-75; Specht, et al., *Biotechnol Lett.* (2010) 32(10): 1373-83; Rasala, et al., *Plant Biotechnol J.* (2010) 8(6):719-33; Mulo, et al., *Biochim Biophys Acta*. (2011) May 2, PMID: 21565160; and Bonente, et al., *Photosynth Res*. (2011) May 6, PMID:21547493.

EXAMPLES

The following examples are offered to illustrate, but not to limit the claimed invention.

Example 1

Heterologous Expression of the C-Terminal Antigenic Domain of the Malaria Vaccine Pfs48/45 in the Green Algae *Chlamydomonas reinhardtii*

Materials and Methods
Materials and Methods
  Plasmid Construction.
  The amino acid sequence for Pfs48/45 was obtained from the National Center for Biotechnology Information (NCBI). Nucleotides representing amino acids 27-448 of this gene were sequenced de novo using codon bias for the *C. reinhardtii* chloroplast with the addition of a C-terminal Flag sequence (5'-GATTATAAAGATGATGATGACAAA-3' (SEQ ID NO: 40) and restriction sites NdeI, AgeI and XbaI (GeneArt).
  Plasmids D1 and D2 were constructed using vectors previously optimized for expression in the chloroplast of *C. reinhardtii* (Manuell et al (2007) *Plant Biotech. J.* 5:402-412; Barnes et al (2005) *Mol. Gen. Genom.* 274:625-636). D1 homologously recombines in the region of the psbA gene using kanamycin selection and contains the promoter and 5'UTR for psbA as well as the 3'UTR for psbA. D2 recombines in the region of psbH under photosynthetic selection and contains the promoter and 5'UTR for psbD and the 3'UTR for psbA. Nucleotide fragments prepared by Hi-Fidelity PCR and restriction enzyme digestion were used to clone nucleotide sequences containing variations in two expression tags (Flag and Serum Amyloid A protein (SAA)) and four c.r.Pfs48/45 nucleotide regions representing various amino acid lengths of the c.r.Pfs48/45 gene (including 27-448, 27-426, 178-427, and 178-448). These plasmids were transformed into *Escherichia coli* and verified by restriction digestion and nucleotide sequencing (Retrogen and Eton Biosciences).
  Algal Strains, Transformation and Growth Conditions.
  Three algal strains were used for transformations, including *C. reinhardtii* wildtype (w/t) strain 137c (Mt+) (CC-125, The *Chlamydomonas* Core-Collection Center, Duke University), *C. reinhardtii* psbA mutant strain (W1.1) (Manuell et al (2007) Plant Biotech. J. 5:402-412) and *C. reinhardtii* non-photosynthetic psbH mutant strain (psbH-) (Rasala et at (2011) *Plant Biotech. J.* 9:674-683). Prior to transformation, all strains were grown to mid logarithmic phase (approximately $8 \times 10^5$ to $2 \times 10^6$ cells/mL) in TAP (Tris-acetate-phosphate) medium at 29° C. on a rotary shaker. Cells were harvested using centrifugation and resuspended using TAP medium at a concentration of $3 \times 10^7$ cells/mL. Both w/t and W1.1 strains were plated on TAP solid medium containing 150 mg/mL kanamycin. The psbH-strain was plated on HSM (High Salt Medium) solid medium. Approximately $1.5 \times 10^7$ cells were plated for each transformation.
  About 10 µg of plasmid DNA was prepared for each construct. This DNA was bound to gold particles (Seashell Technology) and 10 µL of the DNA/gold mixture was added to a carrier membrane and used for particle bombardment transformation. D1-based constructs were transformed on to individual plates containing W1.1 and w/t strains separately while D2-based constructs were only transformed on to plates containing the psbH-strain. Following transformation, plates containing W1.1 and w/t strains were placed under low constant illumination while plates containing the psbH-strain were placed under high constant illumination to allow for the formation of transformed colonies. These plates were allowed to grow under these light conditions for two to four weeks before colonies were assessed.
  PCR Screening.
  Successful transformants were initially identified based on primary selection measures. For w/t and W1.1 transformed strains, colonies with kanamycin resistance grew following the loss of non-resistant background, and for the psbH-strain colonies grew that were capable of photosynthesis under the high-light conditions. Colonies were patched on to their respective solid medium plates (W1.1 and w/t were plated on TAP medium containing 100 µg/mL kanamycin) and allowed to grow for about 1-2 weeks. These colonies were then screened using primer specific PCR to identify the insertion of the Pfs48/45 gene (5'-GTGCTAGGTAAC-TAACGTTTGATTTTT-3' (SEQ ID NO: 41) and 5'-AATAT-TACTTGGTTCTAATTCTTC-3' (SEQ ID NO: 42)). Colonies found to contain the Pfs48/45 gene were plated on to a fresh solid medium plate containing their respective antibiotics. These Pfs48/45 strains were repeatedly screened by PCR using primer sets designed to indicate the loss of the endogenous *C. reinhardtii* chloroplast gene compared to a control region. These strains were continuously screened and replated about every 1-2 weeks until homoplasmic lines were identified.
  RNA Isolation & cDNA Analysis.
  For RNA isolation, algal cultures were grown to a concentration of about $5 \times 10^5$ cells/mL under low light conditions and then induced under high light conditions for 24 hours. Following this 24-hour period, 10 mL of algal cells were centrifuged and resuspended in 0.5 mL of Plant RNA reagent. Following separation and chloroform extraction, RNA was treated with isopropyl alcohol and washed with ethanol. The RNA pellet was then resuspended in RNase free water. RNA was treated to remove genomic DNA using the Ambion Turbo DNA-free kit and resuspended in 20-50 µL of RNase free water. RNA was quantified and 500 ng of the RNA was used for cDNA synthesis using the Biorad iScript cDNA synthesis kit. cDNA was then used in a standard PCR reaction using Pfs48/45 primers (5'-CATGGTTGTAATTTCTCATC-3' (SEQ ID NO: 43) and 5'-GATTCTGGTTGATATACTTG-3' (SEQ ID NO: 44)) and rbcL control primers (5'-AGCAGGT-GCTGGATTCAAAG-3' (SEQ ID NO: 45) and 5'-CAGCTA-CAGCAGCACCACAT-3' (SEQ ID NO: 46)). PCR products were analyzed on a 1% agarose gel containing ethidium bromide.
  Protein Expression, Purification and Western Blot Analysis.
  Algal cultures were grown to a concentration of about $8 \times 10^5$ cells/mL under low light conditions and then induced under high light conditions for 24 hours. Following this 24-hour period, algal cells were centrifuged and resuspended in lysis buffer (50 mM Tris-HCl, pH 8.0; 500 mM NaCl; 0.5% Tween-20). Cells were sonicated and centrifuged at 13,000 rpm for 15 minutes. The soluble protein fraction was incubated overnight with FLAG resin at 4° C. on an end-over-end shaker. Resin was rinsed twice with lysis buffer and once with 1×TBS before elution with six column volumes of elution buffer into a microcentrifuge tube containing 1:20 1 M Tris- HCl, pH 8.0. The total, soluble and eluted protein fractions were then analyzed using Western Blot. Proteins were separated on RunBlue 12% PAGE gels (Expedeon) and transferred to Nitrocellulose membranes for Western analysis. Membranes were blocked with 5% dry milk resuspended in 1×TBS for 2 hours. An anti-FLAG antibody preconjugated with Alkaline Phosphatase (Monoclonal Anti-FLAG M2-Alkaline Phosphatase M2, Sigma Aldrich) was added to the solution at a concentration of 1:5000 and allowed to incubate at 4° C. overnight. The blots were rinsed with 1×TBS and then developed using nitro-blue tetrazolium (NBT) and 5-bromo-4-chloro-3'-indoylphosphate (BCIP) in 1×AP buffer.

Conformation Western Blot and Elisa Assays.

Equivalent amounts of eluted Pfs48/45 protein were separated on RunBlue 12% PAGE gels. Reduced samples were prepared by adding 160 mM urea, 490 mM DTT and heating at 60° C. for 15 minutes while non-reduced samples contained only the native protein loading dye (62.5 mM Tris-HCl, pH 6.8; 40% glycerol; 0.01% bromophenol blue, Bio-rad). The gel was run using a non-reducing running buffer (800 mM Tricine, 1.2 M Tris, 69.4 mM SDS). Proteins were subsequently transferred to nitrocellulose membranes. These membranes were then cut into quarters to allow for analysis with both anti-FLAG and anti-Pfs48/45 and to ensure even antibody incubation within each sector of the Western blot. After blocking with 5% milk, anti-FLAG antibody (Monoclonal Anti-FLAG M2, Sigma Aldrich) was added at a concentration of 1:5000 and the Pfs48/45 conformation-specific antibody anti-Pfs48/45 IIC5-10 MRA-26 (Malaria Research and Reference Reagent Resource Center) was added at a concentration of 1:1000 to the respective blot sections. Following overnight incubation at 4° C., all blots were rinsed in 1×TBS and then incubated for 2 hours at room temperature with the anti-mouse secondary antibody preconjugated with alkaline phosphatase (Anti-mouse IgG AP conjugate; Sigma Aldrich). These blots were then rinsed and developed using NBT and BCIP in 1×AP buffer.

Enzyme-linked immunosorbent assays (ELISA) were completed following protein quantification using a Lowry assay. The 8 µg of eluted protein was separated into two aliquots prior to plating on Nunc Blot 96-well plates. The first aliquot was suspended in 1×PBS and treated with 175 mM urea and 630 mM DTT as well as heated to 60° C. for 15 minutes while the second aliquot was suspended in an equivalent total volume of 1×PBS. Protein solutions were allowed to incubate on the plate overnight at 4° C. before being removed and the wells rinsed with 1×PBS. Primary anti-FLAG antibody at a concentration of 1:6000 and MRA-26 at a concentration of 1:1000 were resuspended in 1×PBS and added to each respective well. These were incubated for 4 hours before being removed and the wells rinsed with 1×PBS. Secondary anti-mouse-HRP antibody (Stabilized Goat Anti-Mouse IgG Peroxidase Conjugated; Thermo Scientific) was added at a concentration of 1:20,000 and incubated for 2 hours at room temperature. These wells were then rinsed 4 times with 1×PBS before being developed with (TMB Substrate Kit; Thermo Scientific). The plates were then analyzed on a plate reader at 450 nm.

Mass Spectrometry.

Elution aliquots of protein obtained from strain 391 were used for mass spectrometry identification of the Pfs 48/45 amino acid sequence. Pfs48/45 protein solution (0.3 mg/ml in 50 mM Hepes buffer, pH 7.2) was reduced and alkylated using 1 mM Tris(2-carboxyethyl) phosphine (Fisher, AC36383) at 94° C. for 5 minutes and 2.5 mM iodoacetamide (Fisher, AC12227) at 37° C. in dark for 30 minutes, respectively. Proteins were digested on beads with 1 ug trypsin (Roche, 03 708 969 001) at 37° C. overnight.

Nanoflow LC-MS/MS analysis was performed using LTQ tandem mass spectrometer (Thermo Electron Corporation, San Jose, Calif.) employing automated data-dependent acquisition. An Agilent 1100 HPLC system (Agilent Technologies, Wilmington, Del.) was used to deliver a flow rate of 500 mL min-1 to the mass spectrometer through a splitter. Using an in-house constructed pressure cell, 5 µm Zorbax SB-C18 (Agilent) packing material was packed into a fused silica capillary tubing (200 µm ID, 360 µm OD, 20 cm long). One end of the fused silica tubing was pulled to a sharp tip using a laser puller (Sutter P-2000) as the electro-spray tip. The peptide mixture was loaded onto the HPLC column using the same in-house pressure cell. Peptides were eluted from the HPLC column using a 0 to 80% acetonitrile gradient for 120 minutes. Mass spectrometer was programmed to perform data-dependent MS/MS scans on the 7 most intense ions from the full MS scan (450-2000 Da).

Raw data were extracted and searched using Spectrum Mill (Agilent, version A.03.02.060b). MS/MS spectra with a sequence tag length of 1 or less were considered as poor spectra and discarded. The filtered of the MS/MS spectra were searched against a database containing the Pfs48/45 protein sequence and common contaminants including trypsin and keratin. The enzyme parameter was limited to full tryptic peptides with a maximum mis-cleavage of 1. All other search parameters were set to SpectrumMill's default settings (carbamidomethylation of cysteines, +/−2.5 Da for precursor ions, +/−0.7 Da for fragment ions, and a minimum matched peak intensity of 50%). Oxidized-Methionine and pyro-Glutamate was defined as variable modifications. A maximum of 2 modifications per peptide was used.

Results

Figure 1:
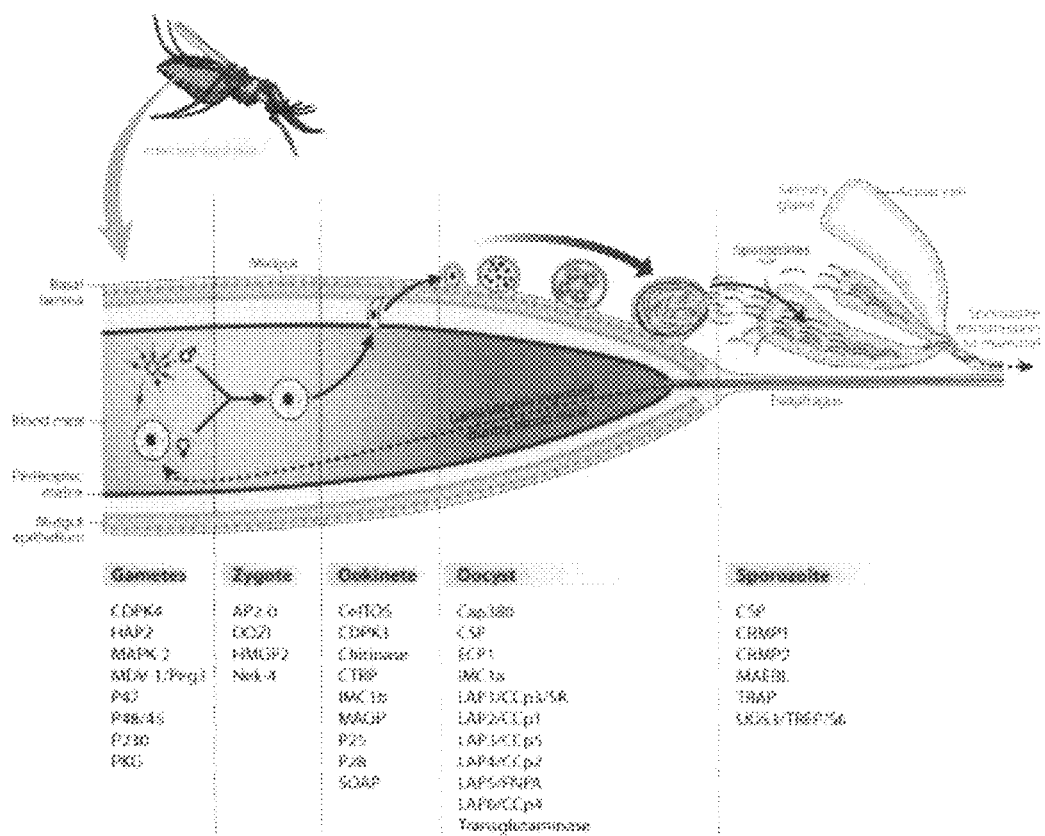
FIG. 1 illustrates *Plasmodium* polypeptides useful as transmission blocking vaccines and that can be expressed in the unicellular green algae expression systems described herein. *Plasmodium* polypeptides useful as transmission blocking vaccines are reviewed in, e.g., Aly, et al., *Annu Rev Microbiol.* 2009; 63:195-221.
Figure 2:
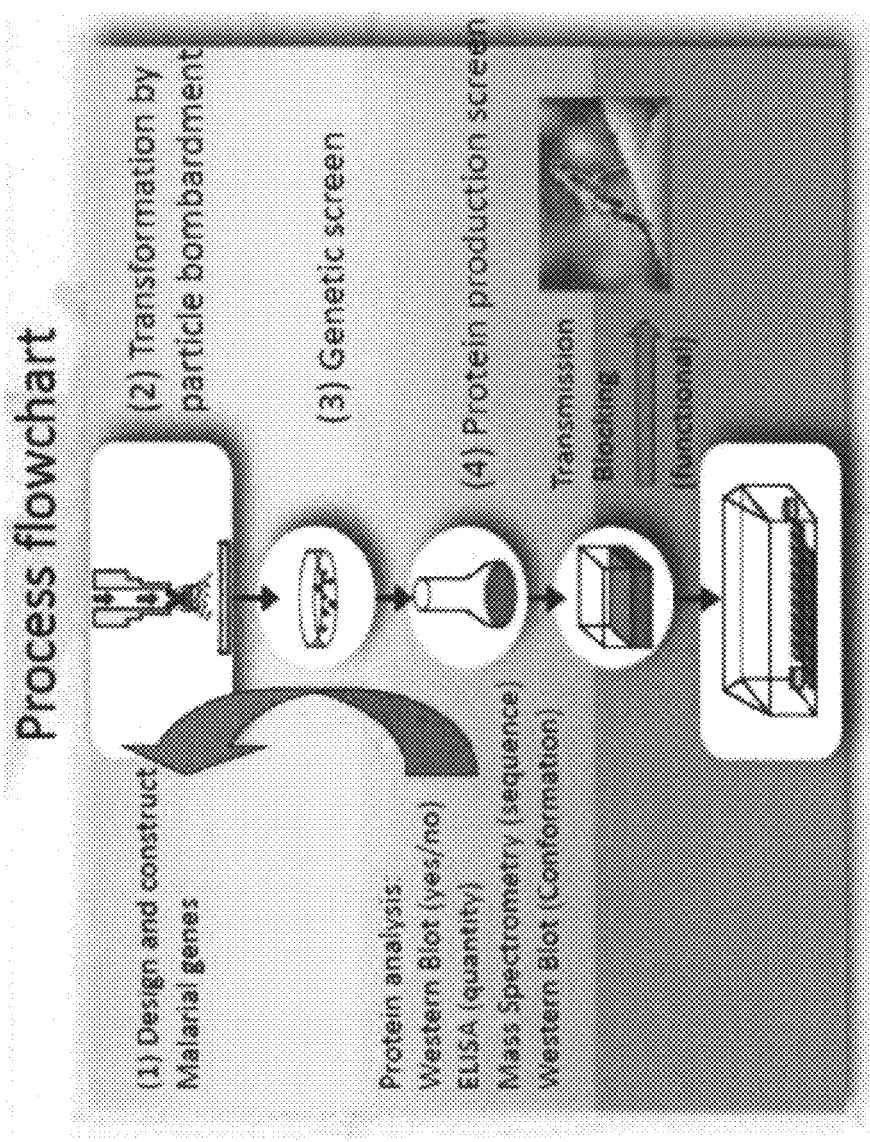
FIG. 2 illustrates a process flowchart for producing *Plasmodium* polypeptides useful as transmission blocking vaccines in unicellular green algae.
Figure 3:
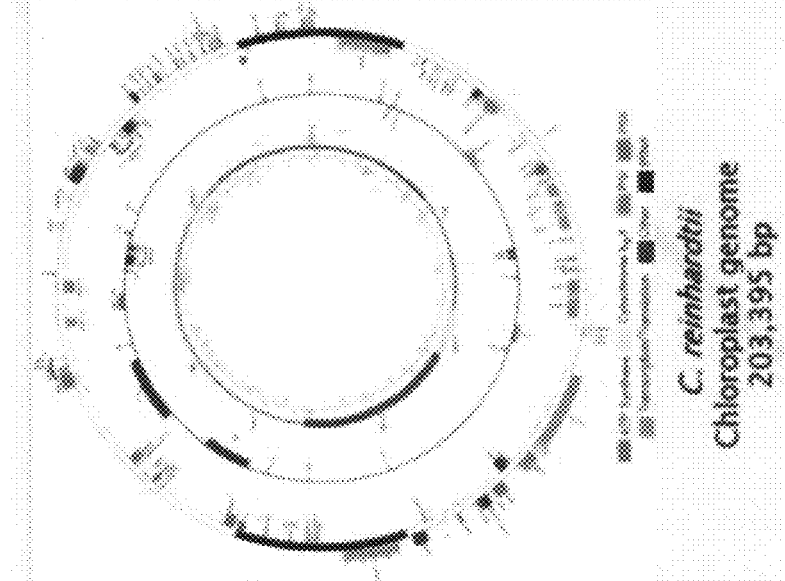
FIG. 3 illustrates the advantages of engineering the algal chloroplast for the production of *Plasmodium* polypeptides useful as transmission blocking vaccines.
Figure 4:
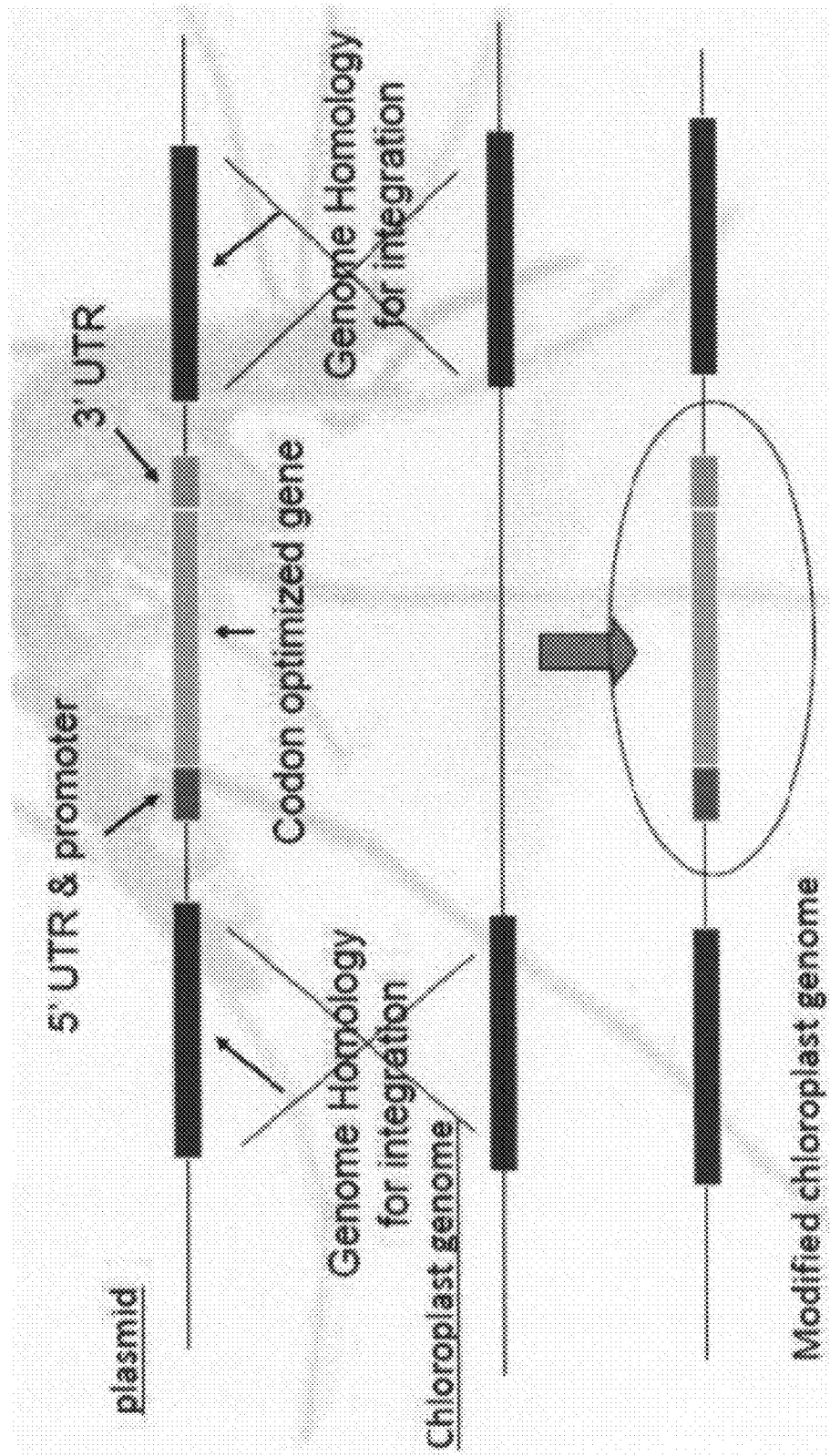
Figure 5:
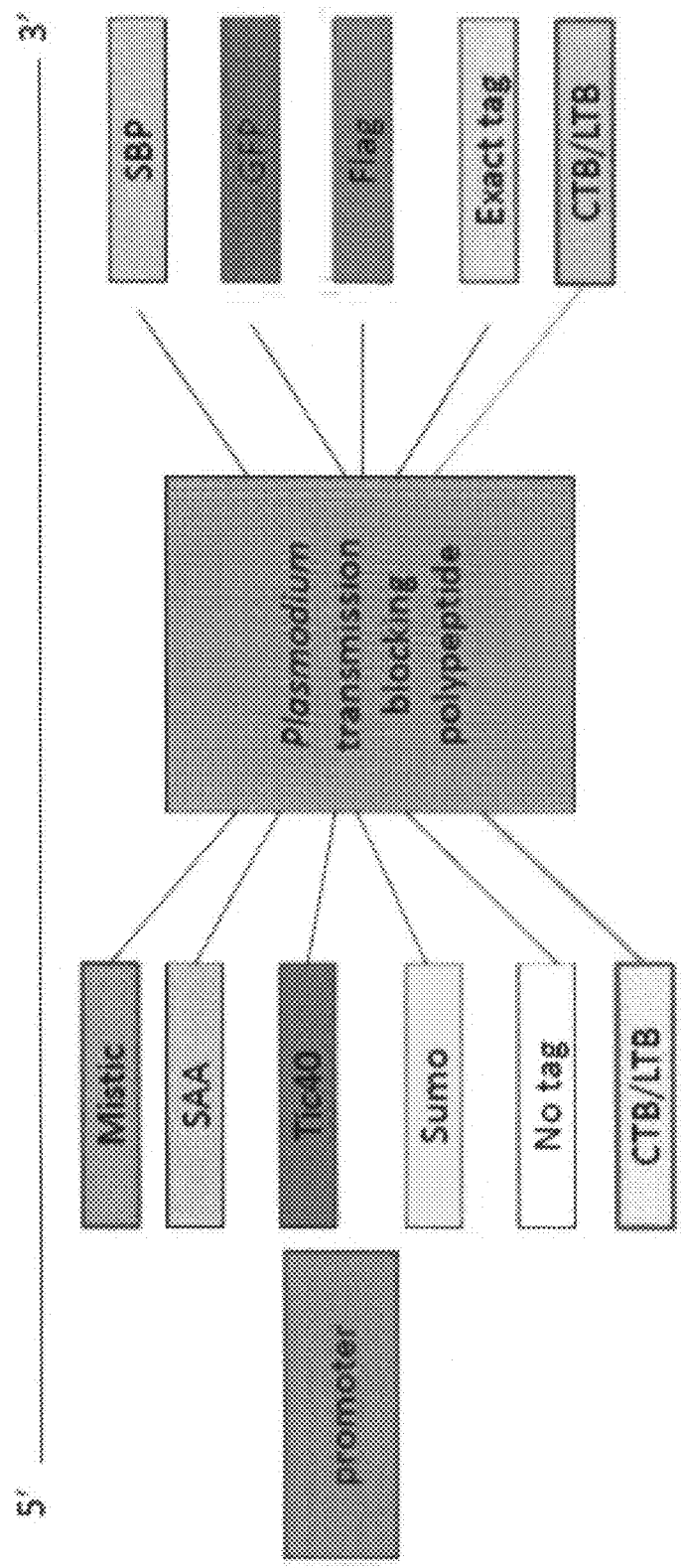
Figure 6:
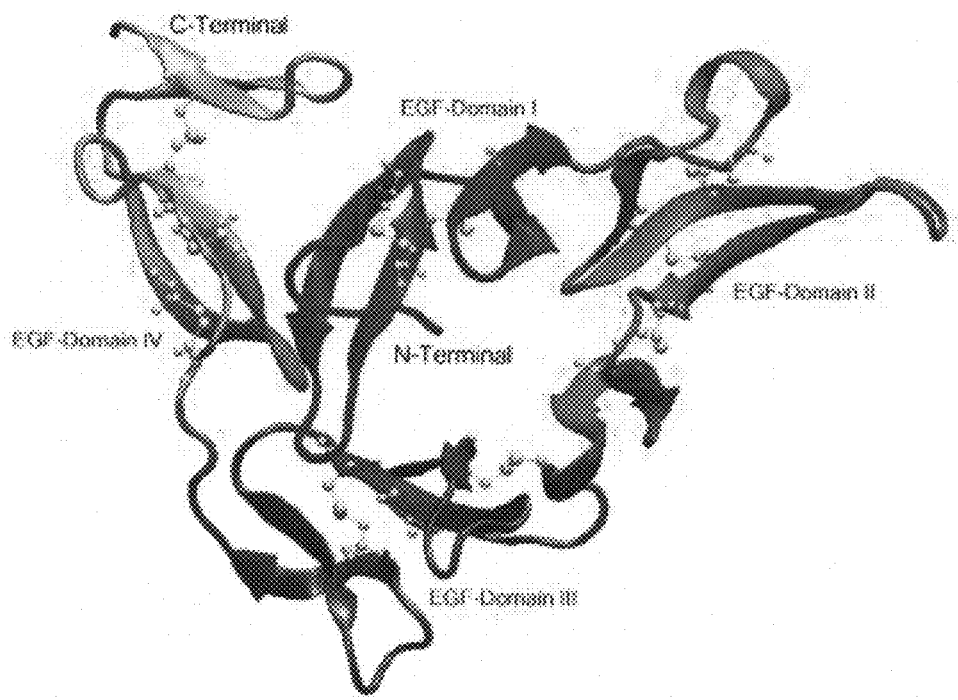
Figure 6:
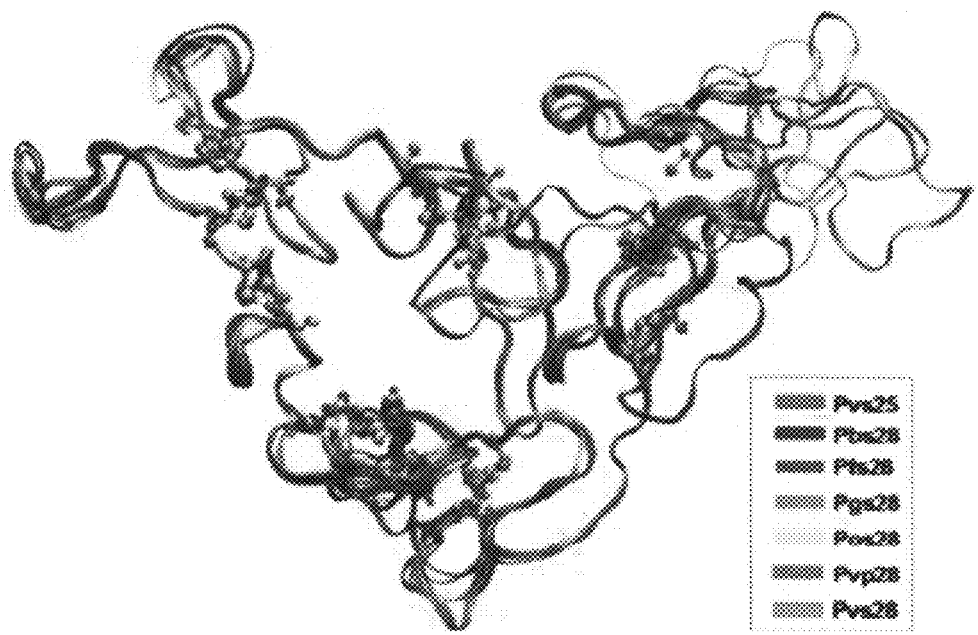
Figure 7:
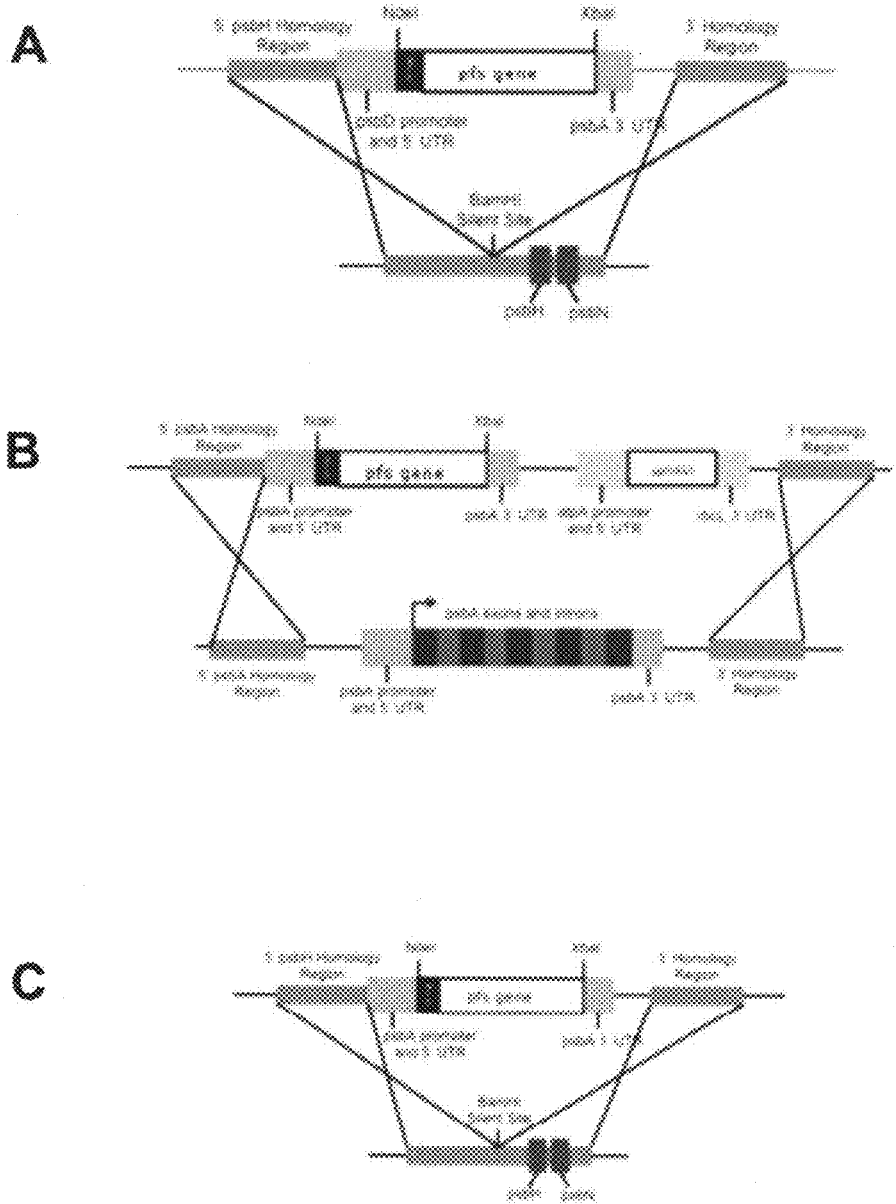
Figure 8:
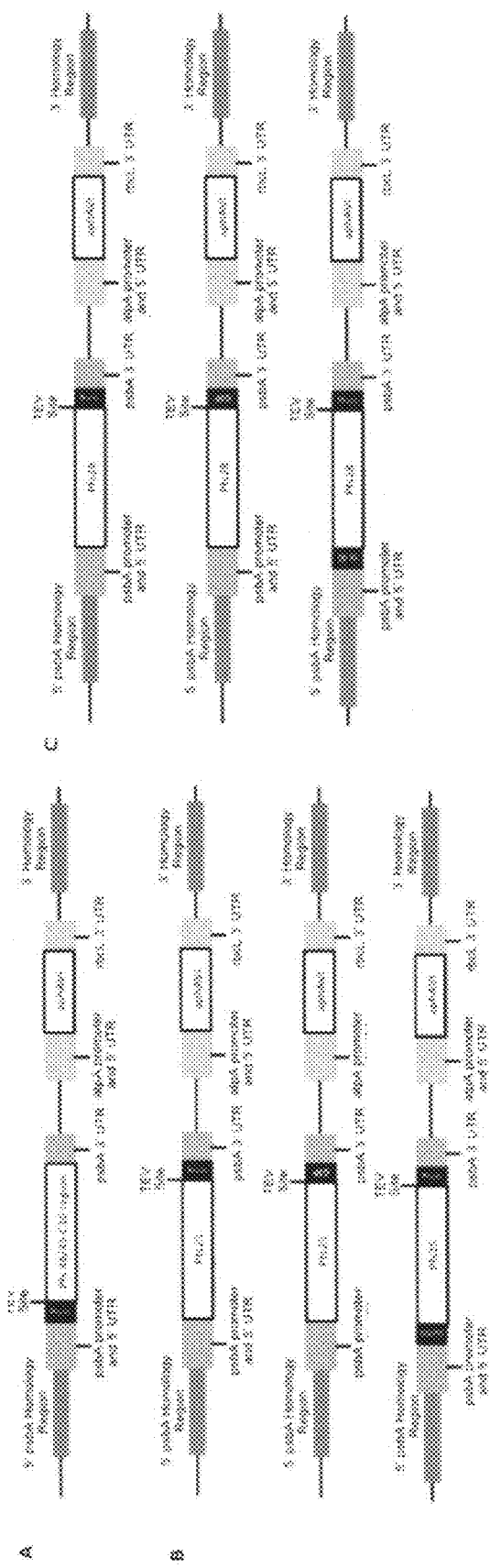
Figure 9A:
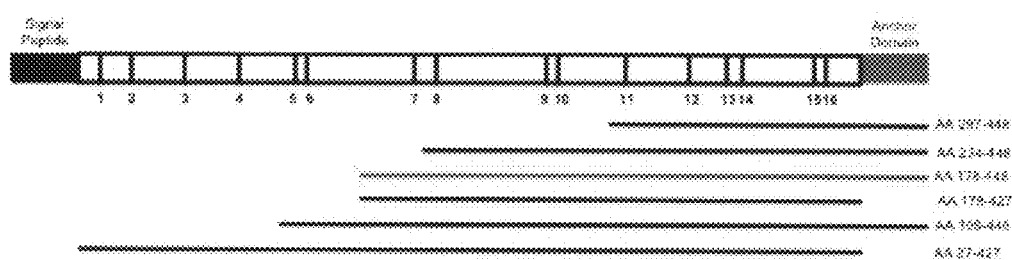

Nine plasmids containing variations in the c.r.Pfs48/45 coding sequence, protein expression tags, promoters and 5' UTRS were successfully integrated into the chloroplast genome of C. reinhardtii (FIG. 9). Specifically, these nine strains differed by variations in two expression tags, FLAG and SAA, usage of either the psbA or psbD promoter and 5' UTR, and they contained variable lengths of coding sequence for the c.r.Pfs48/45 gene. The coding sequence variations included the presence or absence of the C-terminal anchor domain (AA 427-448) and the presence or absence of the domain containing the first 6 cysteine amino acids within the original Pfs48/45 sequence (AA 27-427 versus AA 178-427). Of these nine strains, only two (strains 391 and 389) containing the shorter amino acid sequence encoding the domain containing 10 cysteines and the C-terminal anchor domain, were shown to result in protein accumulation.

Both strains 391 and 389 contain the codon optimized gene sequence for expression of amino acids 178-448 of the native Pfs48/45 peptide with a FLAG expression tag located at the N-terminus. These two strains only differed in the site of integration within the chloroplast genome and the use of the promoter and 5' UTR from either psbA (D1, 391) or psbD (D2, 389) (FIG. 9B-C). Due to strain 389 having much lower expression levels based on Western blotting, strain 391 was used for larger scale production and further analysis of the protein expressed in the chloroplast of C. reinhardtii.

The presence of the c.r.Pfs48/45 gene sequence in strain 391 was confirmed by primer specific PCR, and the recombinant gene was shown to occupy the psbA insertion site in all copies of the chloroplast genome through colony PCR screening (FIG. 10A-B). In order to confirm that the gene sequence was being transcribed within the chloroplast of C. reinhardtii, total RNA was isolated and used for a qualitative RNA analysis. The analysis confirmed the c.r.Pfs48/45 gene was being transcribed within the chloroplast of the *C. reinhardtii* strain 391. (FIG. 10C).

Following growth to middle logarithmic phase, gene expression in algal cultures was induced by high light exposure for 24 hours (Manuell et al (2007) *Plant Biotech. J.* 5:402-412). The 391 algal cells were pelleted and used for c.r.Pfs48/45 protein isolation and purification. Western blot analysis of total protein extracts using a monoclonal anti-FLAG-M2 alkaline phosphatase conjugated antibody recognized proteins of approximately the predicted size for strain 391 at 34 kD. This flag-tagged protein was present in the total protein extract and was significantly concentrated when proteins were eluted from an anti-FLAG affinity resin (FIG. 11A).

Soluble protein concentrate from strain 391 c.r.Pfs48/45 shows the presence of two proteins of distinct sizes in the Western blot. The top band of approximately 40 kD is likely the reduced protein containing the entire 391 c.r.Pfs48/45 protein while the smaller band of approximately 21 kD is likely a cleavage product of the protein. Above these two bands are two faint bands that likely represent the unreduced folded 391 c.r.Pfs48/45 protein at approximately 60 kD and a potential protein multimer at 150 kD.

To confirm that the FLAG antibody was recognizing the correct 391 c.r.Pfs48/45 protein, an eluted protein extract was analyzed by mass spectrometry. Three peptides matching those expected in the 391 c.r.Pfs48/45 protein were identified (FIG. 11B).

To confirm that 391 c.r.Pfs48/45 folded in a manner conducive to the formation of the conformational-dependent epitopes necessary for antigenicity, both a Western blot and ELISA assay were completed using the conformational specific Pfs48/45 antibody IIC5-10 (MRA-26). FIG. 12A shows the Western blot using the MRA-26 antibody (lanes 4 and 5) compared to a FLAG specific antibody (lanes 1 and 2). When the 391 c.r.Pfs48/45 protein was under reduced conditions, the FLAG specific antibody clearly recognized the peptides of the appropriate size, while the unreduced sample revealed bands at higher molecular weights. However, when the 391 c.r.Pfs48/45 protein was reduced prior to exposure to the MRA-26 antibody, no peptides were recognized, as predicted because the epitope was denatured. Exposure of the MRA-26 antibody to the unreduced 391 c.r.Pfs48/45 protein revealed the presence of a band on the Western blot at approximately 130 kD. These results show that the conformation-specific Pfs48/45 antibody, MRA-26, only recognizes the 391 c.r.Pfs48/45 protein when it is in its unreduced conformation and suggest that this algal chloroplast accumulated protein folded in the correct conformation. The Western results were further confirmed with an ELISA assay using both reduced and non-reduced protein samples incubated with the MRA-26 antibody (FIG. 12B). The exposure of both reduced and unreduced 391 c.r.Pfs48/45 and a control bovine serum albumin (BSA) standard to the MRA-26 antibody clearly shows that the recognition of this antibody is specific to the unreduced 391 c.r.Pfs48/45 protein.

Discussion

Despite its promise as a transmission blocking malaria vaccine candidate, the *P. falciparum* surface protein Pfs48/45 has proven to be a difficult target for multiple heterologous expression platforms (Chowdhury et al (2009) *PLOS One.* 4:e6352; Outchkourov et al (2007) *J. Biol. Chem.* 282:17148-17156; Outchkourov et al (2008) *Proc. Nat. Acad. Sci. USA* 105:4301-4305; Milek et al (1998) *Exper. Parasitol.* 90:165-174; Milek et al (2000) *Vaccine.* 18:1402-1411; Kocken et al (1993) *Mol. Biochem. Parasitol.* 61:59-68). These expression complications are likely due to structural discrepancies preventing antigen recognition including the complexity of the disulfide bridges formed within the repeated 6 cysteine-containing domain structure that is common to this family of *P. falciparum* surface proteins (Van Dijk et al (2010) *PLOS Pathogens.* 6:e1000853; Sutherland (2009) *Mol. Biochem. Parasitol.* 166:93-98; Outchkourov et al (2008) *Proc. Nat. Acad. Sci. USA* 105:4301-4305). Additionally, in expression systems that can accumulate complex proteins, post-translational modifications of the recombinant Pfs48/45 protein may prevent the formation of the correct conformation due to the lack of N-linked glycosylation machinery for endogenous *Plasmodium* proteins (Outchkourov et al (2008) *Proc. Nat. Acad. Sci. USA* 105:4301-4305). However, the model green alga *C. reinhardtii* whose chloroplast has been shown to provide an environment conducive to the formation of proteins containing complex disulfide bridges that lack post-translational modifications such as glycosylation is an ideal candidate for the production of a malarial transmission blocking vaccine (Tran et al (2009) *Biotech. Bioeng.* 104:663-673; Mayfield et al (2003) *Proc. Nat. Acad. Sci. USA* 100: 438-442). In this study, a gene sequence codon optimized for expression in the chloroplast of *C. reinhardtii* was created and used to construct a series of nine plasmids to test for expression of the Pfs48/45 protein in the chloroplast.

Of the nine *C. reinhardtii* strains, only two (strains 389 and 391) resulted in detectable levels of protein expression. Expression in these two strains may be a result of increased protein stability due to the expression of a smaller protein domain, decreased disulfide bridge formation complexity, or the presence of the C-terminal anchor domain. Strains 389 and 391 contain only 10 of the 16 possible cysteines from the full-length c.r.Pfs48/45 protein. These 10 cysteines should result in the formation of only 5 disulfide bridges compared to 8 in other strains containing the full-length peptide and may result in enough stability to allow for protein accumulation. Previous studies have shown that a similar C-terminal 10-cysteine containing protein region optimized for expression in *E. coli* had greater stability, solubility and epitope recognition resulting in better transmission blocking activity (Outchkourov et al (2007) *J. Biol. Chem.* 282:17148-17156; Outchkourov et al (2008) *Proc. Nat. Acad. Sci. USA* 105:4301-4305). Another factor potentially impacting the expression of the c.r.Pfs48/45 protein in four of the *C. reinhardtii* strains failing to accumulate protein (strains 399, 547, 549, and 551) may be the absence of the Pfs48/45 C-terminal anchor domain. Strains 389 and 391 both contain this C-terminal anchor domain sequence and the accumulation of protein from these strains may be due to protein interaction with the membrane allowing for added stability in chloroplasts. However, strains 401, 472, and 484 contain this C-terminal anchor domain but show no protein accumulation. This lack of accumulation may be due to the presence of the large and very soluble SAA protein expression tag on the N-terminus of the peptide in these strains compared to the smaller FLAG expression tag in strains 389 and 391. This SAA expression tag may keep the recombinant protein in the soluble protein fraction for a longer period of time allowing for protease degradation resulting in undetectable recombinant protein accumulation levels. Ongoing studies focused on understanding the impact of variations in expression tags and coding sequence lengths as well as the impact of the presence or absence of the C-terminal anchor domain in c.r.Pfs48/45 strains and its interaction with the chloroplast membrane will help guide further research on Pfs48/45 protein expression in the chloroplast of *C. reinhardtii*.

Lower levels of protein expression in strain 389 led to the use of strain 391 for all further characterization. To begin, PCR analysis showed the homoplasmic incorporation of the c.r.Pfs48/45 gene within the chloroplast genome of strain 391. The complete homoplasmic replacement of the psbA gene is critical for high levels of expression, as the psbA gene product (the D1 protein) has been shown to play a role in auto-attenuation of translation from any construct containing the psbA promoter and UTR (Manuell et al (2007) *Plant Biotech. J.* 5:402-412; Mayfield et al (2003) *Proc. Nat. Acad. Sci. USA* 100: 438-442). In order to rule out expression problems at the transcriptional level, qualitative cDNA analysis was also used to show that 391 c.r.Pfs48/45 RNA was present in the light induced *C. reinhardtii* cultures.

To show protein expression, the accumulation of the 391 c.r.Pfs48/45 protein was analyzed through Western blot analyses. The presence of the 391 c.r.Pfs48/45 protein in the total protein extract, but limited presence within the soluble protein extract, through multiple attempts indicates that this protein may be found at higher concentrations associated with the membrane portion of the total protein extract. As mentioned earlier, the presence of the Pfs48/45 C-terminal anchor on the 391 c.r.Pfs48/45 protein may be the reason for the lower levels of protein accumulation shown in the soluble fraction.

Accumulation results also show a cleavage product of about 20 kD. This cleavage product is not surprising due to previous studies showing parts of the Pfs48/45 protein to be more resistant to trypsin digestion (Outchkourov et al (2007) *J. Biol. Chem.* 282:17148-17156). These trypsin resistant regions may also be more resistant to other types of proteases both during the in vivo expression of the protein in the chloroplast and during protein isolation and purification. This cleavage product is further supported by the initial isolation results for the native full length Pfs48/45 protein from malaria parasites where there was a similar pattern of cleavage. This isolation also presented a very large protein likely due to unreduced tertiary and quarternary protein structures (Rener et al (1983) *J. Exp. Med.* 158:976-981).

To further support the accumulation data and confirm the identity of the recombinant 391 c.r.Pfs48/45 protein, these peptides were analyzed by mass spectrometry. This analysis found three peptides matching the Pfs 48/45 amino acid sequence. These three peptides were also located in three different regions of the protein indicating that the entire 391 c.r.Pfs48/45 domain is being expressed.

Finally, the biological activity of the Pfs48/45 protein is dependent on the presence of conformation-dependent epitopes (Sutherland (2009) *Mol. Biochem. Parasitol.* 166: 93-98; Outchkourov et al (2007) *J. Biol. Chem.* 282:17148-17156; Vermeulen et al (1985) *J. Exp. Med.* 162:1460-1476). Of these 5 epitopes present on the native protein, three (epitopes I, IIb and III) have been shown to result in naturally occurring antibody responses and have the greatest potential impact on transmission blocking activity (Graves et al (1992) *Am. J. Trop. Med. Hyg.* 46:711-719). A conformation-specific antibody, IIC5-10, (MRA-26) recognizes epitope III on Pfs48/45 when the protein is folded, and the correct pattern of disulfide bonds is present (Carter et al (1990) *Parasite Immunol.* 12:587-603; Targett et al (1990) *Immunol. Let.* 25:77-82; Vermeulen et al (1985) *J. Exp. Med.* 162:1460-1476; Rener et al (1983) *J. Exp. Med.* 158:976-981). To determine if the 391 c.r.Pfs48/45 protein domain contained this folded epitope the MRA-26 antibody was used in both Western blot and ELISA analysis of reduced and unreduced samples. These resulted in the specific recognition of only unreduced 391 c.r.Pfs48/45, confirming the presence of the folded epitope.

The MRA-26 antibody has previously been shown to specifically recognize Pfs48/45 antigens associated with that antigen's transmission blocking activity (Targett et al (1990) *Immunol. Let.* 25:77-82; Rener et al (1983) *J. Exp. Med.* 158:976-981). The recognition of only unreduced 391 c.r.Pfs48/45 by MRA-26 likely demonstrates that the *C. reinhardtii* expressed protein has the conformation necessary to induce transmission blocking activity. Further analysis of antibody elicitation in mice and transmission blocking bioactivity assays are ongoing to confirm these results.

This study shows that the chloroplast of *C. reinhardtii* is a viable platform for the production of the transmission-blocking vaccine candidate Pfs48/45, and that this host accumulates a protein that contains a conformation conducive to the induction of transmission blocking antibodies. The expression of this *P. falciparum* antigen in the chloroplast of *C. reinhardtii* is significant because it demonstrates a novel method to produce this protein at large scales and also because algae have the potential to be developed for oral delivery of a malaria vaccine, similar to those shown from the chloroplast of higher plants (Davoodi-Semiromi et al (2010) *Plant Biotech. J.* 8:223-242; Webster et al (2009) Production and characterization of an orally immunogenic *Plasmodium* antigen in plants using a virus-based expression system. Plant Biotech. J. 7:846-855). The expression of a transmission blocking vaccine antigen in a scalable and edible expression system may enable the availability of such a vaccine to people around the world. The accumulation of the C-terminal region of the Pfs48/45 antigen in the chloroplast of *C. reinhardtii* is an important step.

Example 2

Algae-Produced Pfs25 Elicits Antibodies that Inhibit Malaria Transmission

Materials and Methods
Plasmid Construction.

The peptide sequences of Pfs25(Ala22-Thr193) (Genbank accession: AAD55785) and Pfs28(Val24-Pro179) (Genbank accession: AAG27295) were reverse translated with the gene designer algorithm from DNA2.0 (Menlo, Calif., USA) using the *C. reinhardtii* complete codon usage table as a reference set (on the internet at kazusa.or.jp). The codon bias of the sequence was validated by computing the expected codon adaptation index (eCAI) [Puigbo et al (2008) *BMC Bioinformatics* 9:65]. The codon optimized algal-pfs25 (a-pfs25) and algal-pfs28 (a-pfs28) were synthesized by GeneArt® (now Life Technologies Carlsbad, Calif., USA) and cloned into the pD1-KanR [Rasala et al (2011) *Bioeng Bugs* 2: 50-54], which contains 5' and 3' psbA homology to direct homologous recombination to the psbA locus and a kanamycin resistance cassette for selection. The resulting plasmids contain a-pfs25 (pJAG9) or a-pfs28 (pJAG15) fused to a 3' TEV protease recognition sequence followed by a FLAG affinity tag. Synthetic pfs genes are downstream of the psbA promoter and 5' UTR and upstream of the psbA 3' UTR. Each construct was verified by sequencing (Retrogen, San Diego, Calif.).

*C. reinhardtii* Transformation.

*C. reinhardtii* strain W1.1 [Manuell, et al. (2007) *Plant Biotechnol J* 5: 402-412] was grown in TAP (Tris-acetate-phosphate) medium at 23° C. on a rotary shaker to mid log phase and harvested by centrifugation. Approximately $5 \times 10^7$ cells were plated on TAP agar with 100 μg/ml kanamycin and transformed by particle bombardment [Boynton, et al. (1988) *Science* 240: 1534-1538]. Briefly, 1 mg of gold particles (S550d, Seashell technologies, San Diego) coated with 10 μg of plasmid DNA were shot with the PDS-1000/He system (Biorad, Hercules, Calif.) under vacuum at a distance of 9 cm at 1350 psi. Transformants were propagated on TAP agar with 150 µg/mL kanamycin and screened for the presence of a-pfs25 or a-pfs28 using gene specific primers and for homoplasmicity as previously described [Rasala, et al. (2010) *Plant Biotechnol J* 8:719-733].

Western Blotting, Silver Staining, and Affinity Purification of a-Pfs25 and a-Pfs28.

Initial screens for Pfs protein were performed on homoplasmic strains in 250 ml TAP cultures grown on a rotary shaker. Cultures were grown in low light to mid log phase and then switched to high light (~5000 lux) conditions. Samples were harvested at various timepoints post-light shift and resuspended in 1 ml lysis buffer per 0.1 g wet algal paste (50 mM Tris pH 8.0, 400 mM NaCl, 0.1% Tween 20, protease inhibitor cocktail (Roche—Mannheim, Germany)). Cells were lysed by sonication and cleared by centrifugation at 30,000×G for 15 minutes. Total and soluble protein samples were prepared in SDS buffer with urea and DTT at a final concentration of 50 mM Tris, 2% SDS, 10% glycerol, 2M urea, and 100 mM DTT. Samples were heated at 37° C. for 10 min then resolved on RUNBLUE precast 12% SDS-PAGE gels (Expedeon—San Diego, Calif.) and transferred to nitrocellulose membranes. Blots were probed with mouse anti-FLAG primary mAb (Sigma Aldrich—St. Louis, Mo.) and alkaline phosphatase (AP)-conjugated goat anti-mouse IgG secondary Ab (Sigma-Aldrich) and visualized using nitroblue tetrazolium (NBT) and 5-bromo-4-chloro-3'-indolylphosphate p-toluidine salt (BCIP) in alkaline phosphatase buffer.

A-Pfs25 and A-Pfs28 were purified from 20 liters of TAP medium grown in photobioreactors. Photobioreactors were constructed from Nalgene carboys (part#-2251-0050) fitted with Nunc bulkhead adapters (part#-6149-002) for bubbling air through a 0.1 micron filter. Photobioreactors were inoculated with 250 ml starter cultures at late log phase and grown in the dark until reaching an approximate density of $1 \times 10^6$ cells/mL and then shifted to high light (~5000 lux). Optimal yields were reached when harvesting 5-8 hrs post-light induction. Cells were harvested using a Lavin L2 continuous flow centrifuge (AML ind.—Hatboro, Pa.) fed by a peristaltic pump. Total soluble protein was isolated as described above. M2 anti-FLAG resin (Sigma Aldrich) was added to the cleared lysate and rotated end over end at 4° C. for 2 hrs. Resin was washed with 20 volumes of lysis buffer twice and once with lysis buffer without Tween 20. Resin was then collected by filtration in a Bio-rad Econo-pac column and the protein was eluted using 100 mM glycine pH 3.5, 400 mM NaCl and neutralized with Tris pH 8.0 to a final concentration of 50 mM. Eluted fractions were resolved by SDS-PAGE and analyzed by Western blot as described above. All fractions were then combined and buffer exchanged using Vivaspin 6 centrifugal concentrators (GE Healthcare) with a 10 kDa molecular weight cutoff into PBS. The concentration of purified protein was determined using BioRad protein Assay (Biorad). Reduced samples were prepared in SDS buffer with 10% β-mercaptoethanol (BME) and heated to 90° C. for 10 min. Non-reduced samples were prepared using 4× Native Buffer (Expedeon). Both reduced and non-reduced samples were resolved on RUNBLUE 16% SDS-PAGE (Expedeon) for analysis by Western blot. For gel staining, samples were resolved on 4-20% gradient SDS-PAGE precast gels (Biorad) and stained using silver stain plus (Biorad) or Coomassieblue. Samples for Native-PAGE analysis were prepared with 4× Native Buffer (Expedeon) and resolved by 10% Native-PAGE precast gel (Expedeon) then stained with Coomassieblue.

Anti-Pfs25 4B7 monoclonal antibody was prepared from a mouse hybridoma cell line 4B7.1.1 (ATCC—HB-12575). Cells were grown in hybridoma-SFM media (Gibco, 12045) supplemented with 10% FBS (Gemini) and antibodies were harvested after seven days. Reduced and non-reduced a-Pfs25 and a-Pfs28 were prepared as above. Both were resolved on RUNBLUE 16% SDS-PAGE precast gels (Expedeon) and transferred to a nitrocellulose membrane. The blot was probed using filtered lysate containing anti-Pfs25 4B7 mAbs for a-Pfs25 or anti-Pfs28-2D8. Antibody binding detected using alkaline phosphatase-conjugated goat anti-mouse secondary (Sigma-Aldrich) and visualized using NBT and BCIP in alkaline phosphatase buffer.

Circular Dichroism.

Far-UC CD spectra were recorded from 190-260 nm with a 0.1 nm data pitch using a Jasco J-815 spectropolarimeter and 1 mm path length. The cuvette chamber temperature was maintained at 20° C. by a Jasco PFD-425S/15 temperature unit. Samples were at 21 µM and 27 µM in PBS for Pfs28 and Pfs25, respectively. Spectra were acquired at 1 nm band width, 4 second response time, and a scan speed of 100 nm/min. The results were calculated after subtracting the PBS baseline spectra and reported as mean residue ellipticity. Helical, β-strand, and turn content were predicted using CDSSTR on Dichroweb [Sreerama et al (2000) *Anal Biochem* 287: 252-260; Sreerama et al (2000) *Anal Biochem* 287: 243-251].

Mass Spectrometry.

Pfs25 treated with 0.5 mg/mL of iodoacetamide for 30 min at 37° C. to carboxymethylate the cysteine residues that were not in cysteine cross-link bonds. The reaction was quenched with addition of 2 mM DDT followed by buffer exchange using 10 kDa cutoff membrane in 1×TNE buffer (50 mM Tris pH 8.0, 100 mM NaCl, 1 mM EDTA). RapiGest SF reagent (Waters Corp.) was added to the mix to a final concentration of 0.1% and samples were boiled for 5 min. TCEP (Tris (2-carboxyethyl) phosphine) was added to 1 mM (final concentration) and the samples were incubated at 37° C. for 30 min. Proteins samples prepared as above were digested with trypsin (trypsin:protein ratio—1:50) overnight at 37° C. RapiGest was degraded and removed by treating the samples with 250 mM HCl at 37° C. for 1 h followed by centrifugation at 14000 rpm for 30 min at 4° C. The soluble fraction was then added to a new tube and the peptides were extracted and desalted using Aspire RP30 desalting columns (Thermo Scientific). Trypsin-digested peptides were analyzed by high pressure liquid chromatography (HPLC) coupled with tandem mass spectroscopy (LC-MS/MS) using nano-spray ionization. The nanospray ionization experiments were performed using a TripleTOF 5600 hybrid mass spectrometer (ABSCIEX) interfaced with nano-scale reversed-phase HPLC (Tempo) using a 10 cm$^{-180}$ micron ID glass capillary packed with 5-µm C18 Zorbax™ beads (Agilent Technologies, Santa Clara, Calif.). Peptides were eluted from the C18 column into the mass spectrometer using a linear gradient (5-60%) of ACN (Acetonitrile) at a flow rate of 250 µL/min for 1 h. The buffers used to create the ACN gradient were: Buffer A (98% H$_2$O, 2% ACN, 0.2% formic acid, and 0.005% TFA) and Buffer B (100% ACN, 0.2% formic acid, and 0.005% TFA). MS/MS data were acquired in a data-dependent manner in which the MS1 data was acquired at m/z of 400 to 1250 Da and the MS/MS data was acquired from m/z of 50 to 2,000 Da. Finally, the collected data were analyzed using MASCOT® (Matrix Sciences) and Protein Pilot 4.0 (ABSCIEX) for peptide identifications.

Preparation of Mouse Antisera.

Animal experimental protocols were approved by the Institutional Animal Care and Use Committee of the University of California. Balb/c mice were vaccinated by intraperitoneal injection with 25 µg of affinity purified a-Pfs25 or a-Pfs28 emulsified in complete Freund's adjuvant (Sigma-Aldrich). Four boosters were given at two week intervals with 15 µg of affinity purified a-Pfs25 or a-Pfs28 using incomplete Freund's adjuvant (Sigma-Aldrich). Blood was collected prior to immunization and one week following the final immunization.

Enzyme-Linked Immunosorbent Assay.

The percent of a-Pfs25 and a-Pfs28 in the soluble protein fraction was measured by ELISA. The soluble protein lysates from JAG9 (a-Pfs25) and JAG15 (a-Pfs28) were compared to soluble protein from the untransformed parental strain (W1.1) with a known amount of affinity purified a-Pfs25 or a-Pfs28 as follows. Soluble protein fractions were prepared by sonication followed by centrifugation at 20,000×g. Affinity purified a-Pfs25 or a-Pfs28 was mixed with soluble protein from W1.1 at a 1:50 ratio, or 2%, and diluted to a final concentration of 0.5 mg/mL in PBS. A standard curve was then prepared using two-fold serial dilutions with a 0.5 mg/ml solution of W1.1 soluble protein. MaxiSorp™ plates (Nunc—Rochester, N.Y.) were coated in triplicate with 50 µg of soluble protein from JAG9, JAG15, or the prepared standard curve and incubated overnight at 4° C. on a rocker. Wells were washed three times with PBS with 0.1% Tween (PBS-T) and blocked with 5% milk in PBS-T for 2 hrs at room temperature. A-Pfs25 and a-Pfs28 were detected with M2 anti-FLAG mAbs diluted 1:4000 in PBS-T and goat anti-mouse horse radish peroxidase (Thermo Scientific—Rockford, Ill.) at 1:5000. Antibody binding was detected using the TMB substrate kit (Thermo Scientific) and read with an Infinite M200 pro plate reader (Tecan—Switzerland) at 450 nm.

IgG titers in the mouse antisera against a-Pfs25 and a-Pfs28 were measured by ELISA as follows. A-Pfs25 and a-Pfs28 were diluted to 1 µg/ml in PBS and used to coat 96-well MaxiSorp™ plates (Nunc—Rochester, N.Y.) and incubated overnight at 4° C. on a rocker. Wells were washed three times with PBS-T and blocked with 5% milk in PBS-T for 2 hours at room temperature. Serum samples were prepared by 1:5 serial dilutions from 1:100 to 1:62500, followed by 1:2 dilutions from 1:65000 to $8 \times 10^7$, plated in triplicate, and incubated overnight at 4° C. IgG titers were detected using AP-conjugated goat anti-mouse IgG (Sigma-Aldrich) at 1:4000 in PBS-T for two hours at room temperature and visualized using p-Nitrophenylphosphate (Enzo Life Sciences—Farmingdale, N.Y.) as the substrate. Absorbances were measured at 450 nm using Infinite M200 pro plate reader (Tecan—Switzerland).

Western Blotting of Parasite Lysates.

*Plasmodium falciparum* strain NF54 was maintained in vitro in continuous cultivation. Gametocytes, macrogametes, zygotes, and ookinetes were cultured and purified as previously described [Bounkeua et al (2010) *Am J Trop Med Hyg* 83: 1187-1194]. For antibodies raised to a-Pfs25, 2 µg of reduced and nonreduced parasite lysate was prepared as described above and resolved on RUNBLUE 12% SDS-PAGE precast gels (Expedeon). Resolved proteins were transferred to nitrocellulose and probed with antisera raised to a-Pfs25 at a 1:100 dilution. Identical blots were prepared and probed with anti-Pfs25 4B7 mAbs or preimmune sera. For antibodies raised to a-Pfs28, 20 µg was prepared in an identical manner and probed with a-Pfs28 antisera at a 1:100 dilution or preimmune sera. All membranes were visualized using AP-conjugated goat anti-mouse IgG antibodies.

Indirect Immunofluorescence.

Fixed, permeabilized gametocytes, macrogametes, and zygotes were subjected to IFA. Parasites were heat-fixed onto 10-well glass slides (Fisher Scientific). Fixed cells were permeabilized by incubation in PBS containing 3% bovine serum albumin and 0.1% Triton X-100 at room temperature for 15 minutes followed by blocking for 2 hrs at room temperature in 3% BSA in PBS-T. The preparations were incubated with a-Pfs25 or a-Pfs28 antisera (1:100 dilution) or 4b7 mAbs overnight at 4° C. followed by Alexa Fluor 488 goat anti-mouse IgG (1:500 dilution; Molecular Probes) at room temperature for 1 hr. Parasite nuclei were stained with 2 µg/mL 4'-6-Diamidino-2-phenylindole (DAPI; Molecular Probes) at room temperature for 5 min. Slides were mounted with SlowFade® anti-fade kit (Molecular Probes) and images were acquired using an Applied Precision Spectris microscope and deconvolved using Softworx software (Applied Precision—Issaquah, Wash.). Images were adjusted for contrast in Softworx and exported as tiffs and assembled with Adobe Photoshop.

Standard Membrane Feeding Assay.

Transmission blocking activity was assessed by standard membrane feeding [Isaacs, et al. (2011) *PLoS Pathog* 7: e1002017]. *Anopheles stephensi* STE2 was maintained at 27° C. and 80% relative humidity on a 12 hr day/night light cycle. Larvae were fed a diet of powdered fish food (Tetramin) mixed with yeast. Adults were provided a 10% sugar solution. Four to six day-old female *A. stephensi* mosquitoes were fed with *P. falciparum* NF 54 gametocytes in the presence of heat inactivated control or immune sera or mAbs using a membrane feeding apparatus. Heat inactivation was performed at 56° C. for 45 min. After 15 min of feeding, un-engorged mosquitoes were removed and engorged mosquitoes were maintained in the insectary under standard conditions [Benedict M (1997) Care and maintenance of anopheline mosquito colonies: Chapman and Hall, London]. Midguts were dissected 9 days after the infectious bloodmeal, stained with 0.1% mercurochrome and the number of oocysts in each preparation counted. Uninfected bloodmeals were provided to wild-type control mosquitoes following the membrane feeding. Infected female mosquitoes were dissected for oocyst counts nine days after infection. Statistics were calculated in JMP ver. 9.0.2 (SAS—Cary, N.C.) using a single tailed Wilcoxon nonparametric comparison.

Results

Production and Purification of Recombinant Pfs25 and Pfs28 in Algal Chloroplasts.

We synthesized genes encoding pfs25(Ala22-Thr193) and pfs28(Val24-Pro179) with a codon bias that resembles the *C. reinhardtii* chloroplast codon usage (hereafter referred to as a-pfs25 and a-pfs28). Codon optimization of heterologous genes for expression in the chloroplast was previously shown to increase protein yields [Franklin et al (2002) *Plant J* 30: 733-744]. Synthetic a-pfs25 and a-pfs28 each contain four EGF-like domains and a C-terminal FLAG tag for ease of detection and purification, but lack the native signal sequence and GPI-anchor sequence. The expected codon adaptation index (eCAI), which quantitates the codon bias of a transgene against a reference set, is 0.878 (p<0.01) and 0.892 (p<. 01) for a-pfs25 and a-pfs25 respectively [Puigbo et al (2008) *BMC Bioinformatics* 9:65]. CAI values range from zero to one where a score of one indicates that every instance of an amino acid is encoded by the most common codon in the reference codon table [Sharp et al (1987) *Nucleic Acids Res* 15: 1281-1295]. A-pfs25 and a-pfs28 were synthesized and separately cloned into a chloroplast expression cassette that replaces endogenous psbA through homologous recombination such that transgene expression is controlled by the psbA promoter and 5' and 3' untranslated regions (UTRs; FIG. 13A). *C. reinhardtii* chloroplasts were transformed by particle bombardment and a-pfs25 and a-pfs28 were detected by PCR. Transformed *C. reinhardtii* were screened for a-Pfs25 (FIG. 13B—arrow) and a-Pfs28 (FIG. 13C—arrow) protein by Western blot. A-Pfs25 and a-Pfs28 accumulate in chloroplasts at 0.5% and 0.2% total soluble protein, respectively, as determined by ELISA (see materials and methods).

A-Pfs25 and a-Pfs28 were affinity purified using anti-FLAG M2 affinity resin (see materials and methods), positively identified by mass spectrometry, and analyzed by Western blot (FIG. 14A-B). The predominant band in reduced a-Pfs25 and a-Pfs28 migrated near their predicted sizes of 21.4 kDa (FIG. 14A-arrow) and 20.2 kDa (FIG. 14B-arrow), respectively. The sizes of the larger bands suggest that a-Pfs25 and a-Pfs28 could be running as dimers. The monomeric form of a-Pfs25 and a-Pfs28 is diminished in unreduced samples and appears at larger, less well-defined molecular species. Similar to Western blot analysis, Coomassie-blue staining of reduced samples resolved by SDS-PAGE shows a single predominant band with few obvious impurities for both a-Pfs25 and a-Pfs28 (FIG. 14C). Similar results were obtained with silver staining (FIG. 15). A-Pfs25 and a-Pfs28 appear as larger less defined molecular weight complexes when analyzed by native-PAGE (FIG. 14D). The apparent larger size of a-Pfs25 and a-Pfs28 in the non-reduced and native gels could be the result of multimerization that form because both proteins are rich in β-strand secondary structures that are known to interact [Richardson et al (2002) *Proc Natl Acad Sci USA* 99: 2754-2759]. Indeed, multimerization of recombinant *Plasmodium* surface proteins was recently observed [Miyata, et al. (2010) *Infect Immun* 78: 3773-3782; Mlambo et al (2010) *Vaccine* 28: 7025-7029]. Thus, algal chloroplasts produce a single protein that is the appropriate size for a-Pfs25 and a-Pfs28, and those monomers appear to assemble into higher molecular weight aggregates that could have multiple conformations.

Figure 16:
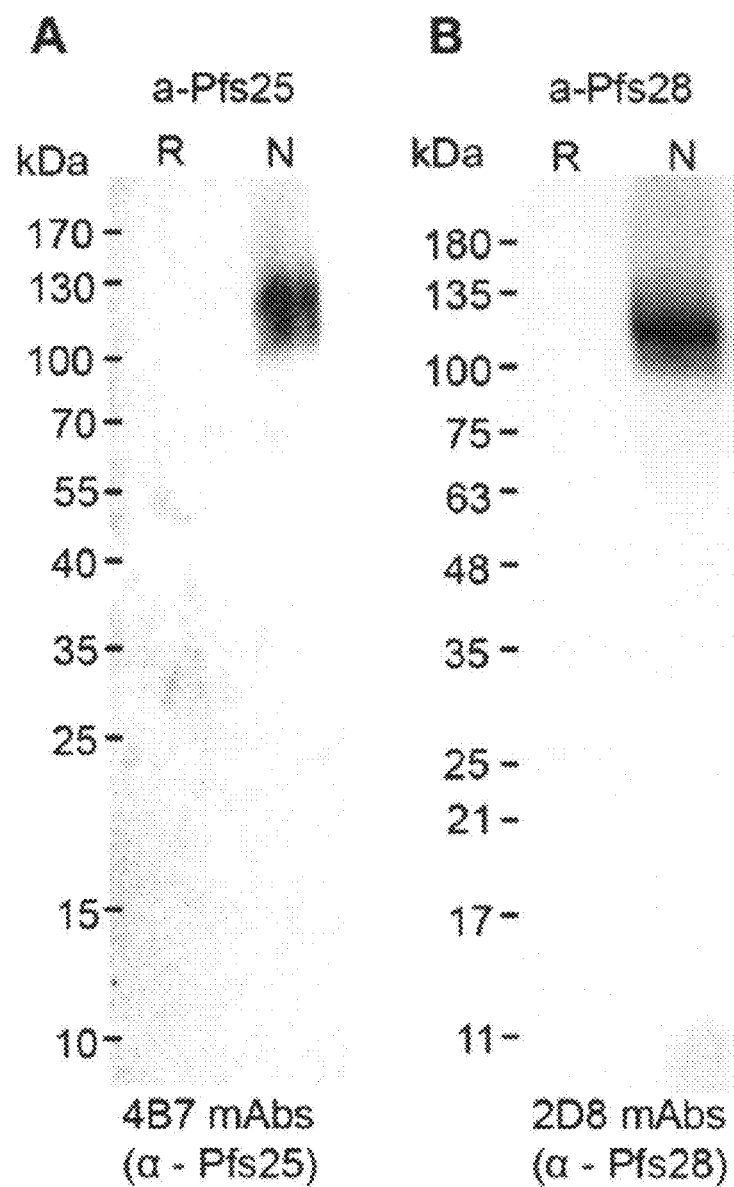

Structural characterization of a-Pfs25 and a-Pfs28. A-Pfs25 and a-Pfs28 were analyzed for the presence of epitopes found in native Pfs25 and Pfs28 by Western blot using transmission blocking monoclonal antibodies 4B7 (Pfs25, [Barr, et al. (1991) *J Exp Med* 174: 1203-1208]) and 2D8 (Pfs28, a gift from David Narum, NIAID [Qian, et al. (2009) *Microbes Infect* 11: 408-412]), which were previously shown to recognize epitopes only present on properly folded Pfs25 and Pfs28, respectively (FIG. 16). Anti-Pfs25-4B7 mAbs recognize a β-hairpin epitope within the ILDTSNPVKT peptide sequence (SEQ ID NO: 47) of the third EGF-like domain of native Pfs25 [Sharma (2008) *In Silico Biol* 8: 193-206; Stura, et al. (1994) *Acta Crystallogr D Biol Crystallogr* 50: 556-562]. Anti-Pfs25-4B7 mAbs binds a-Pfs25 as a band that migrates between 100 and 130 KDa in non-reduced samples (FIG. 16A). Unlike anti-FLAG mAbs (FIG. 14), anti-Pfs25-4B7 does not recognize reduced a-Pfs25, which is consistent with recognition being conformationally dependent. Similarly, anti-Pfs28-2D8 mAbs recognize a-Pfs28 in non-reduced, but not reduced samples, as a larger molecular weight species (FIG. 16B). Thus, a-Pfs25 and a-Pfs28 contain epitopes present on native Pfs25 and Pfs28, respectively.

We assessed the secondary structure of purified a-Pfs25 and a-Pfs28 using circular dichroism (CD) spectroscopy (FIG. 17A). The crystal structure of yeast-produced *Plasmodium vivax* surface protein 25 (Pvs25), a homologue of Pfs25, has two central β-strands separated by a turn [Saxena, et al. (2006) *Nat Struct Mol Biol* 13: 90-91]. Bioinformatic analysis of Pfs25 and Pfs28 suggest their structures are similar [Sharma (2008) *In Silico Biol* 8: 193-206]. Deconvolution of CD spectra with CDSSTR [Sreerama et al (2000) *Anal Biochem* 287: 252-260; Sreerama et al (2000) *Anal Biochem* 287: 243-251], which estimates the contribution of each secondary structure to the overall spectrum, predicts that a-Pfs25 and a-Pfs28 are composed of nearly 60% β-strands and turns, 10% α-helix, and 30% unordered peptide. Thus, the CD spectra reveal that a-Pfs25 and a-Pfs28 have comparable secondary structures that are predicted to be primarily β-strands and turns, which is consistent with the crystal structure of Pvs25.

We analyzed free cysteine residues in a-Pfs25 by mass spectrometry to determine which residues are bridged by disulfide bonds (see materials and methods). Briefly, a-Pfs25 was treated with iodoacetamide to carboxymethylate free cysteines followed by trypsin digestion. Tryptic peptides were analyzed by high pressure liquid chromatography (HPLC) coupled to tandem mass spectrometry (LC-MS-MS) using nanospray ionization. Presumably, cysteines that remained unmodified after treatment with iodoacetamide were protected from modification because they were in disulfide bonds. The detected peptides covered approximately 64% of the Pfs25 sequence (FIG. 17B-underlined). A-Pfs25 digested with GluC and chymotrypsin did not add to the total coverage. When compared to the disulfide bonds identified in crystallized yeast-produced Pvs25, we found that disulfide bonds 1, 4, and 6 are intact while 2, 7, 8, 10, and 11 may not be completely formed in a-Pfs25. Peptides for the remaining disulfide bonds were not detected. Hence, *C. reinhardtii* chloroplasts form disulfide bonds in a-Pfs25, but it may not be as extensively bridged by disulfide bonds as yeast-produced Pfs25.

Antibodies from Mice Vaccinated with a-Pfs25 or a-Pfs28 Recognize Native Parasite Proteins.

Figure 18:
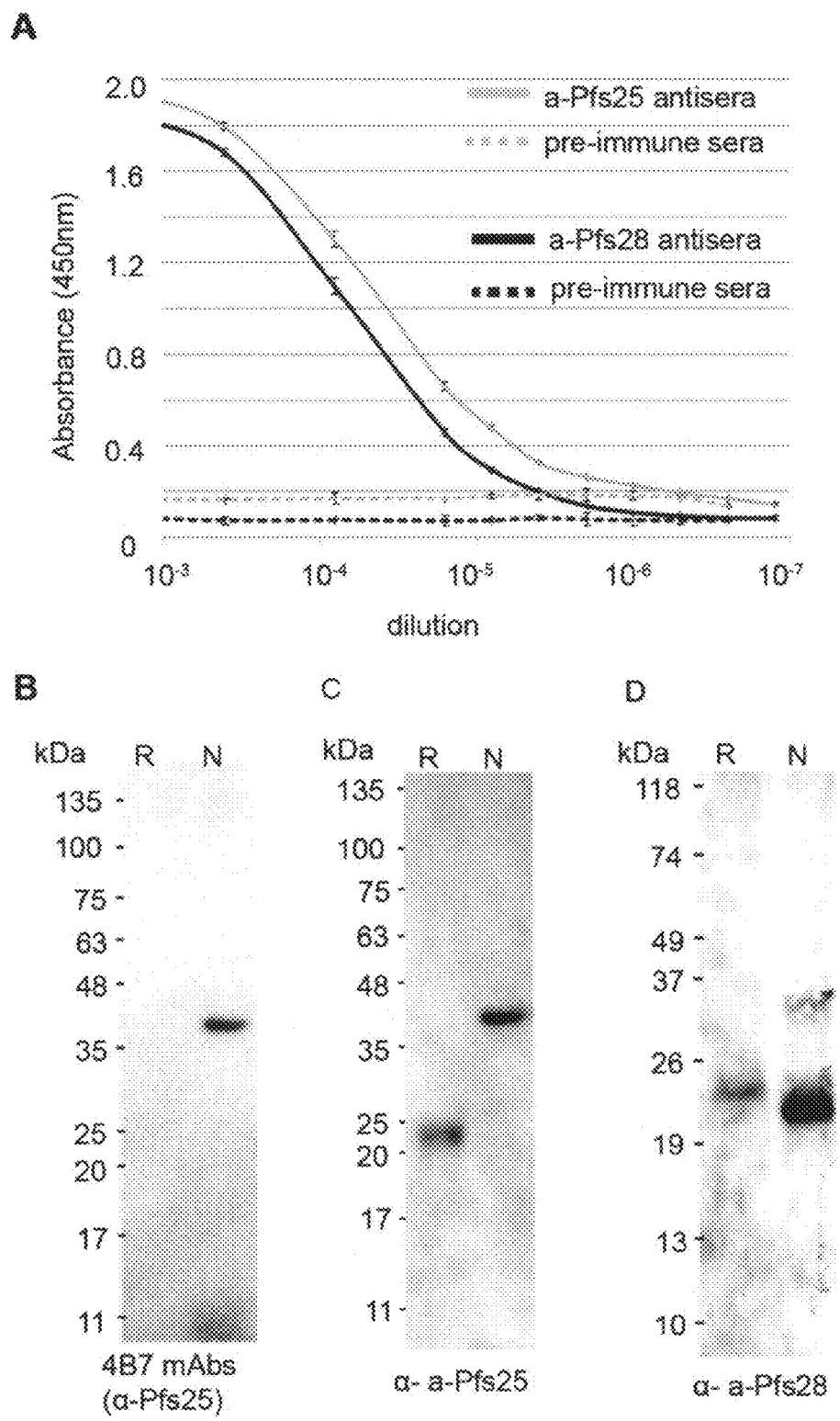

Balb/c mice were immunized with affinity purified a-Pfs25 or a-Pfs28 using complete Freund's adjuvant for the first vaccination and incomplete Freund's adjuvant for subsequent vaccinations. Antibody titers were measured by ELISA against affinity purified a-Pfs25 or a-Pfs28 (FIG. 18A). Sera from mice immunized with a-Pfs25 and a-Pfs28 contained high titers of antibodies for a-Pfs25 and a-Pfs28 respectively. Preimmune sera showed no IgG response to either of these proteins.

We tested the specificity of antibodies raised to algae produced Pfs antigens to native Pfs25 or Pfs28 in sexual stage parasite lysates. Reduced and non-reduced *P. falciparum* sexual stage lysates were probed with anti-Pfs25-4B7 mAbs, anti-Pfs28-2D8 mAbs, and with serum from mice injected with a-Pfs25 or a-Pfs28. As expected, anti-Pfs25-4B7 recognized a band in the non-reduced sample, but not the reduced sample, which is consistent with anti-Pfs25-4B7 recognizing only conformationally-correct Pfs25 (FIG. 17B). Sera from mice injected with a-Pfs25 recognized a 25 kDa band in reduced *P. falciparum* lysates, which is consistent with molecular weight of native Pfs25, and an approximately 40 KDa band that is identical in size to the band recognized by anti-Pfs25-4B7 in non-reduced lysates (FIGS. 18B and C). Antibodies raised to a-Pfs28 recognized an approximately 22 KDa band in both reduced and non-reduced parasite lysates (FIG. 18D), but required ten-fold more parasite lysate than a-Pfs25 antisera for detection. This could be due to lower Pfs28 protein abundance or due to lower affinity antibodies. We did not detect Pfs28 with anti-Pfs28-2D8 mAbs indicating Pfs28 is indeed less abundant than Pfs25 in our in vitro cultured parasites. Importantly, the size of the protein recognized by a-Pfs28 antisera is consistent with antibodies that were previously shown to recognize Pfs28 in sexual stage parasites [Duffy (1997) Infect Immun 65: 1109-1113]. Thus, antisera to both a-Pfs25 and a-Pfs28 recognize native parasite proteins of the appropriate size and a-Pfs25 antisera recognize a band that identical to the transmission blocking anti-Pfs25 4B7 mAbs in non-reduced samples.

Pfs25 and Pfs28 are outer membrane proteins that are produced in P. falciparum sexual stage parasites [Dechering, et al. (1999) Mol Cell Biol 19: 967-978]. We therefore tested the affinity of a-Pfs25 and a-Pfs28 antisera as well as anti-Pfs25-4B7 mAbs and sera from unvaccinated isogenic mice for in-vitro cultured parasites. Binding of a-Pfs25 antisera was predominantly confined to the outer membrane (FIG. 19A; additional images FIG. 20). Staining with anti-Pfs25-4B7 was identical to a-Pfs25 antisera (FIG. 19B and FIG. 20), which suggests antibodies to a-Pfs25 also bind Pfs25. Binding of a-Pfs28 antisera was significantly weaker than a-Pfs25 antisera and often not detectable above background levels seen with sera from unvaccinated isogenic mice (FIG. 20). Similar to Western blot analysis of parasite lysates, this suggests that antibody titers to Pfs28 are low or that Pfs28 is not as abundant as Pfs25 in our in-vitro cultured parasites.

Evaluation of Transmission Blocking Activity of a-Pfs25 and a-Pfs28 Antisera.

Transmission blocking activity was measured by the reduction of oocysts in mosquito midguts by a standard membrane feed assay (SMFA). Briefly, P. falciparum NF 54 gametocytes and heat inactivated antisera from mice immunized with a-Pfs25, a-Pfs28, or sera from isogenic mice were fed to female Anopheles stephensi mosquitoes. Mosquitos were dissected nine days later and analyzed for oocysts (FIG. 21). Oocyst counts were reduced in mosquitos that were fed a-Pfs28 antisera, but transmission blocking activity did not reach significance using a nonparametric comparison test (see materials and methods). Antibodies to a-Pfs25 completely blocked transmission as indicated by the absence of oocysts in all dissected mosquitos. These results are consistent with previous data that suggests that antibodies to Pfs25 more efficiently block malaria transmission than antibodies to Pfs28 [Gozar et al (1998) Infect Immun 66: 59-64; Gozar, et al. (2001) Exp Parasitol 97: 61-69], and that the algal expressed a-Pfs25 protein elicits an antibody response most suitable for vaccine development.

Discussion

In this study, we demonstrated that algae are a robust platform for producing malaria subunit vaccines by characterizing Pfs25 and Pfs28, two structurally complex malaria transmission blocking vaccine candidates, made in C. reinhardtii chloroplasts. Algae are the only recombinant system to date that has successfully produced unmodified aglycosylated recombinant Pfs25 or Pfs28. The algae-produced recombinant proteins are similar in structure to native Pfs25 and Pfs28 and recognized by transmission blocking monoclonal antibodies that only bind conformationally correct Pfs antigens.

Analysis of free cysteines in a-Pfs25 revealed that disulfide bonds are formed by algal chloroplasts in this protein, but these may not be as extensively formed as in the yeast-produced homologue of Pvs25 from P. vivax [Saxena, et al. (2006) Nat Struct Mol Biol 13: 90-91], and this may be an area where the algae system can be improved. However, the disulfide linkages in native Pfs25 are not known, nor have they been characterized in any other recombinant system. The disulfide bonds are likely similar to the native protein because both a-Pfs25 and a-Pfs28 elicit antibodies in mice that recognize native proteins in P. falciparum sexual stage lysates. A-Pfs25, but not a-Pfs28, elicited antibodies with significant levels of transmission blocking activity, which is consistent with previous observations [Gozar et al (1998) Infect Immun 66: 59-64; Gozar, et al. (2001) Exp Parasitol 97: 61-69]. The structural analysis of a-Pfs25 and a-Pfs28 suggests these antigens resemble the native proteins and are of similar conformational quality. The apparent difference in transmission blocking activity between a-Pfs25 and a-Pfs28 is likely due to the delayed appearance of Pfs28 in ookinete development compared to the earlier appearance of Pfs25 in zygote development, rendering any antibodies directed against the later-expressed Pfs28 protein on the parasite superfluous. For these reasons, interest in Pfs28 as a TBV candidate has diminished in recent years compared to Pfs25, which remains the lead TBV candidate.

TBVs and other subunit vaccines must be produced at a cost that is appropriate for low income countries if they are to be implemented. Indeed, financial constraints are already limiting the dissemination of effective meningococcal, pneumococcal, and rotavirus vaccines [Greenwood et al (2011) Clin Microbiol Infect 17:1600-1607]. Algal biomass could be a low cost source for recombinant protein, especially because recent interest in algal biofuels is driving research in large scale algae cultivation, which is certain to reduce the price of algal biomass production. Recombinant proteins could be separated from lipids used for fuel production, which would drive down the cost of both. Alternatively, fusing mucosal adjuvants to vaccine candidates might allow for oral delivery and eliminate the need for injection and cold chain storage [Daniell et al (2009) Trends Plant Sci 14: 669-679; Dreesen et al (2010) J Biotechnol 145: 273-280], both of which significantly contribute to vaccine cost. C. reinhardtii and other algae are generally regarded as safe by the U.S. Food and Drug administration because they do not harbor endotoxins, human pathogens, or other known toxic compounds. Therefore, algae are an ideal platform for producing low-cost subunit vaccines.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An algal cell comprising a polynucleotide comprising a nucleic acid sequence having at least about 90% sequence identity to the full length of SEQ ID NO:13 or SEQ ID NO:2, wherein the nucleic acid sequence encodes a *Plasmodium* surface protein P25.

2. An algal cell comprising the expression cassette comprising a promoter that drives expression of a coding sequence in an algal host cell, wherein the promoter is operably linked to a polynucleotide comprising a nucleic acid sequence having at least about 90% sequence identity to the full length of SEQ ID NO:13 or SEQ ID NO:2, wherein the nucleic acid sequence encodes a *Plasmodium* surface protein P25.

3. A method of producing an algal cell of claim 1, comprising expressing in an algal cell a polynucleotide encoding a nucleic acid sequence having at least about 90% sequence identity to the full length of SEQ ID NO:13 or SEQ ID NO:2, wherein the nucleic acid sequence encodes a *Plasmodium* surface protein P25.

4. The algal cell of claim 1, wherein the algal cell is a *Chlamydomonas reinhardtii* cell.

5. The algal cell of claim 1, wherein the algal cell comprises a polynucleotide comprising a nucleic acid sequence having at least about 95% sequence identity to the full length of SEQ ID NO:13 or SEQ ID NO:2.

6. The algal cell of claim 1, wherein the algal cell comprises a polynucleotide of SEQ ID NO:13 or SEQ ID NO:2.

7. The algal cell of claim 1, wherein the *Plasmodium* surface protein P25 comprises at least one EGF domain and does not comprise a *Plasmodium* signal peptide or transmembrane domain.

8. The algal cell of claim 1, wherein the *Plasmodium* surface protein P25 is a *Plasmodium falciparum* surface protein.

9. The algal cell of claim 1, wherein the nucleic acid sequence is operably linked to a tag selected from the group consisting of an affinity tag, a purification tag, an immunogenicity tag, a delivery tag and a stability tag.

10. The algal cell of claim 1, wherein the nucleic acid sequence is operably linked to a nucleic acid sequence encoding one or more tags selected from the group consisting of poly-His, Mistic, serum amyloid A (SAA), Tic40, small ubiquitin modifier peptide (SUMO), Streptavidin-Binding Peptide (SBP), green fluorescent protein (GFP), FLAG, cholera toxin beta subunit (CTB), and heat-labile enterotoxin beta subunit (LTB).

11. The algal cell of claim 1, wherein the nucleic acid sequence is operably linked to a nucleic acid sequence encoding a cholera toxin beta subunit (CTB).

12. The algal cell of claim 11, wherein the nucleic acid sequence encoding a cholera toxin beta subunit (CTB) has at least 60% sequence identity to SEQ ID NO:32.

13. The algal cell of claim 1, wherein the algal cell further comprises one or more polynucleotides encoding one or more *Plasmodium* polypeptides selected from the group consisting of CDPK4, HAP2, MAPK-2, MDV 1/Peg3, P47, P48/45, P230, PKG, AP2-0, DOZI, HMGP2, Nek-4, CelTOS, CDPK3, Chitinase, CTRP, IMC1b, MAOP, P28, SOAP, Cap380, CSP, ECP1, IMC1a, LAP1/CCp3/SR, LAP2/CCp1, LAP3/CCp5, LAP4/CCp2, LAPS/FNPA, LAP6/CCp4, transglutaminase, CSP, CRMP1, CRMP2, MAEBL, TRAP, and UOS3/TREP/S6.

14. The algal cell of claim 2, wherein the algal cell is a *Chlamydomonas reinhardtii* cell.

15. The algal cell of claim 2, wherein the promoter is selected from the group consisting of psbA and psbD.

16. The algal cell of claim 2, wherein the algal cell comprises a polynucleotide comprising a nucleic acid sequence having at least about 95% sequence identity to the full length of SEQ ID NO:13 or SEQ ID NO:2.

17. The algal cell of claim 2, wherein the algal cell comprises a polynucleotide of SEQ ID NO:13 or SEQ ID NO:2.

18. The algal cell of claim 2, wherein the *Plasmodium* surface protein P25 comprises at least one EGF domain and does not comprise a *Plasmodium* signal peptide or transmembrane domain.

19. The algal cell of claim 2, wherein the *Plasmodium* surface protein P25 is a *Plasmodium falciparum* surface protein.

20. The algal cell of claim 2, wherein the nucleic acid sequence is operably linked to a tag selected from the group consisting of an affinity tag, a purification tag, an immunogenicity tag, a delivery tag and a stability tag.

21. The algal cell of claim 2, wherein the nucleic acid sequence is operably linked to a nucleic acid sequence encoding one or more tags selected from the group consisting of poly-His, Mistic, serum amyloid A (SAA), Tic40, small ubiquitin modifier peptide (SUMO), Streptavidin-Binding Peptide (SBP), green fluorescent protein (GFP), FLAG, cholera toxin beta subunit (CTB), and heat-labile enterotoxin beta subunit (LTB).

22. The algal cell of claim 2, wherein the nucleic acid sequence is operably linked to a nucleic acid sequence encoding a cholera toxin beta subunit (CTB).

23. The algal cell of claim 22, wherein the nucleic acid sequence encoding a cholera toxin beta subunit (CTB) has at least 60% sequence identity to SEQ ID NO:32.

24. The algal cell of claim 2, wherein the algal cell further comprises one or more polynucleotides encoding one or more *Plasmodium* polypeptides selected from the group consisting of CDPK4, HAP2, MAPK-2, MDV 1/Peg3, P47, P48/45, P230, PKG, AP2-0, DOZI, HMGP2, Nek-4, CelTOS, CDPK3, Chitinase, CTRP, IMC1b, MAOP, P28, SOAP, Cap380, CSP, ECP1, IMC1a, LAP1/CCp3/SR, LAP2/CCp1, LAP3/CCp5, LAP4/CCp2, LAPS/FNPA, LAP6/CCp4, transglutaminase, CSP, CRMP1, CRMP2, MAEBL, TRAP, and UOS3/TREP/S6.

25. A method of producing an algal cell of claim 2, comprising expressing in an algal cell a polynucleotide comprising a nucleic acid sequence having at least about 90% sequence identity to the full length of SEQ ID NO:13 or SEQ ID NO:2, wherein the nucleic acid sequence encodes a *Plasmodium* surface protein P25.

* * * * *